US011090357B2

(12) United States Patent
Bhunia et al.

(10) Patent No.: US 11,090,357 B2
(45) Date of Patent: Aug. 17, 2021

(54) BIOENGINEERED LACTOBACILLUS PROBIOTICS AND THE USES THEREOF

(71) Applicant: Purdue Research Foundation, West Lafayette, IN (US)

(72) Inventors: Arun K Bhunia, West Lafayette, IN (US); Rishi Drolia, West Lafayette, IN (US); Ok Kyung Koo, Fayetteville, AR (US); Mary Anne Amalaradjou, West Lafayette, IN (US)

(73) Assignee: Purdue Research Foundation, West Lafayette, IN (US)

(*) Notice: Subject to any disclaimer, the term of this patent is extended or adjusted under 35 U.S.C. 154(b) by 15 days.

(21) Appl. No.: 16/458,243

(22) Filed: Jul. 1, 2019

(65) Prior Publication Data

US 2020/0000876 A1 Jan. 2, 2020

Related U.S. Application Data

(60) Provisional application No. 62/692,880, filed on Jul. 2, 2018.

(51) Int. Cl.

| *A61K 35/747* | (2015.01) |
|---|---|
| *A61K 35/741* | (2015.01) |
| *A61K 39/00* | (2006.01) |
| *A61K 9/19* | (2006.01) |
| *A61K 38/16* | (2006.01) |
| *A61K 9/00* | (2006.01) |
| *A61P 37/06* | (2006.01) |
| *A23K 10/18* | (2016.01) |
| *A61P 31/04* | (2006.01) |

(52) U.S. Cl.
CPC ............ *A61K 38/164* (2013.01); *A23K 10/18* (2016.05); *A61K 9/0056* (2013.01); *A61K 9/19* (2013.01); *A61K 35/741* (2013.01); *A61K 35/747* (2013.01); *A61P 31/04* (2018.01); *A61P 37/06* (2018.01); *A23Y 2220/17* (2013.01); *A23Y 2220/63* (2013.01); *A61K 2039/552* (2013.01)

(58) Field of Classification Search
None
See application file for complete search history.

(56) References Cited

U.S. PATENT DOCUMENTS

2013/0202571 A1* 8/2013 Bhunia ............... A61K 35/747
424/93.45

OTHER PUBLICATIONS

Ahrne, E. et al., "Effect of Lactobacilli on paracellular permeability in the gut", Nutrients, 3, pp. 104-117, 2011.

Amalaradjou, M., et al., "Bioengineered probiotics, a strategic approach to control enteric infections", Bioengineered, 4, pp. 379-387, 2013.
Azcarate-Peril, M., et al., "The intestinal microbiota, gastrointestinal environment and colorectal cancer: a putative role for probiotics in prevention of colorectal cancer?", Am J Physiol—Gastrointest Liver Physiol, 301, pp. G401-G424, 2011.
Bailey, T., et al., Genome sequence of Listeria monocytogenes strain F4244, a 4b serotype. Genome Announcements, 5, e01324-17, pp. 2, 2017.
Ghanem, B., et al., "InlA promotes dissemination of Listeria monocytogenes to the mesenteric lymph nodes during food borne infection of mice", PLoS Pathog, 8, pp. e1003015, 2012.
Bron, P., et al., "Can probiotics modulate human disease by impacting intestinal barrier function?", Brit. J. Nutr. 117, 9, pp. 93-107, 2017.
Burkholder, K., et al., "Listeria monocytogenes uses Listeria adhesion protein (LAP) to promote bacterial transepithelial translocation, and induces expression of LAP receptor Hsp60", Infect. Immun. 78, pp. 5062-5073, 2010.
Burkholder, K., et al., "Expression of LAP, a SecA2-dependent secretory protein, is induced under anaerobic environment", Microbes Infect. 11, pp. 859-867, 2009.
Condette, C., et al., "Increased gut permeability and bacterial translocation after chronic chlorpyrifos exposure in rats", PLoS One 9, e102217, pp. 10, 2014.
Deepti, K., et al., Dahl containing Lactobacillus acidophilus and Bifidobacterium bifidum improves phagocytic potential of macrophages in aged mice. J. Food Sci. Technol. 51, pp. 1147-1153, 2014.
Deshpande, G., et al., "Evidence-based guidelines for use of probiotics in preterm neonates", BMC Med 9, 92, pp. 13, 2011.
Drolia, R., et al., "Listeria adhesion protein induces intestinal epithelial barrier dysfunction for bacterial translocation", Cell Host & Microbe 23, pp. 470-484, 2018.
Edelson, B., et al., "CD8 alpha(+) dendritic cells are an obligate cellular entry point for productive infection by Listeria monocytogenes", Immunity 35, pp. 236-248, 2011.
Henderson, B., et al, "Chaperonin 60: a paradoxical, evolutionarily conserved protein family with multiple moonlighting functions", Biol. Rev. 88, pp. 955-987, 2013.
Hill, C., et al., "Expert consensus document: The International Scientific Association for Probiotics and Prebiotics consensus statement on the scope and appropriate use of the term probiotic", Nat. Rev. Gastroenterol. Hepatol., 11, pp. 506-514, 2014.

(Continued)

*Primary Examiner* — Sarvamangala Devi
(74) *Attorney, Agent, or Firm* — Purdue Research Foundation; Liang Zeng Yan

(57) ABSTRACT

The present application relates to an animal feed supplement for improving animal health and meat production comprising Next Generation Bioengineered Probiotics (NGBP). In some embodiments, the present application relates to a method for treating or preventing an inflammatory condition of a patient comprising the step of administering a therapeutically effective amount of Generation Bioengineered Probiotics (NGBP), together with one or more pharmaceutically acceptable carriers, diluents, and excipients, to the patient in need of relief from said inflammatory condition. In some other embodiments, the present invention relates to method for improving animal health and/or meat production comprising the step of adding an effective amount of Next Generation Bioengineered Probiotics (NGBP) to the feed of said animal.

6 Claims, 27 Drawing Sheets

Specification includes a Sequence Listing.

(56) References Cited

OTHER PUBLICATIONS

Jagadeesan, B, et al., "N-Terminal Gly224-Gly411 domain in Listeria adhesion protein interacts with host receptor Hsp60", PLoS One, 6,e20694, pp. 10, 2011.

Jagadeesan, B, et al., "LAP, an alcohol acetaldehyde dehydrogenase enzyme in Listeria promotes bacterial adhesion to enterocyte-like Caco-2 cells only in pathogenic species", Microbiology, 156, pp. 2782-2795, 2010.

Kim, H., et al., "Secreted Listeria adhesion protein (Lap) influences Lap-mediated Listeria monocytogenes paracellular translocation through epithelial barrier",Gut Pathog., 5, 16, pp. 11, 2013.

Koo, O., et al., "Recombinant probiotic expressing Listeria adhesion protein attenuates Listeria monocytogenes virulence in vitro", PLoS One, 7, e29277, pp. 14, 2012.

Mantis, N, et al.., "Secretory IgA's complex roles in immunity and mucosal homeostasis in the gut", Mucosal Immunol., 4, pp. 603-611, 2011.

Michon, C., et al., "Display of recombinant proteins at the surface of lactic acid bacteria: strategies and applications", Microb. Cell Factories, 15, 70, pp. 16, 2016.

Mishra, K., et al., "Genetic organization and molecular characterization of secA2 locus in *Listeria* species", Gene 489, pp. 76-85, 2011.

Pagnini, C., et al., "Probiotics promote gut health through stimulation of epithelial innate immunity", Proc. Natl. Acad. Sci. U. S. A. 107, pp. 454-459, 2010.

Sakai, F., et al., "Lactobacillus gasseri SBT2055 Induces TGF-beta Expression in Dendritic Cells and Activates TLR2 Signal to Produce IgA in the Small Intestine", PLoS One , 9, e105370, pp. 11, 2014.

Sanders, M., et al., "Probiotics and prebiotics: prospects for public health and nutritional recommendations", Annals New York Acad. Sci., 1309, pp. 19-29, 2014.

Wampler, J., et al., "Heat shock protein 60 acts as a receptor for the Listeria adhesion protein in Caco-2 cells", Infect. Immun., 72, pp. 931-936, 2004.

Xayarath, B., et al., "Optimizing the balance between host and environmental survival skills: lessons learned from Listeria monocytogenes", Future Microbiol., 7, pp. 839-852, 2012.

Yu, Q., et al., "Lactobacillus amylophilus D14 protects tight junction from enteropathogenic bacteria damage in Caco-2 cells", 95, pp. 5580-5587, 2012.

* cited by examiner

Antimicrobial activity
against L. m F4244

SEQUENCE LISTING

```
<160> NUMBER OF SEQ ID NOS: 2

<210> SEQ ID NO 1
<211> LENGTH: 866
<212> TYPE: PRT
<213> ORGANISM: Listeria monocytogenes
```

<400> SEQUENCE: 1

```
Met Ala Ile Lys Glu Asn Ala Ala Gln Glu Val Leu Glu Val Gln Lys
1               5                   10                  15

Val Ile Asp Arg Leu Ala Asp Asn Gly Gln Lys Ala Leu Lys Ala Phe
                20                  25                  30

Glu Ser Tyr Asn Gln Glu Gln Val Asp Asn Ile Val His Ala Met Ala
            35                  40                  45

Leu Ala Gly Leu Asp Gln His Met Pro Leu Ala Lys Leu Ala Val Glu
        50                  55                  60

Glu Thr Gly Arg Gly Leu Tyr Glu Asp Lys Cys Ile Lys Asn Ile Phe
65                  70                  75                  80

Ala Thr Glu Tyr Ile Trp Asn Asn Ile Lys Asn Asn Lys Thr Val Gly
                85                  90                  95

Val Ile Asn Glu Asp Val Gln Thr Gly Val Ile Glu Ile Ala Glu Pro
            100                 105                 110

Val Gly Val Val Ala Gly Val Thr Pro Val Thr Asn Pro Thr Ser Thr
        115                 120                 125

Thr Leu Phe Lys Ala Ile Ile Ala Ile Lys Thr Arg Asn Pro Ile Ile
    130                 135                 140

Phe Ala Phe His Pro Ser Ala Gln Arg Cys Ser Ser Ala Ala Ala Lys
145                 150                 155                 160

Val Val Tyr Asp Ala Ala Ile Ala Ala Gly Ala Pro Glu His Cys Ile
                165                 170                 175

Gln Trp Val Glu Lys Pro Ser Leu Glu Ala Thr Lys Gln Leu Met Asn
            180                 185                 190

His Asp Lys Val Ala Leu Val Leu Ala Thr Gly Gly Ala Gly Met Val
        195                 200                 205

Lys Ser Ala Tyr Ser Thr Gly Lys Pro Ala Leu Gly Val Gly Pro Gly
    210                 215                 220

Asn Val Pro Ala Tyr Ile Asp Lys Thr Ala Lys Ile Lys Arg Ser Val
225                 230                 235                 240

Asn Asp Ile Ile Leu Ser Lys Ser Phe Asp Gln Gly Met Ile Cys Ala
                245                 250                 255

Ser Glu Gln Ala Val Ile Val Asp Lys Glu Val Ala Lys Glu Val Lys
            260                 265                 270

Ala Glu Met Glu Ala Asn Lys Cys Tyr Phe Val Lys Gly Ala Glu Phe
        275                 280                 285

Lys Lys Leu Glu Ser Tyr Val Ile Asn Pro Lys Gly Thr Leu Asn
    290                 295                 300

Pro Asp Val Val Gly Lys Ser Pro Ala Trp Ile Ala Asn Gln Ala Gly
305                 310                 315                 320

Phe Lys Val Pro Glu Asp Thr Lys Ile Leu Val Ala Glu Ile Lys Gly
                325                 330                 335

Val Gly Asp Lys Tyr Pro Leu Ser His Glu Lys Leu Ser Pro Val Leu
            340                 345                 350

Ala Phe Ile Glu Ala Ala Asn Gln Ala Glu Ala Phe Asp Arg Cys Glu
        355                 360                 365

Glu Met Leu Val Tyr Gly Gly Leu Gly His Ser Ala Val Ile His Ser
    370                 375                 380

Thr Asp Lys Glu Val Gln Lys Ala Phe Gly Ile Arg Met Lys Ala Cys
385                 390                 395                 400

Arg Ile Ile Val Asn Ala Pro Ser Ala Gln Gly Gly Ile Gly Asp Ile
```

-continued

```
                405                 410                 415
Tyr Asn Gly Phe Ile Pro Ser Leu Thr Leu Gly Cys Gly Ser Tyr Gly
                    420                 425                 430

Lys Asn Ser Val Ser Gln Asn Val Ser Ala Thr Asn Leu Leu Asn Val
                    435                 440                 445

Lys Arg Ile Ala Asp Arg Arg Asn Asn Met Gln Trp Phe Lys Leu Pro
        450                 455                 460

Pro Lys Ile Phe Phe Glu Lys Tyr Ser Thr Gln Tyr Leu Gln Lys Met
465                 470                 475                 480

Glu Gly Val Glu Arg Val Phe Ile Val Thr Asp Pro Gly Met Gly Ser
                        485                 490                 495

Phe Lys Tyr Val Asp Val Val Ile Glu His Leu Lys Lys Arg Gly Asn
                    500                 505                 510

Asp Val Ala Tyr Gln Val Phe Ala Asp Val Glu Pro Asp Pro Ser Asp
                515                 520                 525

Val Thr Val Tyr Lys Gly Ala Glu Leu Met Lys Asp Phe Lys Pro Asp
            530                 535                 540

Thr Ile Ile Ala Leu Gly Gly Ser Ala Met Asp Ala Ala Lys Gly
545                 550                 555                 560

Met Trp Leu Phe Tyr Glu His Pro Glu Ala Ser Phe Phe Gly Leu Lys
                    565                 570                 575

Gln Lys Phe Leu Asp Ile Arg Lys Arg Thr Phe Lys Tyr Pro Lys Leu
                580                 585                 590

Gly Gly Lys Ala Lys Phe Val Ala Ile Pro Thr Thr Ser Gly Thr Gly
                595                 600                 605

Ser Glu Val Thr Pro Phe Ala Val Ile Thr Asp Lys Glu Asn Asn Ile
        610                 615                 620

Lys Tyr Pro Leu Ala Asp Tyr Glu Leu Thr Pro Asp Val Ala Ile Val
625                 630                 635                 640

Asp Ala Gln Tyr Val Thr Thr Val Pro Ala His Ile Thr Ala Asp Thr
                    645                 650                 655

Gly Met Asp Val Leu Thr His Ala Ile Glu Ser Tyr Val Ser Val Met
                660                 665                 670

Ala Ser Asp Tyr Thr Arg Gly Leu Ser Ile Arg Ala Ile Glu Leu Val
            675                 680                 685

Phe Glu Asn Leu Arg Glu Ser Val Leu Thr Gly Asp Pro Asp Ala Arg
        690                 695                 700

Glu Lys Met His Asn Ala Ser Ala Leu Ala Gly Met Ala Phe Ala Asn
705                 710                 715                 720

Ala Phe Leu Gly Ile Asn His Ser Leu Ala His Lys Ile Gly Pro Glu
                    725                 730                 735

Phe His Ile Pro His Gly Arg Ala Asn Ala Ile Leu Met Pro His Val
                740                 745                 750

Ile Arg Tyr Asn Ala Leu Lys Pro Lys Lys His Ala Leu Phe Pro Arg
            755                 760                 765

Tyr Glu Ser Phe Arg Ala Asp Glu Asp Tyr Ala Arg Ile Ser Arg Ile
        770                 775                 780

Ile Gly Phe Pro Ala Ala Thr Thr Glu Glu Gly Val Lys Ser Leu Val
785                 790                 795                 800

Asp Glu Ile Ile Lys Leu Gly Lys Asp Val Gly Ile Asp Met Ser Leu
                    805                 810                 815

Lys Gly Gln Asn Val Ala Lys Lys Asp Leu Asp Ala Val Val Asp Thr
                820                 825                 830
```

```
Leu Ala Asp Arg Ala Phe Met Asp Gln Cys Thr Thr Ala Asn Pro Lys
        835                 840                 845

Gln Pro Leu Val Ser Glu Leu Lys Glu Ile Tyr Leu Glu Ala Tyr Lys
    850                 855                 860

Gly Val
865

<210> SEQ ID NO 2
<211> LENGTH: 866
<212> TYPE: PRT
<213> ORGANISM: Listeria innocua

<400> SEQUENCE: 2

Met Ala Ile Lys Glu Asn Ala Ala Gln Glu Val Leu Glu Val Gln Lys
1               5                   10                  15

Val Ile Asp Arg Leu Ala Asp Asn Gly Gln Lys Ala Leu Lys Ala Phe
            20                  25                  30

Glu Ser Tyr Asn Gln Glu Gln Val Asp Asn Ile Val His Ala Met Ala
        35                  40                  45

Leu Ala Gly Leu Asp Gln His Met Pro Leu Ala Lys Leu Ala Val Glu
    50                  55                  60

Glu Thr Gly Arg Gly Leu Tyr Glu Asp Lys Cys Ile Lys Asn Ile Phe
65                  70                  75                  80

Ala Thr Glu Tyr Ile Trp Asn Asn Ile Lys Asn Asn Lys Thr Val Gly
                85                  90                  95

Val Ile Asn Glu Asp Thr Gln Thr Gly Val Ile Glu Ile Ala Glu Pro
            100                 105                 110

Val Gly Val Val Ala Gly Val Thr Pro Val Thr Asn Pro Thr Ser Thr
        115                 120                 125

Thr Leu Phe Lys Ala Ile Ile Ala Ile Lys Thr Arg Asn Pro Ile Ile
    130                 135                 140

Phe Ala Phe His Pro Ser Ala Gln Arg Cys Ser Ser Glu Ala Ala Lys
145                 150                 155                 160

Val Val Tyr Asp Ala Ala Val Ala Ala Gly Ala Pro Glu His Cys Ile
                165                 170                 175

Gln Trp Val Glu Lys Pro Ser Leu Glu Ala Thr Lys Gln Leu Met Asn
            180                 185                 190

His Asp Lys Val Ala Leu Val Leu Ala Thr Gly Gly Ala Gly Met Val
        195                 200                 205

Lys Ser Ala Tyr Ser Thr Gly Lys Pro Ala Leu Gly Val Gly Pro Gly
    210                 215                 220

Asn Val Pro Ala Tyr Ile Asp Lys Thr Ala Lys Ile Lys Arg Ser Val
225                 230                 235                 240

Asn Asp Ile Ile Leu Ser Lys Ser Phe Asp Gln Gly Met Ile Cys Ala
                245                 250                 255

Ser Glu Gln Ala Val Ile Val Asp Lys Glu Val Ala Lys Glu Val Lys
            260                 265                 270

Ala Glu Met Glu Ala Asn Lys Cys Tyr Phe Val Lys Gly Ala Glu Phe
        275                 280                 285

Lys Lys Leu Glu Ser Tyr Val Ile Asn Pro Glu Lys Gly Thr Leu Asn
    290                 295                 300

Pro Asp Val Val Gly Lys Ser Pro Ala Trp Ile Ala Asn Gln Ala Gly
305                 310                 315                 320

Phe Lys Val Pro Glu Asp Thr Lys Ile Leu Val Ala Glu Ile Lys Gly
```

-continued

```
            325                 330                 335
Val Gly Asp Lys Tyr Pro Leu Ser His Glu Lys Leu Ser Pro Val Leu
            340                 345                 350
Ala Phe Ile Glu Ala Ala Thr Gln Ala Glu Ala Phe Asp Arg Cys Glu
            355                 360                 365
Glu Met Leu Val Tyr Gly Gly Leu Gly His Ser Ala Val Ile His Ser
            370                 375                 380
Thr Asp Lys Glu Val Gln Lys Ala Phe Gly Ile Arg Met Lys Ala Cys
385                 390                 395                 400
Arg Ile Ile Val Asn Ala Pro Ser Ala Gln Gly Gly Ile Gly Asp Ile
                    405                 410                 415
Tyr Asn Gly Phe Ile Pro Ser Leu Thr Leu Gly Cys Gly Ser Tyr Gly
                    420                 425                 430
Lys Asn Ser Val Ser Gln Asn Val Ser Ala Thr Asn Leu Leu Asn Val
                    435                 440                 445
Lys Arg Ile Ala Asp Arg Arg Asn Asn Met Gln Trp Phe Lys Leu Pro
            450                 455                 460
Pro Lys Ile Phe Phe Glu Lys Tyr Ser Thr Gln Tyr Leu Gln Lys Met
465                 470                 475                 480
Glu Gly Val Glu Arg Val Phe Ile Val Thr Asp Pro Gly Met Val Gln
                    485                 490                 495
Phe Lys Tyr Val Asp Val Val Ile Glu His Leu Lys Lys Arg Gly Asn
                    500                 505                 510
Asp Val Ala Tyr Gln Val Phe Ala Asp Val Glu Pro Asp Pro Ser Asp
            515                 520                 525
Val Thr Val Tyr Lys Gly Ala Glu Leu Met Lys Asp Phe Lys Pro Asp
530                 535                 540
Thr Ile Ile Ala Leu Gly Gly Gly Ser Ala Met Asp Ala Ala Lys Gly
545                 550                 555                 560
Met Trp Leu Phe Tyr Glu His Pro Glu Ala Ser Phe Phe Gly Leu Lys
                    565                 570                 575
Gln Lys Phe Leu Asp Ile Arg Lys Arg Thr Phe Lys Tyr Pro Lys Leu
                    580                 585                 590
Gly Gly Lys Ala Lys Phe Val Ala Ile Pro Thr Thr Ser Gly Thr Gly
                    595                 600                 605
Ser Glu Val Thr Pro Phe Ala Val Ile Thr Asp Lys Glu Asn Asn Ile
            610                 615                 620
Lys Tyr Pro Leu Ala Asp Tyr Glu Leu Thr Pro Asp Val Ala Ile Val
625                 630                 635                 640
Asp Ala Gln Tyr Val Thr Thr Val Pro Ala His Ile Thr Ala Asp Thr
                    645                 650                 655
Gly Met Asp Val Leu Thr His Ala Ile Glu Ser Tyr Val Ser Val Met
                    660                 665                 670
Ala Ser Asp Tyr Thr Arg Gly Leu Ser Ile Arg Ala Ile Glu Leu Val
                    675                 680                 685
Phe Glu Asn Leu Arg Glu Ser Val Leu Thr Gly Asp Pro Asp Ala Arg
            690                 695                 700
Glu Lys Met His Asn Ala Ser Ala Leu Ala Gly Met Ala Phe Ala Asn
705                 710                 715                 720
Ala Phe Leu Gly Ile Asn His Ser Leu Ala His Lys Ile Gly Pro Glu
                    725                 730                 735
Phe His Ile Pro His Gly Arg Ala Asn Ala Ile Leu Met Pro His Val
                    740                 745                 750
```

-continued

```
Ile Arg Tyr Asn Ala Leu Lys Pro Lys Lys His Ala Leu Phe Pro Arg
        755                 760             765

Tyr Glu Ser Phe Arg Ala Asp Glu Asp Tyr Ala Arg Ile Ser Arg Ile
    770             775                 780

Ile Gly Phe Pro Ala Ala Thr Thr Glu Glu Gly Val Lys Ser Leu Val
785                 790                 795                 800

Asp Glu Ile Ile Lys Leu Gly Lys Asp Val Gly Ile Asp Met Ser Leu
                805                 810                 815

Lys Gly Gln Asn Val Ala Lys Lys Asp Leu Asp Ala Val Val Asp Thr
            820                 825                 830

Leu Ala Asp Arg Ala Phe Met Asp Gln Cys Thr Thr Ala Asn Pro Lys
        835                 840                 845

Gln Pro Leu Val Ser Glu Leu Lys Glu Ile Tyr Leu Glu Ala Tyr Lys
    850                 855                 860

Gly Val
865
```

BIOENGINEERED LACTOBACILLUS PROBIOTICS AND THE USES THEREOF

CROSS REFERENCE TO RELATED APPLICATIONS

This present patent application relates to and claims the priority benefit of U.S. Provisional Application Ser. No. 62/692,880, filed Jul. 2, 2018, the content of which is hereby incorporated herein by reference in its entirety

STATEMENT OF SEQUENCE LISTING

A computer-readable form (CRF) of the Sequence Listing is submitted concurrently with this application. The file, generated on Jun. 28, 2019, is entitled Sequence_Listing_68291-02_ST25_txt. Applicant states that the content of the computer-readable form is the same and the information recorded in computer readable form is identical to the written sequence listing.

TECHNICAL FIELD

The present application relates to a method for treating or preventing an inflammatory condition of a patient comprising the step of administering a therapeutically effective amount of Next Generation Bioengineered Probiotics (NGBP), together with one or more pharmaceutically acceptable carriers, diluents, and excipients, to the patient in need of relief from said inflammatory condition. In some other embodiments, the present invention relates to method for improving animal health and/or meat production comprising the step of adding an effective amount of Next Generation Bioengineered Probiotics (NGBP) to the feed of said animal.

BACKGROUND

This section introduces aspects that may help facilitate a better understanding of the disclosure. Accordingly, these statements are to be read in this light and are not to be understood as admissions about what is or is not prior art.

*Listeria monocytogenes* is an opportunistic human foodborne pathogen responsible for severe systemic infection (listeriosis), and abortion, stillbirth and premature birth in pregnant women, mortality in newborns, the elderly and other immunocompromised individuals. *L. monocytogenes* is well adapted to survive in the harsh environment of the gut (Sleator et al., 2009; Xayarath and Freitag, 2012). For the systemic spread, *L. monocytogenes* overcomes intestinal epithelial innate defense (Vance et al., 2009) and crosses the epithelial barrier. M cells overlying Peyer's patches (Marco et al., 1997; Pron et al., 1998) and Internalin A (InlA)-mediated pathways are considered common events for epithelial barrier crossing. InlA interacts with the host cell receptor E-cadherin for intracellular spread (Lecuit et al., 2001); however, it is located at the basolateral side of the epithelial adherens junction (AJ) and is inaccessible to luminal *L. monocytogenes*. It is proposed that E-cadherin exposed during villous epithelial cell extrusion (Pentecost et al., 2006) and mucus exocytosis (Nikitas et al., 2011), can interact with *Listeria* InlA. InlA/E-cadherin interaction is host species-specific. In mouse E-cadherin, proline is substituted by glutamic acid at the amino acid sequence position 16, thus InlA has low affinity for mouse or rat E-cadherin but has a strong interaction with the E-cadherin of permissive hosts, such as humans, gerbils and guinea pigs (Lecuit et al., 1999). Studies using transgenic mice expressing "humanized" E-cadherin (Disson et al., 2008) or murinized InlA (InlAm) (Bou Ghanem et al., 2012; Wollert et al., 2007) have indicated that *L. monocytogenes* may use alternate routes to translocate across the gut mucosa. We recently showed that *L. monocytogenes*, uses *Listeria* adhesion protein (LAP) to cross the intestinal epithelium by inducing epithelial barrier dysfunction by activating NF-kB and MLCK, in the absence of InlA, in epithelial cell and mouse models (Burkholder and Bhunia, 2010; Drolia et al., 2018). In mice, the bacterium is found in the epithelial lamina propria, mesenteric lymph nodes (MLN), blood, liver, spleen, and kidneys.

LAP (866 aa) is a housekeeping alcohol acetaldehyde dehydrogenase (Jagadeesan et al., 2010) in *L. monocytogenes* and displays moonlighting activity (See below and Sequence Listing for details). It interacts with the host cell Hsp60 (Wampler et al., 2004), a mammalian moonlight chaperone protein (Henderson et al., 2013), activates NF-kB leading to the proinflammatory cytokines release, myosin light chain kinase (MLCK) upregulation and epithelial tight junction protein mislocalization (claudin-1, occludin and E-cadherin), leading to a leaky epithelial barrier for bacterial passage (Drolia et al., 2018).

LAP protein sequence from *Listeria monocytogenes* (SEQ ID NO: 1):

```
  1 maikenaaqe vlevqkvidr ladngqkalk afesynqeqv dnivhamala gldqhmplak 61 laveetgrgl yedkciknif ateyiwnnik nnktvgvine dvqtgvieia epvgvvagvt 121 pvtnptsttl fkaiiaiktr npiifafhps aqrcssaaak vvydaaiaag apehciqwve 181 kpsleatkql mnhdkvalvl atggagmvks aystgkpalg vgpgnvpayi dktakikrsv 241 ndiilsksfd qgmicaseqa vivdkevake vkaemeankc yfvkgaefkk lesyvinpek 301 gtlnpdvvgk spawianqag fkvpedtkil vaeikgvgdk yplsheklsp vlafieaanq 361 aeafdrceem lvygglghsa vihstdkevq kafgirmkac riivnapsaq ggigdiyngf 421 ipsltlgcgs ygknsvsqnv satnllnvkr iadrrnnmqw fklppkiffe kystqylqkm 481 egvervfivt dpgmgsfkyv dvviehlkkr gndvayqvfa dvepdpsdvt vykgaelmkd 541 fkpdtiialg ggsamdaakg mwlfyehpea sffglkqkfl dirkrtfkyp klggkakfva 601 ipttsgtgse vtpfavitdk ennikyplad yeltpdvaiv daqyvttvpa hitadtgmdv 661 ithaiesyvs vmasdytrgl siraielvfe nlresvltgd pdarekmhna salagmafan
```

-continued

```
 721 aflginhsla hkigpefhip hgranailmp hvirynalkp kkhalfprye sfradedyar 781 isriigfpaa tteegvkslv deiiklgkdv gidmslkgqn vakkdldavv dtladrafmd 841 gcttanpkqp lvselkeiyl eaykgv LAP protein sequence from Listeria innocua (SEQ ID NO: 2):
   1 maikenaaqe vlevqkvidr ladngqkalk afesynqeqv dnivhamala gldqhmplak 61 laveetgrgl yedkciknif ateyiwnnik nnktvgvine dtqtgvieia epvgvvagvt 121 pvtnptsttl fkaiiaiktr npiifafhps aqrcsseaak vvydaavaag apehciqwve 181 kpsleatkql mnhdkvalvl atggagmvks aystgkpalg vgpgnvpayi dktakikrsv 241 ndiilsksfd qgmicaseqa vivdkevake vkaemeankc yfvkgaefkk lesyvinpek 301 gtlnpdvvgk spawianqag fkvpedtkil vaeikgvgdk yplsheklsp vlafieaatq 361 aeafdrceem lvygglghsa vihstdkevq kafgirmkac riivnapsaq ggigdiyngf 421 ipsltlgcgs ygknsvsqnv satnllnvkr iadrrnnmqw fklppkiffe kystgylqkm 481 egvervfivt dpgmvqfkyv dvviehlkkr gndvayqvfa dvepdpsdvt vykgaelmkd 541 fkpdtiialg ggsamdaakg mwlfyehpea sffglkqkfl dirkrtfkyp klggkakfva 601 ipttsgtgse vtpfavitdk ennikyplad yeltpdvaiv daqyvttvpa hitadtgmdv 661 lthaiesyvs vmasdytrgl siraielvfe nlresvltgd pdarekmhna salagmafan 721 aflginhsla hkigpefhip hgranailmp hvirynalkp kkhalfprye sfradedyar 781 isriigfpaa tteegvkslv deiiklgkdv gidmslkgqn vakkdldavv dtladrafmd 841 gcttanpkqp lvselkeiyl eaykgv
```

The gut mucosa represents the first site for the dynamic interaction of the enteric pathogens with the host (Finlay and Falkow, 1997). Therefore, averting this critical pathogen interaction step should help prevent extra-intestinal dissemination of pathogens and the consequent pathology. Live probiotics bacteria such as lactobacilli and bifidobacteria are known to colonize and proliferate in the intestine to improve intestinal microbial balance and protect the host from pathogens (Cross, 2002; Salminen et al., 2010). Among the different probiotic bacteria used, Lactobacillus species are common because they are natural inhabitants of the gut, modulate immune system (Amalaradjou and Bhunia, 2012; Sanders et al., 2014), and enhance epithelial innate defense and restore epithelial barrier function (Bron et al., 2017; Pagnini et al., 2010).

One of the major drawbacks of probiotics for prophylactic or therapeutic use is that the antimicrobial effect is inconsistent and may be strain specific (Hill et al., 2014) thus may have limited efficacy against a target pathogen. Therefore, there are unmet needs in using probiotic bacteria to prevent pathogen interactions with the host (Amalaradjou and Bhunia, 2013; Focareta et al., 2006; Michon et al., 2016; Mohamadzadeh et al., 2010).

BRIEF DESCRIPTION OF THE DRAWINGS

The above and other objects, features, and advantages of the present invention will become more apparent when taken in conjunction with the following description and drawings wherein identical reference numerals have been used, where possible, to designate identical features that are common to the figures, and wherein:

FIG. 1A shows amino acid sequence comparison of LAP from L. monocytogenes (SEQ ID NO: 1) and L. innocua (S comycin were used as positive controls showing a zone of inhibition.

FIG. 4A is a schematics showing animal experiment protocol: mice (female A/J mice, 6 weeks old) were fed probiotics for 10 days, and then challenged with *L. monocytogenes* F4244 ($8.8 \times 10^8$ cfu/animal). FIG. 4B Mice body weight analysis over 12-days period during probiotic feeding and challenge with *L. monocytogenes* (Lm) at time points 0, 5, 10, and 12 days. FIGS. 4C-4D show analysis of bioengineered Lbc colonization in the mouse gut: (4C) Total lactic acid bacterial counts in animals that were fed with different bioengineered Lbc or controls on MRS agar plate and vancomycin resistant LbcWT, LbcLAP$^{Lin}$; LbcLAP$^{Lm}$ (4D) in the intestine and feces during 10 days of feeding. Wild type and bioengineered probiotic counts in the intestine and fecal samples of mice from day 13. MRS containing vancomycin (300 μg/ml) was used to isolate LbcWT (n=15 mice) and MRS containing erythromycin (2 μg/ml) was used to enumerate bioengineered probiotics, LbcLAP$^{Lin}$ (n=15) and LbcLAP$^{Lm}$ (n=15). As expected, no antibiotic resistant probiotics were detected from control animals or control animals that received *L. monocytogenes* (Lm) only.

FIGS. 4E-4K depict mice experiments showing bioengineered probiotic mediated prevention of *L. monocytogenes* infection. *L. monocytogenes* counts in probiotic fed mice in (4E) liver, (4F) spleen, (4G) MLN, (4H) kidney, (4I) blood, (4J) intestine, and (4K) feces after 24 h or 48 h post infection. (n=6-10 mice). Each animal was represented by a dot in the plot (n=3-10 mice per group). Horizontal dotted lines indicate detection limit of the assay. Treatments were, wild type *L. casei* (LbcWT), bioengineered *L. casei* expressing LAP of *L. monocytogenes* (LbcLAP$^{Lm}$) and *L. innocua* (LbcLAP$^{Lin}$). No background *Listeria* was detected from mice that received only the probiotics (LbcWT, LbcLAPLm, LbcLAPLin) or no probiotics at all. Data were analyzed by Man Whitney test using GraphPad Prism 6. (*, P=0.05, , P=0.001; *, P=0.0001; ns=not significant).

FIGS. 6A-6B show epithelial permeability in Caco-2 cell monolayers in transwell insert using 4 kDa FITC-Dextran (FD4) (a) movement from apical to basolateral side and Transepithelial electrical resistance (TEER) (b) after treatment with Control, *L. monocytogenes* (Lm), No Lbc+Lm, LbcWT, LbcWT+Lm, LbcLAP$^{Lin}$, LbcLAP$^{Lm}$+Lm, LbcLAP$^{Lin}$, LbcLAP$^{Lin}$+Lm. FIGS. 6A-6B show intestinal epithelial permeability assessment by measuring FD4 levels in serum (6C) and urine (6D) in probiotic fed mice from FIGS. 4A-4K. Treatments were, control, No Lbc+Lm, LbcWT, LbcWT+Lm, LbcLAP$^{Lm}$, LbcLAP$^{Lm}$+Lm, LbcLAP$^{Lin}$, LbcLAP$^{Lin}$+Lm. Bioengineered probiotics significantly reduced the FD4 translocation compared to the LbcWT or Lm alone. (***, P<0.0001; *, P<0.05, ns, not significant).

FIG. 7A shows Western blot showing tight junction (ZO-1, occludin, claudin-1) and adherence junction protein (E-cadherin) levels in cells after treatment with *L. monocytogenes* or probiotic bacteria followed by *L. monocytogenes* challenge. Confirmation of cell-junction protein mislocalization by confocal immunofluorescence microscopy in Caco-2 cells (7B) and in mouse ileal tissue section (7C). White arrows (presence) and yellow (absence or mislocalization) pointing to the cell junction proteins.

Figure 1A:
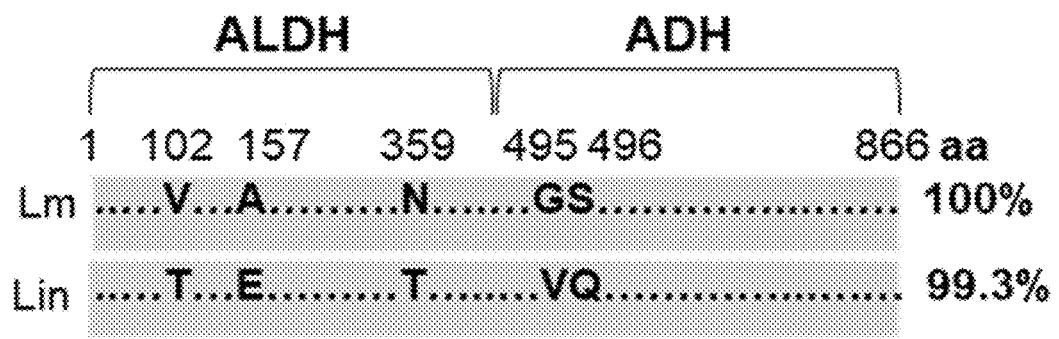
FIGS. 1A-1D demonstrates that Listeria Adhesion Protein (LAP) from Listeria innocua restored adhesion and translocation ability of the lap-deficient L. monocytogenes (KB208) to enterocytes.
Figure 1B:
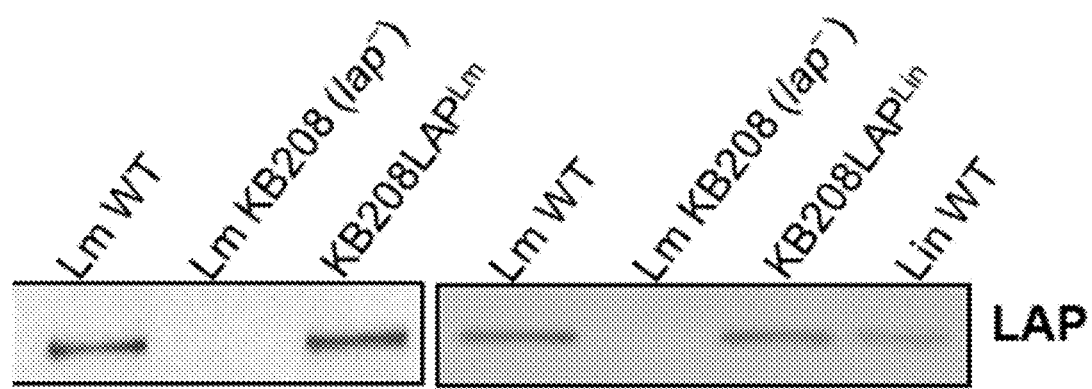
Figure 1C:
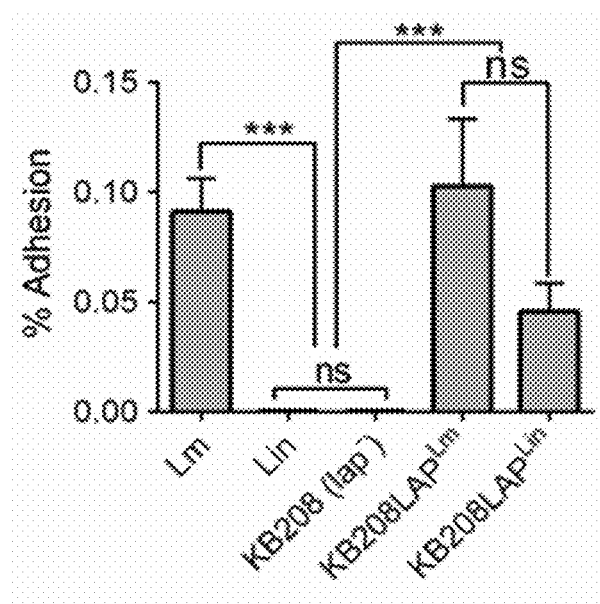
Figure 1D:
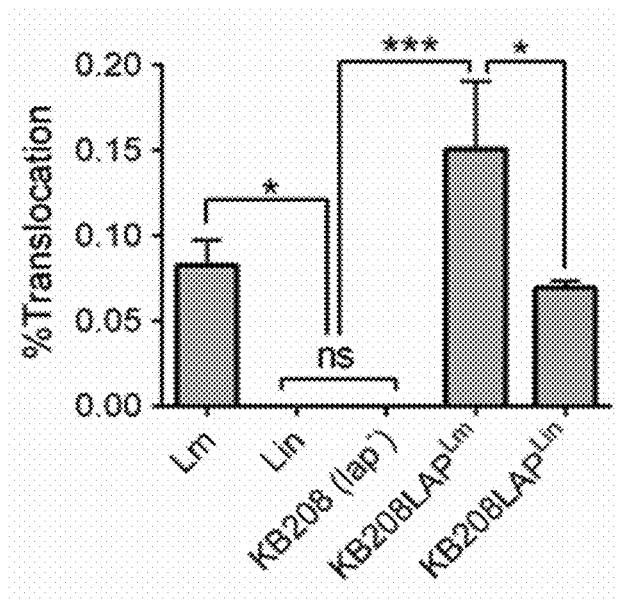

expressing the LAP protein (LbcLAP$^{Lin}$) showed significantly (**P<0.01, Kaplan-Meier log-rank test) higher survival compared to that of LbcWT.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In the present disclosure the term "about" can allow for a degree of variability in a value or range, for example, within 10%, within 5%, or within 1% of a stated value or of a stated limit of a range.

In the present disclosure the term "substantially" can allow for a degree of variability in a value or range, for example, within 70%, within 80%, within 90%, within 95%, or within 99% of a stated value or of a stated limit of a range.

The term "patient" includes human and non-human animals such as companion animals (dogs and cats and the like) and livestock animals. Livestock animals are animals raised for food production. The patient to be treated is preferably a mammal, in particular a human being.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other nontoxic compatible substances employed in pharmaceutical formulations.

As used herein, the term "administering" includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically acceptable carriers, adjuvants, and vehicles.

It is to be understood that the total daily usage of the compounds and compositions described herein may be decided by the attending physician within the scope of sound medical judgment. The specific therapeutically effective dose level for any particular patient will depend upon a variety of factors, including the disorder being treated and the severity of the disorder; activity of the specific compound employed; the specific composition employed; the age, body weight, general health, gender, and diet of the patient: the time of administration, and rate of excretion of the specific compound employed, the duration of the treatment, the drugs used in combination or coincidentally with the specific compound employed; and like factors well known to the researcher, veterinarian, medical doctor or other clinician of ordinary skill.

Depending upon the route of administration, a wide range of permissible dosages are contemplated herein, including doses falling in the range from about 1 µg/kg to about 1 g/kg. The dosage may be single or divided, and may be administered according to a wide variety of dosing protocols, including q.d., b.i.d., t.i.d., or even every other day, once a week, once a month, and the like. In each case the therapeutically effective amount described herein corresponds to the instance of administration, or alternatively to the total daily, weekly, or monthly dose.

As used herein, the term "therapeutically effective amount" refers to that amount of active compound or pharmaceutical agent that elicits the biological or medicinal response in a tissue system, animal or human that is being sought by a researcher, veterinarian, medical doctor or other clinicians, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment.

As used herein, the term "therapeutically effective amount" refers to the amount to be administered to a patient, and may be based on body surface area, patient weight, and/or patient condition. In addition, it is appreciated that there is an interrelationship of dosages determined for humans and those dosages determined for animals, including test animals (illustratively based on milligrams per meter squared of body surface) as described by Freireich, E. J., et al., Cancer Chemother. Rep. 1966, 50 (4), 219, the disclosure of which is incorporated herein by reference. Body surface area may be approximately determined from patient height and weight (see, e.g., Scientific Tables, Geigy Pharmaceuticals, Ardley, N.Y., pages 537-538 (1970)). It is appreciated that effective doses may also vary depending on the route of administration, optional excipient usage, and the possibility of co-usage of the compound with other conventional and non-conventional therapeutic treatments, including other anti-tumor agents, radiation therapy, and the like.

As used herein, a patient may be an animal or a human being.

Probiotic:

The International Scientific Association of Probiotics and Prebiotics (ISAPP) in 2014 defined probiotics as "live microorganisms that, when administered in adequate amounts, confer a health benefit on the host" (Hill et al. *Nat Rev Gastroenterol Hepatol* 11.8 (2014): 506-514).

Next Generation Probiotics (NGPs):

Conform to the normal definition of a probiotic, when administered in adequate amounts, confer a health benefit on the host and is applicable to the prevention, treatment, or cure of a disease or condition of human beings (O'Tolle et al. *Nature microbiology* 2.5 (2017): 17057; Langella et al. *Frontiers in Microbiology* 10 (2019): 1047).

Next Generation Bioengineered Probiotics (NGBPs):

Conform to the normal definition of NGPs, but are genetically modified probiotic strains to exclusively target a specific pathogen, toxin or disease conditions and can be used for a therapeutic purpose (Amalaradjou et al *Bioengineered* 4.6 (2013): 379-387; Hill et al. *Nat Rev Gastroenterol Hepatol* 11.8 (2014): 506-514).

In some illustrative embodiments, the present invention relates to a method for improving animal health and/or meat production comprising the step of adding an effective amount of Next Generation Bioengineered Probiotics (NGBP) to the feed of said animal.

In some illustrative embodiments, the present invention relates to a method for improving animal health and/or meat production comprising the step of adding an effective amount of Next Generation Bioengineered Probiotics (NGBP) to the feed of said animal as disclosed herein, wherein said animal is selected from the group consisting of pig, sheep, goat, chicken, turkey, cat, dog, and cattle.

In some illustrative embodiments, the present invention relates to a method for improving animal health and/or meat production comprising the step of adding an effective amount of Next Generation Bioengineered Probiotics (NGBP) to the feed of said animal as disclosed herein, wherein said NGBP is a reengineered bacteria expressing *Listeria* adhesion protein (LAP).

In some illustrative embodiments, the present invention relates to a method for improving animal health and/or meat production comprising the step of adding an effective amount of Next Generation Bioengineered Probiotics (NGBP) to the feed of said animal as disclosed herein, wherein said NGBP is a lyophilized product.

In some other illustrative embodiments, the present invention relates to an animal feed supplement for improving animal health and meat production compromising Next Generation Bioengineered Probiotics (NGBP).

In some illustrative embodiments, the present invention relates to an animal feed supplement for improving animal health and meat production compromising Next Generation Bioengineered Probiotics (NGBP) as disclosed herein, wherein said NGBP is a reengineered bacteria expressing *Listeria* adhesion protein (LAP).

In some illustrative embodiments, the present invention relates to an animal feed supplement for improving animal health and meat production compromising Next Generation Bioengineered Probiotics (NGBP) as disclosed herein, wherein said animal feed supplement is a lyophilized product.

In some illustrative embodiments, the present invention relates to an animal feed supplement for improving animal health and meat production compromising Next Generation Bioengineered Probiotics (NGBP) as disclosed herein, wherein said animal is selected from the group consisting of pig, sheep, goat, chicken, turkey, cat, dog, and cattle.

Yet in some other embodiments, the present invention relates to a method to reduce or eliminate antibiotics used in an animal feed for improving animal health and meat production comprising the step of adding an effective amount of Next Generation Bioengineered Probiotics (NGBP) to the feed.

In some other embodiments, the present invention relates to a method to reduce or eliminate antibiotics used in an animal feed for improving animal health and meat production comprising the step of adding an effective amount of Next Generation Bioengineered Probiotics (NGBP) to the feed as disclosed herein, wherein said animal is selected from the group consisting of pig, sheep, goat, chicken, turkey, cat, dog, and cattle.

In some other embodiments, the present invention relates to a method to reduce or eliminate antibiotics used in an animal feed for improving animal health and meat production comprising the step of adding an effective amount of Next Generation Bioengineered Probiotics (NGBP) to the feed as disclosed herein, wherein said NGBP is a reengineered bacteria expressing *Listeria* adhesion protein (LAP).

In some other embodiments, the present invention relates to a method for treating or preventing an inflammatory condition of a patient comprising the step of administering a therapeutically effective amount of Next Generation Bioengineered Probiotics (NGBP), together with one or more pharmaceutically acceptable carriers, diluents, and excipients, to the patient in need of relief from said inflammatory condition.

In some other embodiments, the present invention relates to a method for treating or preventing an inflammatory condition of a patient comprising the step of administering a therapeutically effective amount of Next Generation Bioengineered Probiotics (NGBP), together with one or more pharmaceutically acceptable carriers, diluents, and excipients, to the patient in need of relief from said inflammatory condition as disclosed herein, wherein said inflammatory condition comprises Crohn's disease (CD), inflammatory Bowel Disease (IBD), and ulcerative colitis (US), wherein intestinal mucosal cells express a high level of Hsp60.

In some other embodiments, the present invention relates to a method for treating or preventing an inflammatory condition of a patient comprising the step of administering a therapeutically effective amount of Next Generation Bioengineered Probiotics (NGBP), together with one or more pharmaceutically acceptable carriers, diluents, and excipients, to the patient in need of relief from said inflammatory condition as disclosed herein, wherein said NGBP is a reengineered bacteria expressing *Listeria* adhesion protein (LAP).

In some other embodiments, the present invention relates to a method for treating or preventing an inflammatory condition of a patient comprising the step of administering a therapeutically effective amount of Next Generation Bioengineered Probiotics (NGBP), together with one or more pharmaceutically acceptable carriers, diluents, and excipients, to the patient in need of relief from said inflammatory condition as disclosed herein, wherein NGBP is administered orally.

Here, we investigated whether a probiotic bacterium expressing LAP can competitively exclude pathogen interaction on the host epithelial cell, thereby preventing listeriosis in a high-risk population in the background of the probiotic's natural beneficial attributes. In a previous study, as a proof of concept, we showed that LAP of *L. monocytogenes* expressed on *Lactobacillus paracasei* was able to reduce *L. monocytogenes* interaction with the enterocyte-like Caco-2 cell model, however, its effectiveness in an animal model and the host response are unknown. Here, we investigated if the LAP especially from a non-pathogenic *Listeria* (*L. innocua*), can be used on a more commonly used probiotic strain, *Lactobacillus casei* to competitively exclude pathogen interaction in a mouse model. Here, we show that *Lactobacillus casei* expressing LAP from a non-pathogenic bacterium, *L. innocua*, supplied to mice (A/J) in drinking water for 10 days, and subsequently challenged with *L. monocytogenes* was able to protect mice from listeriosis. This probiotic also significantly reduced *L. monocytogenes* burden in the extra-intestinal tissues, modulated proinflammatory cytokines levels, dampened NF-kB activity, and improved epithelial innate defense and barrier function to protect mice from the infection.

Potential benefits of "Next Generation Bioengineered Probiotics (NGBP)" expressing *Listeria* adhesion protein (LAP) from a nonpathogenic *Listeria* (*L. innocua*) that binds to a mammalian cell receptor, Hsp60 on human health:

Probiotics, in general, have positive effects on the gut via their expression of antimicrobial agents, their colonization of niches that might otherwise be occupied by pathogenic bacteria, modulating cytokine levels, and their effects on the gut immune system. Overall, these effects are anti-inflammatory.

Figure 2A:
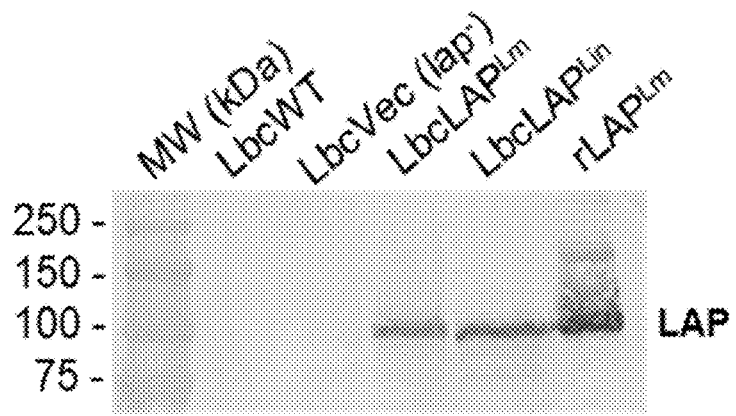
Figure 2B:
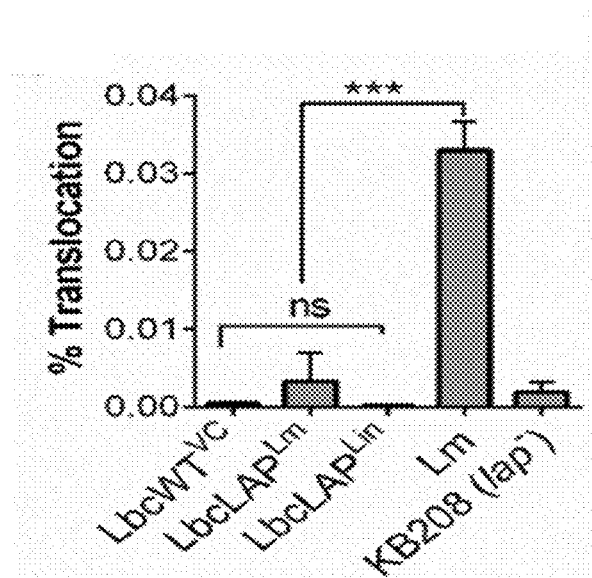
Figure 2C:
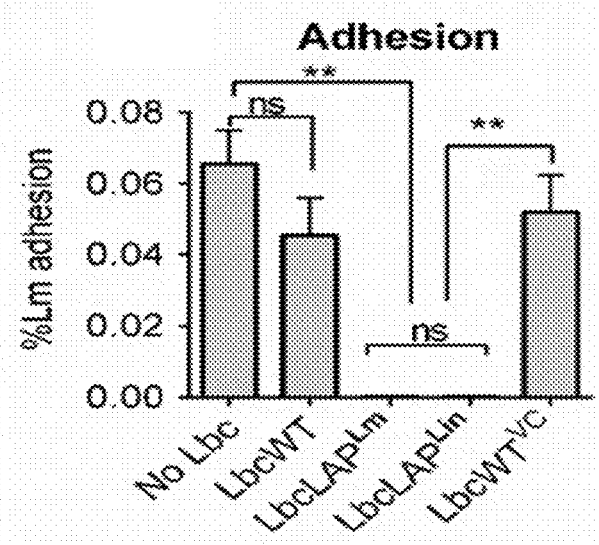
Figure 2D:
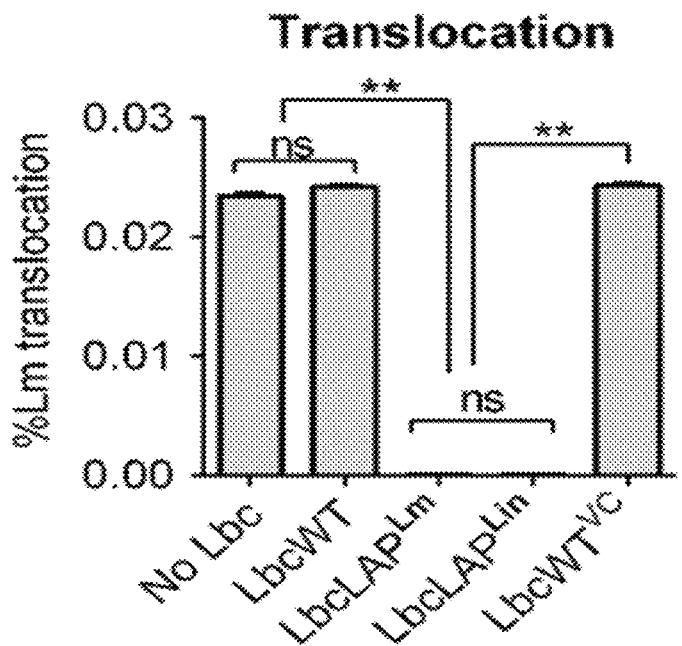
Figure 2E:
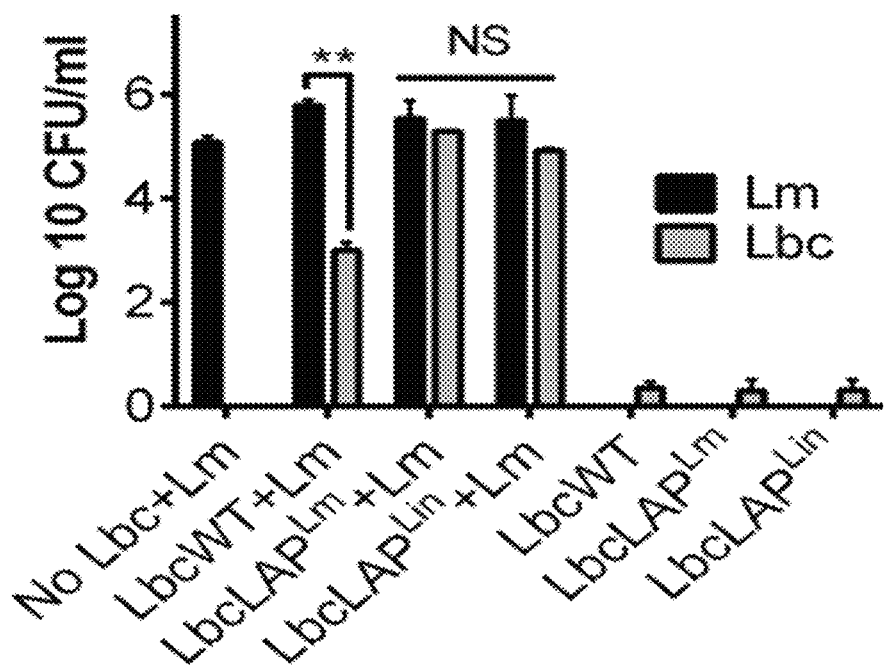
Figure 2F:
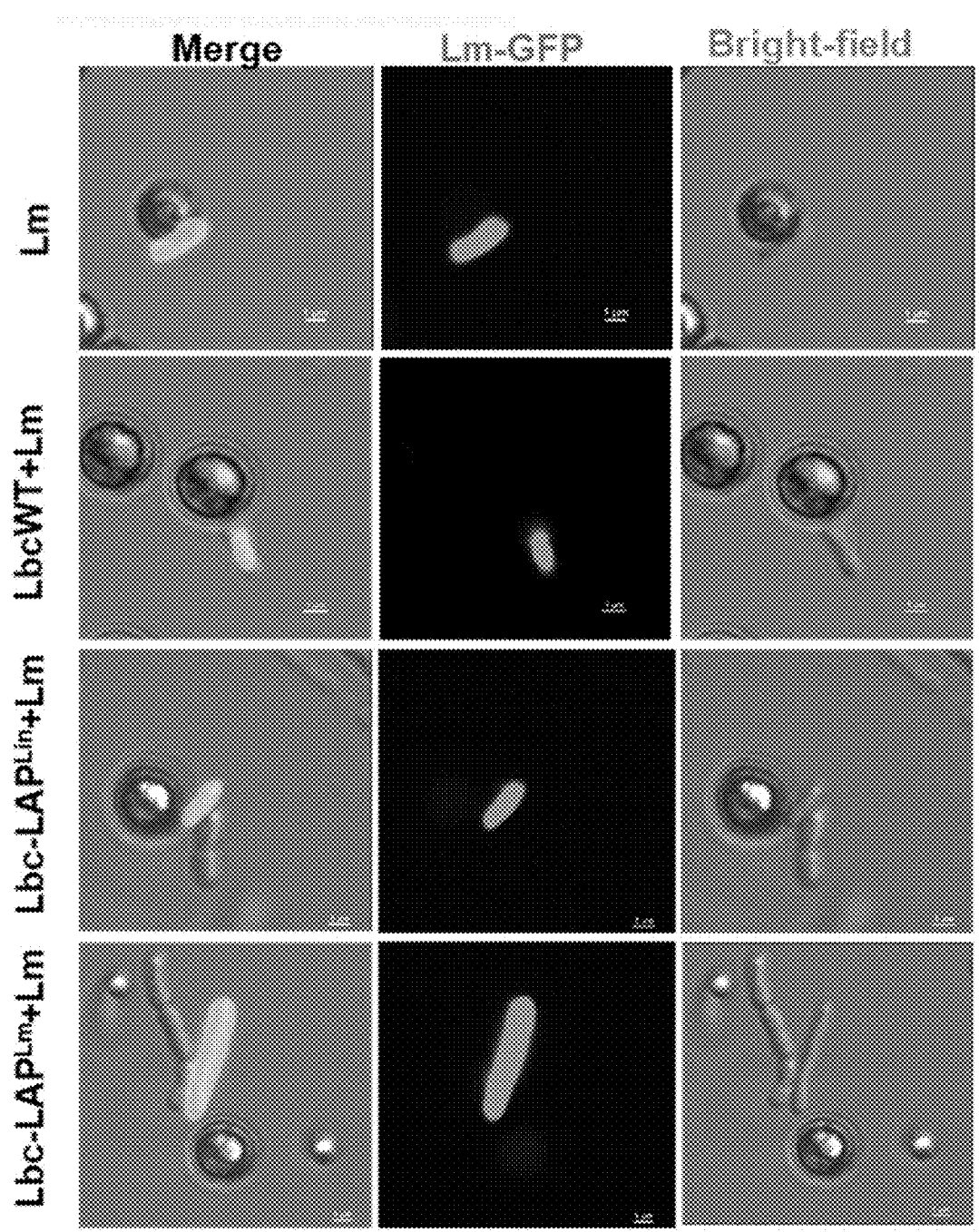
Figure 3A:
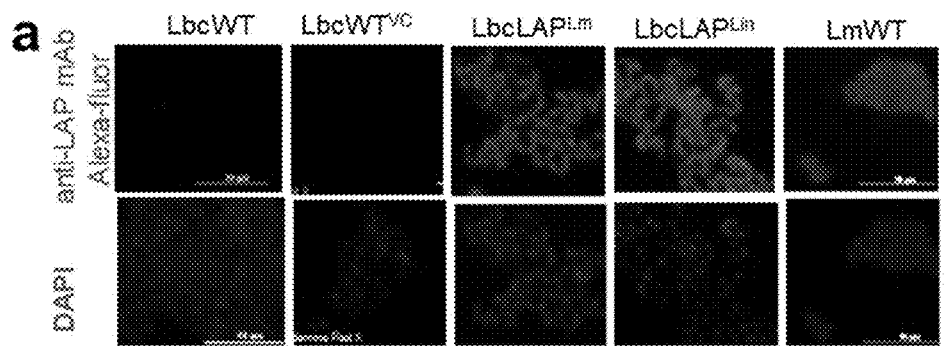
FIGS. 3D-3F show survival of bioengineered *L. casei* (LbcLAP$^{Lin}$; LbcLAP$^{Lm}$) and LbcWT in simulated gastric fluid (SGF) (3D), simulated intestinal fluid I (SGF-I) (3E), and simulated intestinal fluid II (SGF-II) (3F).
FIG. 3G shows the light microscopic photographs showing the live and dead stained bioengineered LbcLAP$^{Lin}$ strain using cFDA-SE (carboxyfluorescein diacetate succinimidyl ester) and PI (propidium iodide) after exposure to simulated gastric fluid (SGF) and simulated intestinal fluid (SIF) for 2.5 h.
FIG. 3H confirms LAP expression in bioengineered probiotics (LbcLAP$^{Lin}$; LbcLAP$^{Lm}$), but absent in LbcWT when grown SIF-I.
Figure 3B:
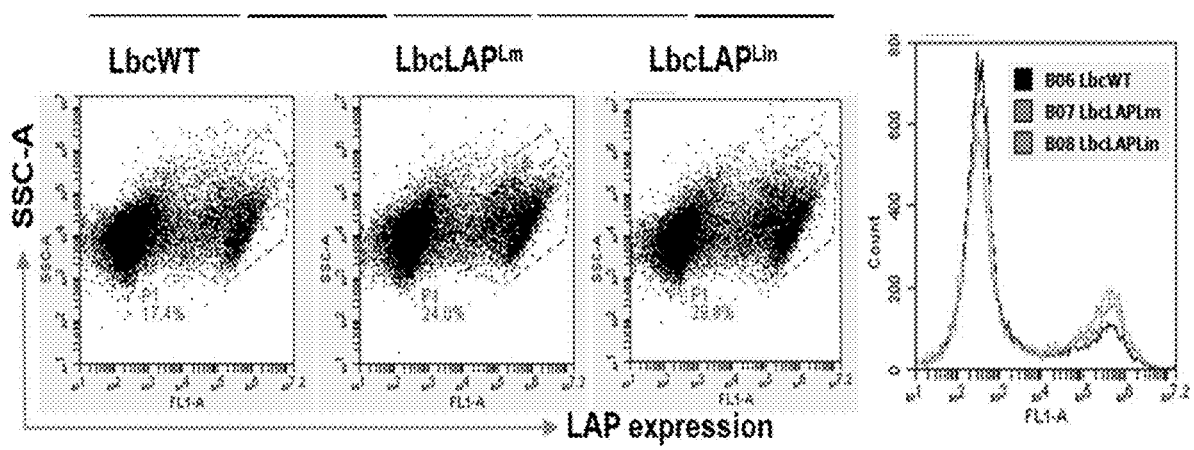
Figure 3C:
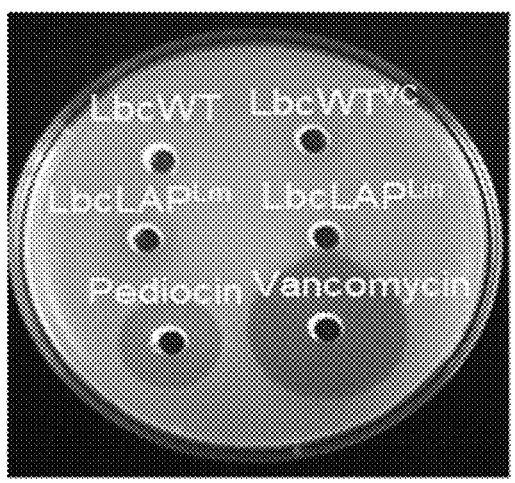

A key 'receptor' for LAP is Hsp60, which is involved in both chaperoning and immune system function. At low levels, Hsp60 is anti-inflammatory, but at higher concentrations, it can take on pro-inflammatory roles.
- In many chronic inflammatory disease conditions such as Crohn's Disease (CD), Inflammatory Bowel Disease (IBD), and Ulcerative Colitis (UC), intestinal mucosal cells express a high level of Hsp60.
- Inflammatory disease disrupts gut barrier function thus gut becomes leaky allowing luminal microbes and endotoxins to enter blood circulation. NGBP through its interaction with Hsp60 can maintain epithelial barrier integrity thus prevent endotoxin from crossing gut epithelial barrier—thus maintain a gut health.
- Targeting innate or exogenous microbe-induced Hsp60 in mucosal cells with LAP-expressing NGBP may usefully repress inflammatory processes in the gut, as well as some types of infectious processes.
  - LAP-expressing NGBP localization and persistence in the gut is also enhanced because of their interaction with mucosal Hsp60.
- LAP-expressing NGBP also prevents *Listeria monocytogenes* colonization and systemic spread and provides protection against severe disease as confirmed in a mouse model.
- The LAP-expressing NGBP, by virtue of its Hsp60 targeting, uniquely addresses stabilization of the gut to inflammatory and microbiological challenges, as demonstrated in mouse studies.

On the other hand, meat animals such as swine encounters various stressful situations throughout their life. Early in life, weaning, food and water deprivation during transportation and heat are common stressors. Stressors can reduce feed intake, exert inflammatory response, and based on the severity, the stressors can affect gut health by disrupting epithelial barrier function thus making the gut a "leaky gut." A leaky gut permits increased leakage of luminal commensal bacterial endotoxins (LPS, peptidoglycan) or pathogens into the submucosal location resulting in increased inflammatory cytokine secretion (TNF$\alpha$, IL-6, TGF$\beta$, IL-8, etc) from intestinal epithelial cells and immune cells. Nutritional deprivation also severely impairs gut function including reduced mucus secretion, and shortened villi height and crypt depth. Thermal stress can damage the intestinal epithelium and elicit enterocyte membrane damage or death alters villus/crypt structure, impairs tight junction integrity and increases endotoxin levels in the blood. Epithelial cells exposed to stress have shown increased Hsp60 expression. Altogether, stressors affect growth performance and make animals susceptible to various infectious agents with a huge financial loss to the farmers. Antibiotics are often used in feed to control infections and to enhance growth performance; however, concerns for the onset of antibiotics resistance require an alternative approach.

Potential benefits of "Next Generation Bioengineered Probiotics (NGBP)" expressing *Listeria* adhesion protein (LAP) from a nonpathogenic *Listeria* (*L. innocua*) that binds to a mammalian cell receptor, Hsp60 on animal health:

- LAP-expressing NGBP can be used as a feed supplement to help improve gut health by increased colonization of probiotics by specifically interacting with mucosal Hsp60.
- NGBP can improve gut barrier function by exerting anti-inflammatory response
- Generally, probiotics are most effective when normal intestinal homeostasis is perturbed, particularly during periods of stress. Here NGBP with increased interaction with stressed mucosal cells would be very effective in maintaining intestinal homeostasis.
- Because of anti-inflammatory and anti-microbial response of NGBP, antibiotics use in feed can be reduced or eliminated.
- NGBP mediated improved gut health can also enhance growth performance and body weight.

The present invention may be better understood in light of the following non-limiting compound examples and method examples.

LAP from *Listeria innocua* (Non-Pathogen) Restored Adhesion and Epithelial Translocation Ability of the Lap-Deficient *L. monocytogenes* Strain to Enterocytes.

LAP from pathogenic *Listeria* (i.e., *L. monocytogenes*) shares 99.3% amino acid sequence with the LAP from a nonpathogenic *Listeria* (*L. innocua*) (Bailey et al., 2017; Jagadeesan et al., 2010) (FIG. 1A). It is proposed that extracellular secreted LAP in the pathogen, re-associates on the surface of the bacterium to aid in bacterial adhesion and translocation across the epithelial barrier (Jagadeesan et al., 2010). However, in *L. innocua*, LAP does not aid in adhesion to the intestinal epithelial cells possibly due to a defect in re-association of the protein on the surface of this bacterium (Burkholder et al., 2009; Jagadeesan et al., 2010). Here, we show that the lap of *L. innocua* strain F4248, cloned and expressed in the lap-deficient *L. monocytogenes* mutant strain (KB208LAP$^{Lin}$) (FIG. 1B) restored its adhesion to (FIG. 1D), and translocation across (FIG. 1E) the Caco-2 cell monolayers at levels similar to that of a lap-mutant strain expressing LAP of *L. monocytogenes* (KB208LAP$^{Lm}$), or the *L. monocytogenes* WT (F4244, serovar 4b). These data provide a strong indication that LAP from *L. innocua* has similar adhesion characteristics as the *L. monocytogenes* WT strain.

*Lactobacillus casei* Expressing LAP of *L. innocua* Reduced *L. monocytogenes* Infection in Caco-2 Cell and a Mouse Model.

The lap ORF (2.6 kb) from both *L. innocua* and *L. monocytogenes* was cloned separately into a *Lactobacillus* expression vector, pLP401T (Koo et al., 2012; Maassen et al., 1999), and the proteins were expressed on the wild-type probiotic *Lactobacillus casei* ATCC344 (LbcWT) and designated LbcLAP$^{Lin}$ and LbcLAP$^{Lm}$, respectively. LAP expression in both bioengineered *Lactobacillus* probiotics (BLP) strains was confirmed by immunoblotting (FIG. 2A), immunofluorescence staining and flow cytometry (FIGS. 3A, 3B) using anti-LAP mAb. LAP induces epithelial barrier dysfunction and promotes *L. monocytogenes* translocation across the mucosal membrane (Drolia et al., 2018); therefore, the BLP strains (LbcLAP$^{Lin}$ and LbcLAP$^{Lm}$) were tested in the in vitro transwell setup for their ability to traverse epithelial-barrier. Interestingly, none of the BLP strains showed any significant translocation while the *L. monocytogenes* WT strain as a control showed a significantly very high translocation (FIG. 2B). These data indicate probiotics' natural ability to maintain the epithelial barrier integrity possibly supersedes LAP-induced epithelial barrier dysfunction (Bron et al., 2017; Pagnini et al., 2010).

Next, we examined if these BLP strains could prevent *L. monocytogenes* interaction with the epithelial cells. BLP strain pre-exposed to Caco-2 cell line significantly lowered *L. monocytogenes* adhesion to (FIG. 2C) and translocation across the epithelial monolayer in transwell (FIG. 2D), while the LbcWT pre-exposure did not show any significant reduction in *L. monocytogenes* translocation. A plasmid-vector control strain without the lap insert (LbcWT$^{VC}$) produced similar results as LbcWT, thus dismissing any extraneous anti-listerial effects that could be contributed by the virgin plasmid. In addition, none of the probiotic strains produced any anti-listerial compounds analyzed by the agar well-diffusion assay (FIG. 3C) thus ruled out the involvement of any bacteriocin-like inhibitory substance. Next, we hypothesized that the BLP-mediated inhibition of *L. monocytogenes* interaction with the epithelial cells could be facilitated by direct binding of *L. monocytogenes* cells to BLP since BLP expresses LAP, and the LAP has a natural affinity towards its own surface (Burkholder et al., 2009; Jagadeesan et al., 2010). Therefore, we examined the interaction between BLP and *L. monocytogenes* cells, if any, in a suspension culture. Using a *Listeria*-specific immunomagnetic bead (IMB; Invitrogen) capture system, we showed that *L. monocytogenes* WT bound strongly with the BLP cells, while a significantly reduced level with the LbcWT suggesting that BLP interaction (aggregation) with *L. monocytogenes* was mediated by the LAP (FIG. 2E). Collectively, these data suggest that pre-occupation of the epithelial surface by LAP-expressing BLP can competitively exclude *L. monocytogenes* from interacting with the epithelial cells.

Figure 3D:
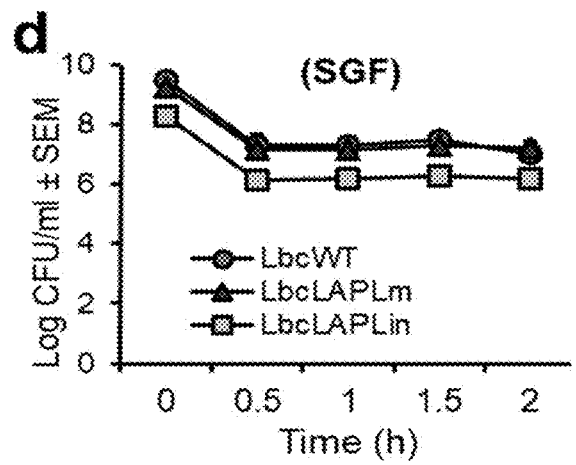
Figure 3E:
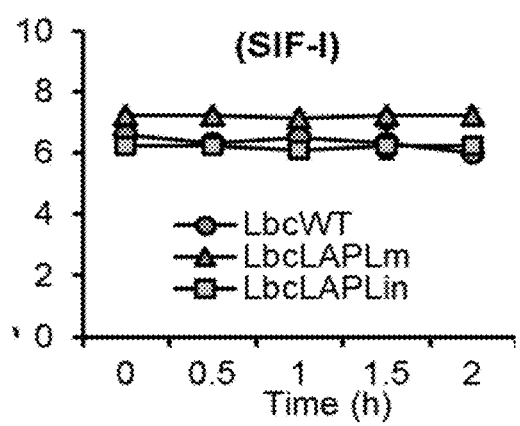
Figure 3F:
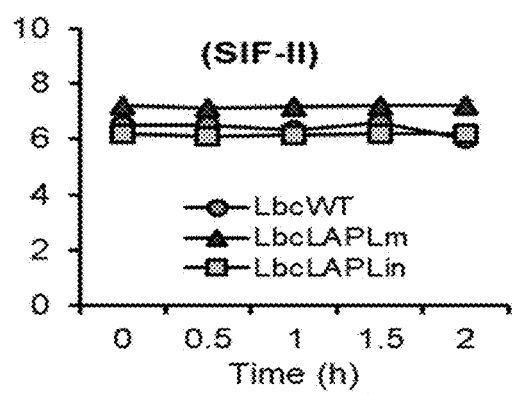
Figure 3G:
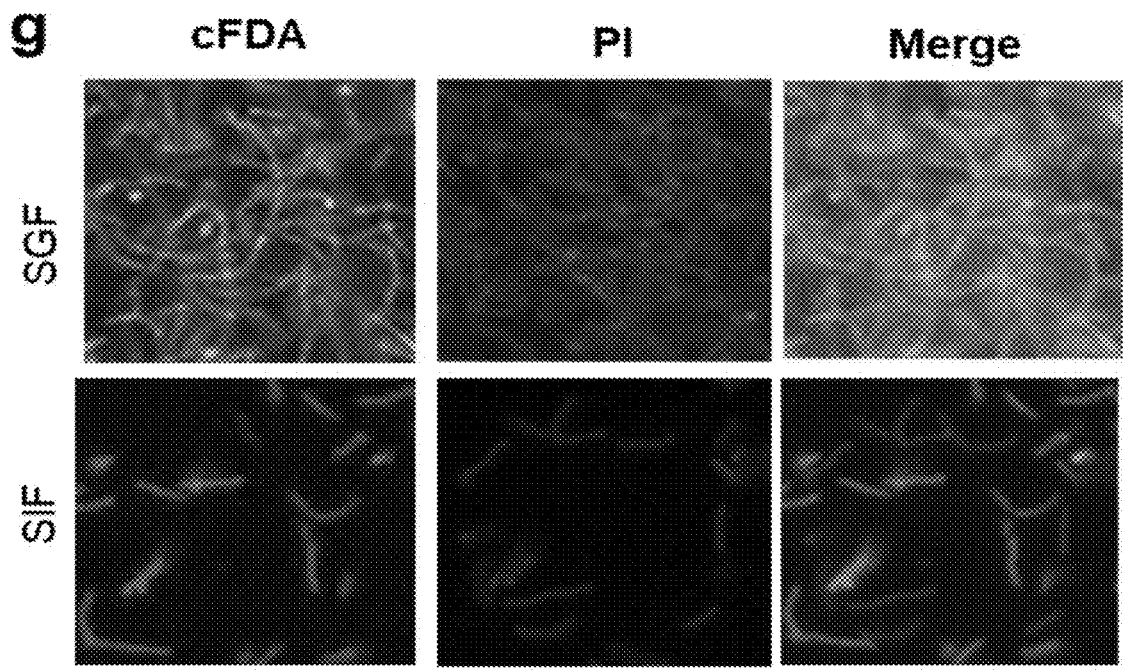
Figure 3H:
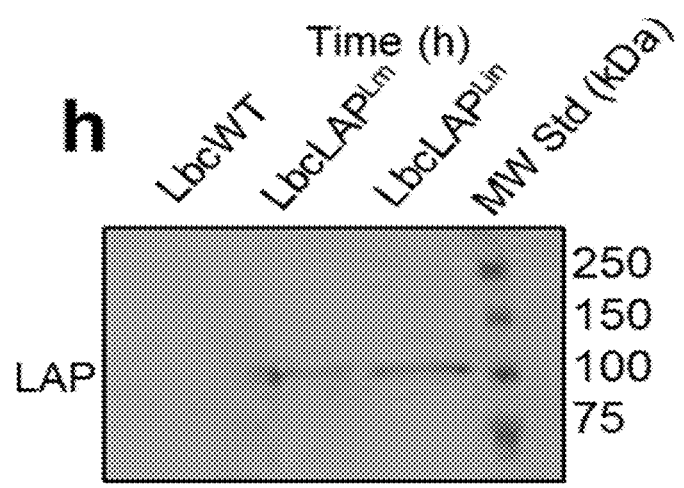

The prophylactic effect of BLP feeding on listeriosis in mice was investigated using 8-10 weeks old female A/J mice that are highly sensitive to listeriosis (Czuprynski et al., 2003) in four experimental trials conducted over 5 years. Before the mice feeding experiment, probiotics survival in the simulated gastric fluid (SGF) and simulated intestinal fluid I (SIF-I) and II (SIF-II) were ensured by plate counting (FIGS. 3D-3F). Live/dead staining using carboxyfluorescein diacetate succinimidyl ester (cFDA) and propidium iodide (PI) also confirmed probiotics survival in gastric fluids (FIG. 3G) and Western blot showed LAP expression on BLP strains while grown in SIF-II (FIG. 3H).

Figure 4A:
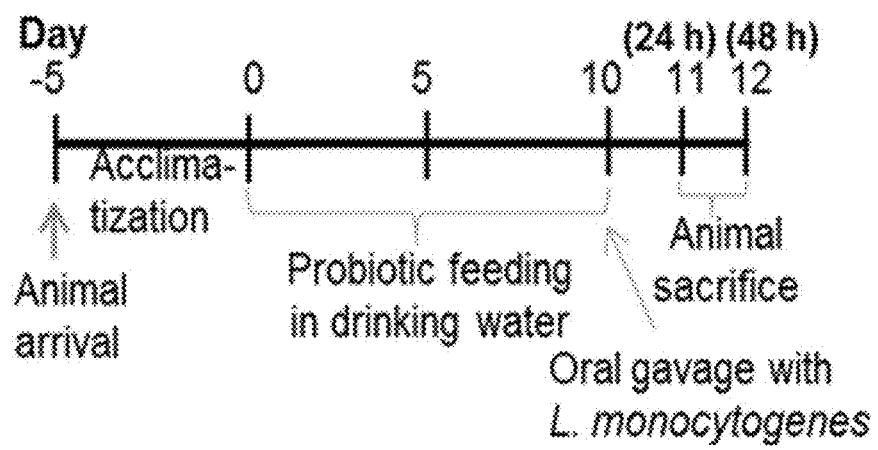
FIGS. 4A-4K demonstrate that bioengineered *Lactobacillus casei* reduced *L. monocytogenes* infection in a mouse (A/J) model.
Figure 4B:
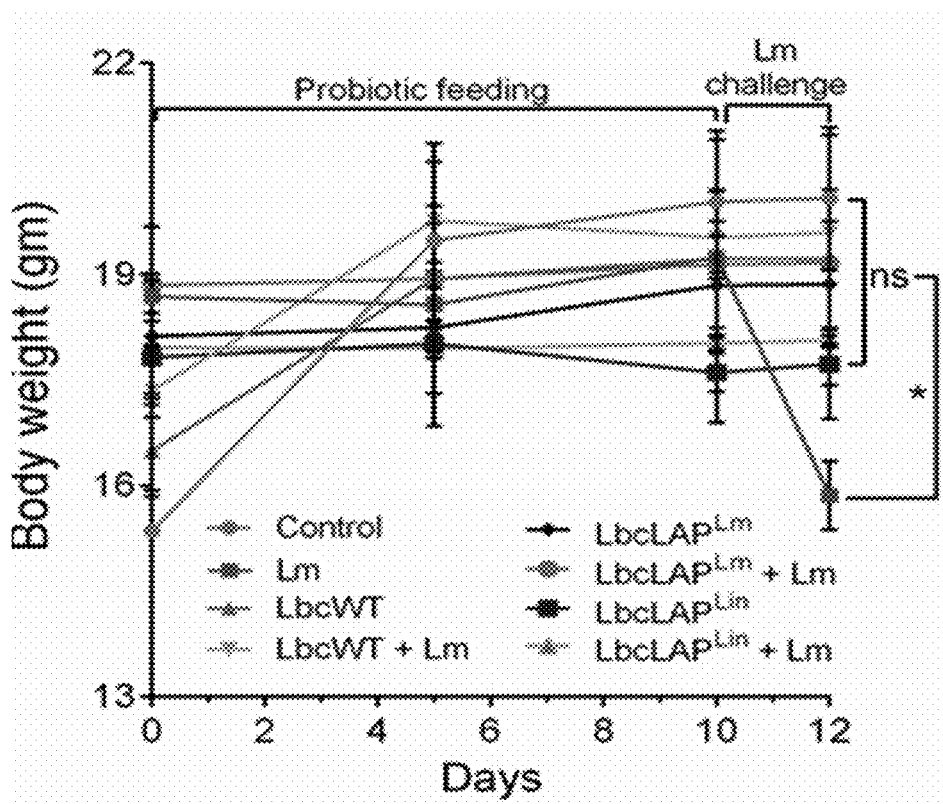
Figure 5:
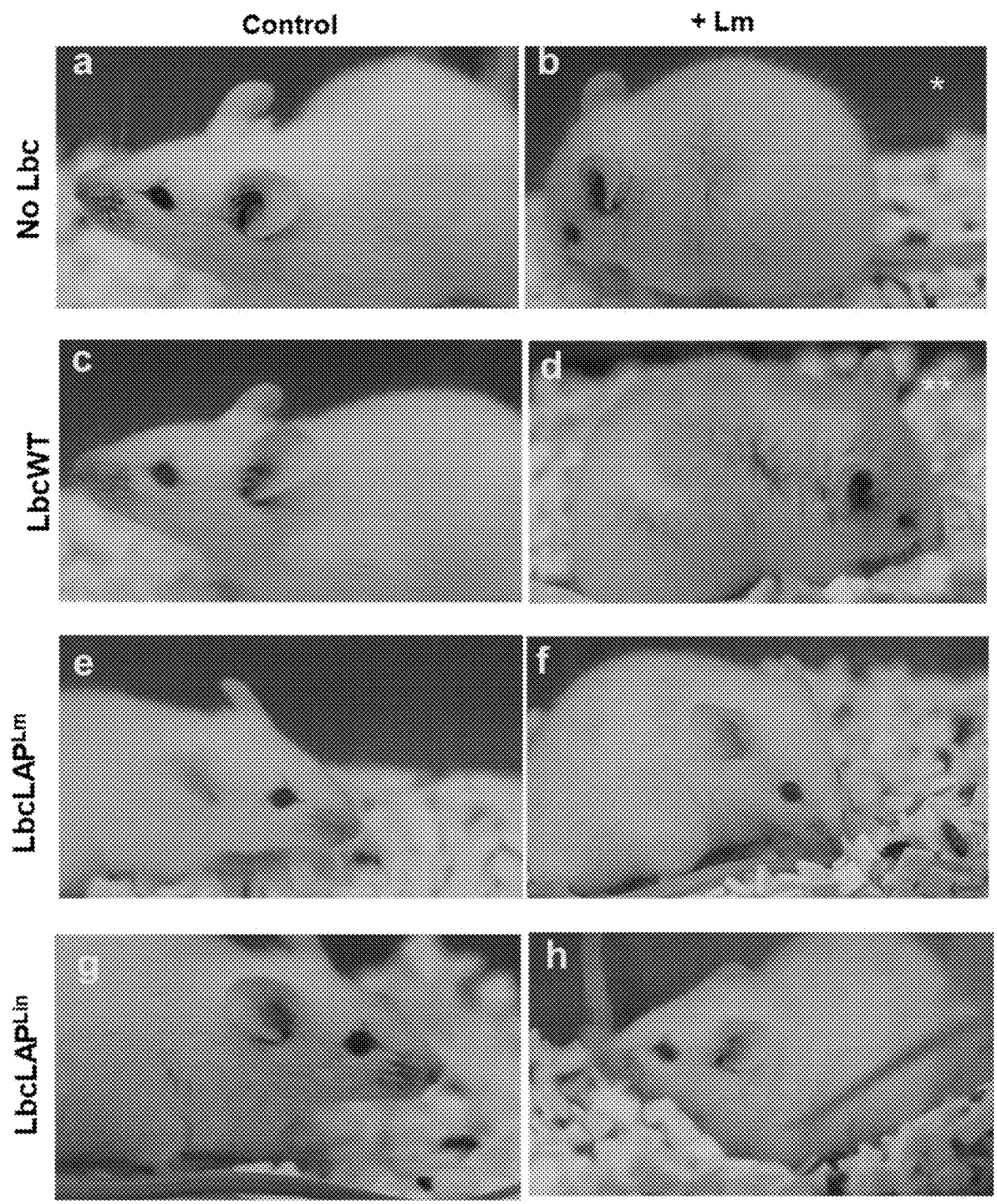
FIG. 5 shows visual examination of health status of mice after challenged with *L. monocytogenes*. The animals in the left panels (a,c,e,g) were not challenged (control), while the right panels (b,d,f,h) were challenged with *L. monocytogenes* F4244. The clinical onset of listeriosis in (b) No Lbc+Lm and (d) LbcWT+Lm was evident. LbcLAP$^{Lin}$+Lm mice appeared healthy.

Freshly grown probiotics bacteria were supplied daily in 50 ml drinking water per mouse (probiotic viability was maintained at about $4 \times 10^9$ CFU/ml) for 10 days before an oral challenge with *L. monocytogenes* F4244 (serovar 4b) strain ($5 \times 10^8$ CFU/mouse) (FIG. 4A). All probiotic-fed animals maintained a constant body weight during the entire study, even after the challenge with *L. monocytogenes* strain on day 10. However, the animals that did not receive any probiotics, but were challenged with *L. monocytogenes* lost >15% body weight (FIG. 4B). BLP-fed mice appeared healthy and continued to feed and drink even after *L. monocytogenes* challenge, while the control animals without any probiotics or animals receiving the LbcWT but were challenged with *L. monocytogenes*, appeared ill (FIG. 5). The sick animals displayed ruffled hair, recumbency, reduced responsiveness to external stimuli, and reduced feed intake.

Figure 4C:
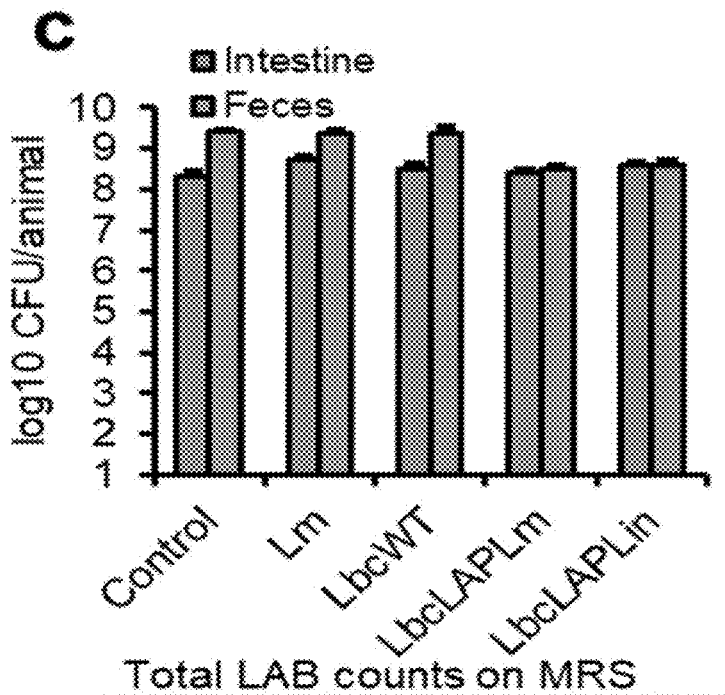
Figure 4D:
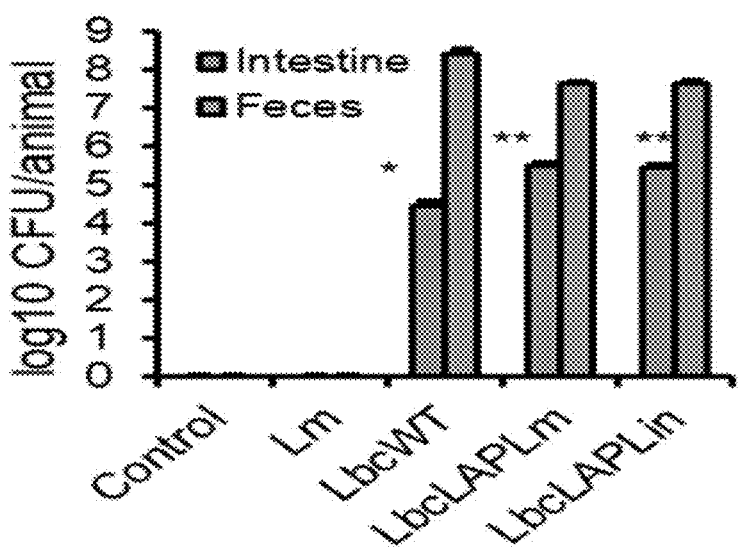
Figures 4E, 4F:
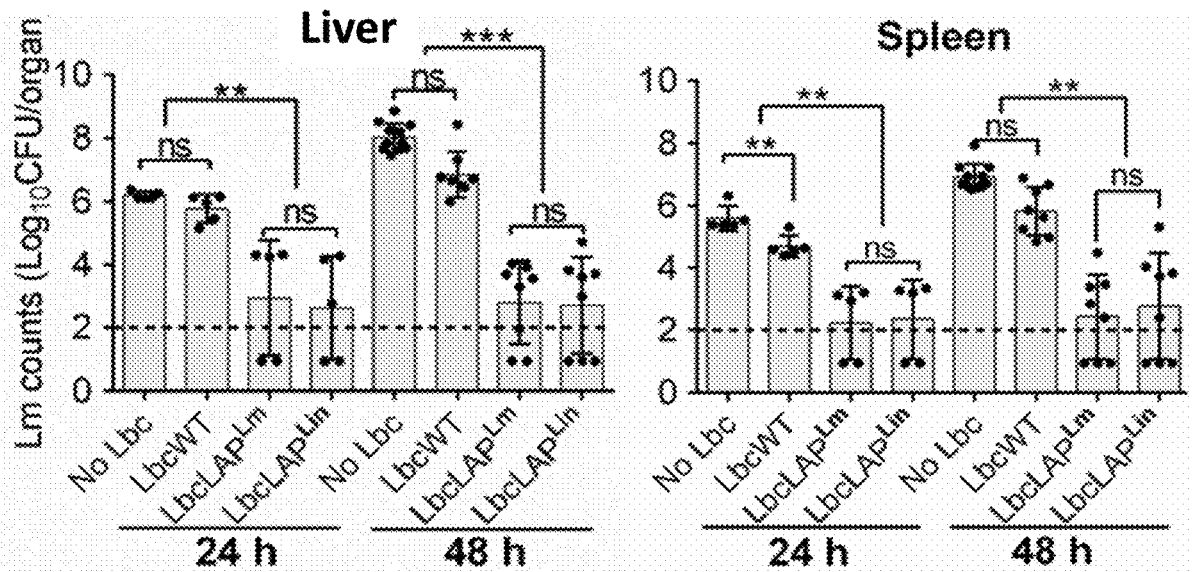
Figures 4G, 4H:
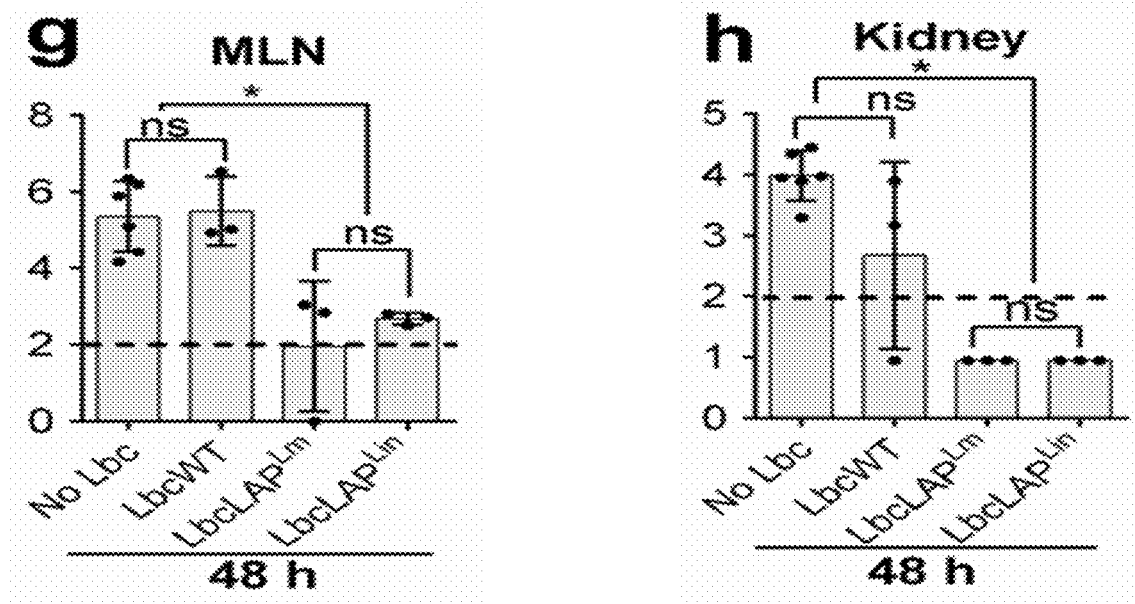
Figure 4I:
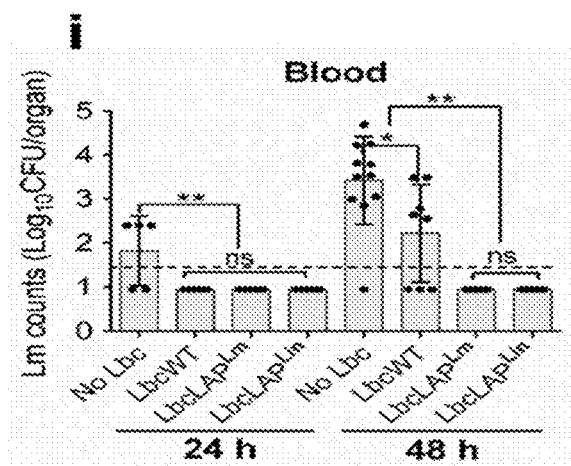
Figure 4J:
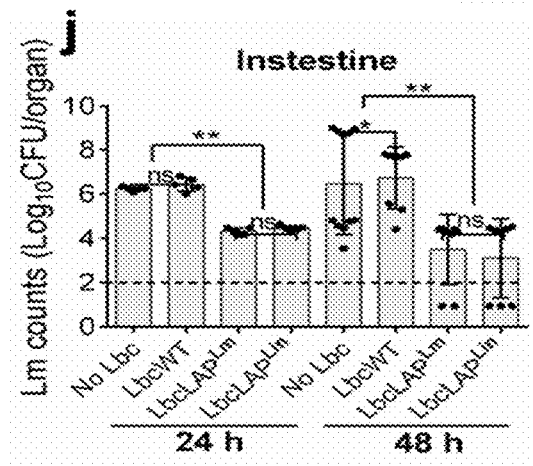
Figure 4K:
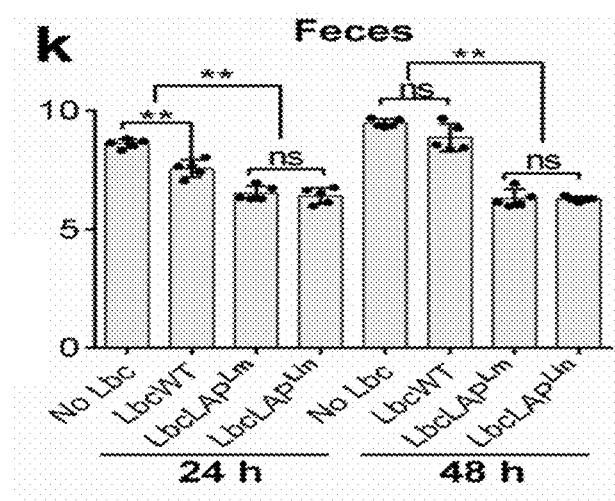

Animals were sacrificed at 24 and 48 h post-infection (pi) in Trial 1 (n=60) and after 48 h pi in Trial 2 (n=30). *L. monocytogenes* counts in the liver, spleen, MLN, kidneys, blood, intestine, and feces were determined (FIGS. 4E-4K). Irrespective of the tissues or organs examined, the LbcWT feeding resulted in a meager 0-1 log CFU/mouse reduction of *L. monocytogenes* counts. (FIG. 4E-4K). Astonishingly, the BLP-fed mice showed a reduction of *L. monocytogenes* counts by 1.5-3 log (up to 99.9%) after 24 h and 3.5-5 log (up to 99.999%) 48 h pi in liver and spleen of half the test population while *L. monocytogenes* was undetectable in the remainder of mice. *L. monocytogenes* was also undetectable in blood and the kidney of BLP-fed mice (FIG. 4H, 4I). No background *Listeria* was detected from any mice that received only the probiotics or no probiotics at all.

Intestinal colonization and fecal shedding of *L. monocytogenes* in probiotic-fed mice were also examined. BLP feeding also significantly reduced *L. monocytogenes* colonization in the intestine (FIG. 4J) and fecal shedding (FIG. 4K), compared with that of the LbcWT-fed mice. Total lactic acid bacteria (LAB) counts in the intestine, and feces of mice were relatively constant irrespective of the bacterial treatments (FIG. 4C). While the LbcWT and the BLP colonization in the gut (intestine and feces) were maintained at about 4.5 log and 5.5 log CFU/mouse, respectively, when intestinal samples were analyzed 48 h pi (FIG. 4D). Collectively, these data demonstrate that bioengineered probiotics were maintained in the intestine of mice for the duration of the study and protected mice from the extra-intestinal spread of *L. monocytogenes*.

Bioengineered Probiotics Protected Gut Barrier Integrity.

Figure 6A:
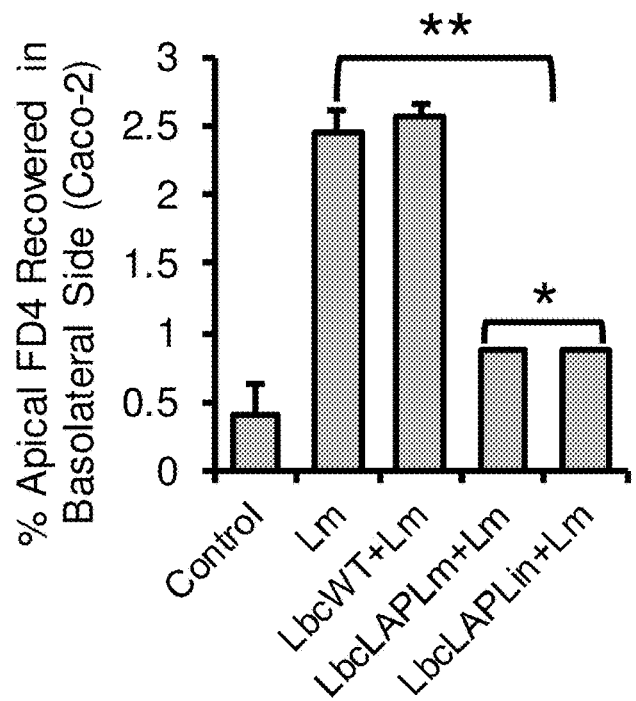
FIGS. 6A-6D demonstrate epithelial permeability assessment after probiotic exposure.
Figure 6B:
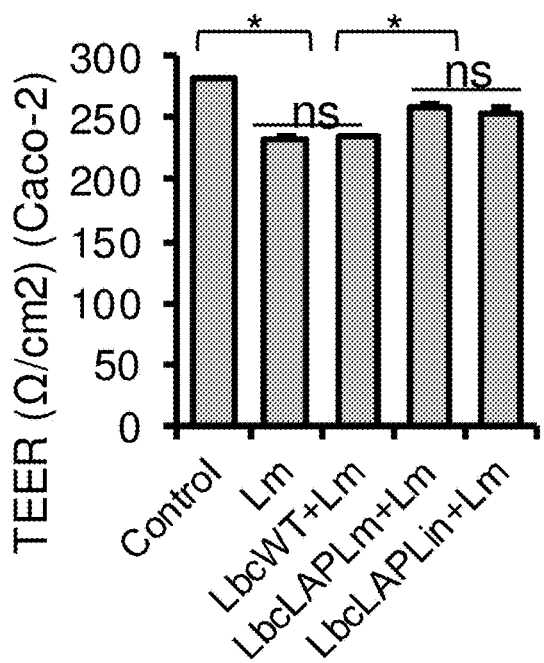

We have demonstrated in previous studies that LAP induces epithelial barrier dysfunction and promotes of *L. monocytogenes* translocation in both in vitro cell culture (Burkholder and Bhunia, 2010; Kim and Bhunia, 2013) and in vivo mouse model (Drolia et al., 2018). Countering this effect, probiotics are known to maintain epithelial tight junction integrity through the immunomodulatory effect which is orchestrated by NF-kB and the secretion of proinflammatory cytokines such as TNFα, IL-1β, IL-6 (Ahrne and Hagslatt, 2011; Pagnini et al., 2010; Zareie et al., 2006). First, we examined if the BLP were able to maintain the intestinal epithelial integrity thereby preventing *L. monocytogenes* translocation to extra-intestinal sites. Epithelial permeability was assessed in Caco-2 cell monolayers by monitoring the diffusion of FD4 from apical to basolateral side (FIG. 6A), and by measuring transepithelial electrical resistance (TEER) in a trans-well set up (FIG. 6B). Caco-2 cells pre-treated with or without LbcWT for 24 h followed by *L. monocytogenes* challenge for 2 h resulted in a very high FD4 permeability (61-64% change) compared to the control, while LbcLAP$^{Lm}$ or LbcLAP$^{Lin}$, pre-treatment for 24 h substantially reduced FD4 translocation following *L. monocytogenes* infection resulting in only 22% change compared to the untreated control (FIG. 6A). Likewise, BLP (LbcLAP$^{Lm}$ or LbcLAP$^{Lin}$) pre-exposure followed by *L. monocytogenes* caused only 2.3-6.9% change in Caco-2 TEER values while *L. monocytogenes* alone caused a 17% change (FIG. 6B).]

Figure 6C:
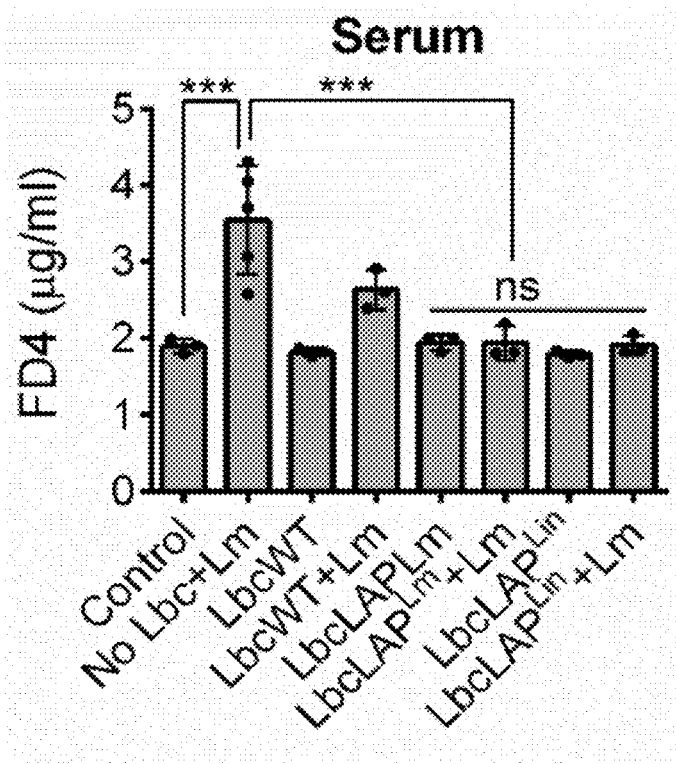
Figure 6D:
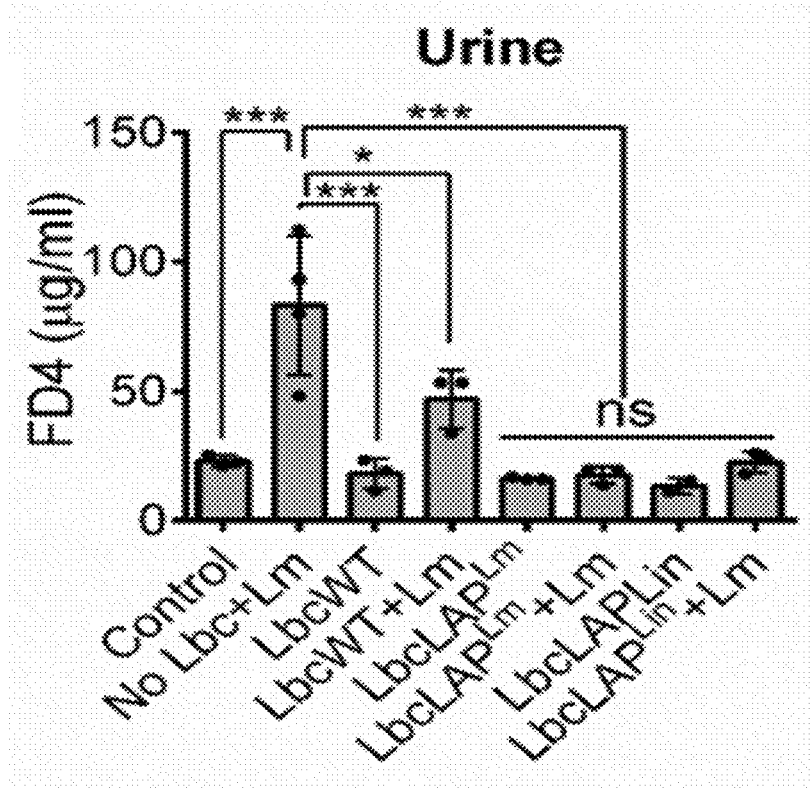

Gut permeability was also assessed in BLP-fed mice by monitoring the levels of FD4 in serum and urine (Drolia et al., 2018). BLP-fed mice challenged with *L. monocytogenes* were orally administered with the FD4 4-5 h prior to sacrifice (Drolia et al., 2018). Animals (FIGS. 2A-2F) that did not receive any probiotics, but were challenged with *L. monocytogenes* had an FD4 level at 3.5±0.3 µg/ml in sera (FIG. 6C) and 83.3±13.5 µg/ml in urine (FIG. 6D). In LbcWT-fed animals, the FD4 levels in sera and urine were 1.82 µg/ml and 18.0 µg/ml, respectively, while the FD4 levels were 2.6 µg/ml and 46.9 µg/ml, after *L. monocytogenes* challenge. In contrast, the FD4 levels in both sera and urine in animals that received BLP with or without *L. monocytogenes* challenge had substantially lower FD4 (about 1.9 µg/ml in sera and 13.2-22.4 µg/ml in urine) equivalent to that of the control mice that did not receive either bacterium. These data clearly demonstrate that probiotics especially the LAP-expressing BP were able to attenuate *L. monocytogenes*-mediated epithelial dysfunction in a mouse model. Transmission electron microscopy (TEM) also showed epithelial tight junction opening in ileal tissue sections of mice fed with Lm but not with bioengineered probiotic followed by Lm as examined by transmission electron microscopy (TEM).

Figure 7A:
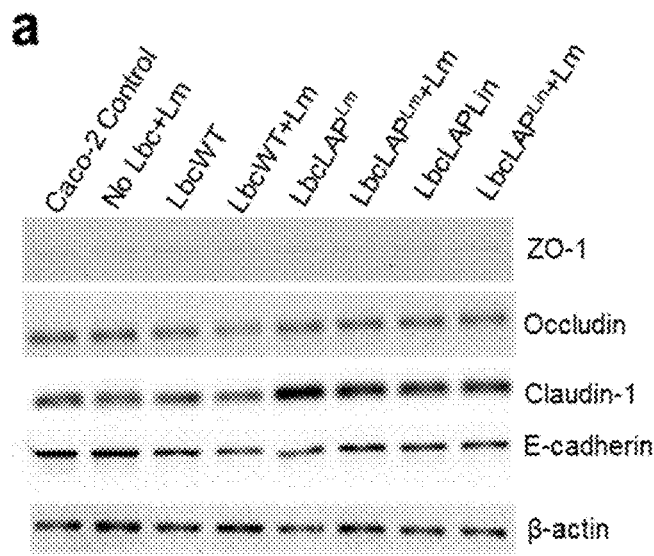
FIGS. 7A-7C show cellular junctional protein distribution analysis in Caco-2 and ileal tissue of mice.
Figure 7B:
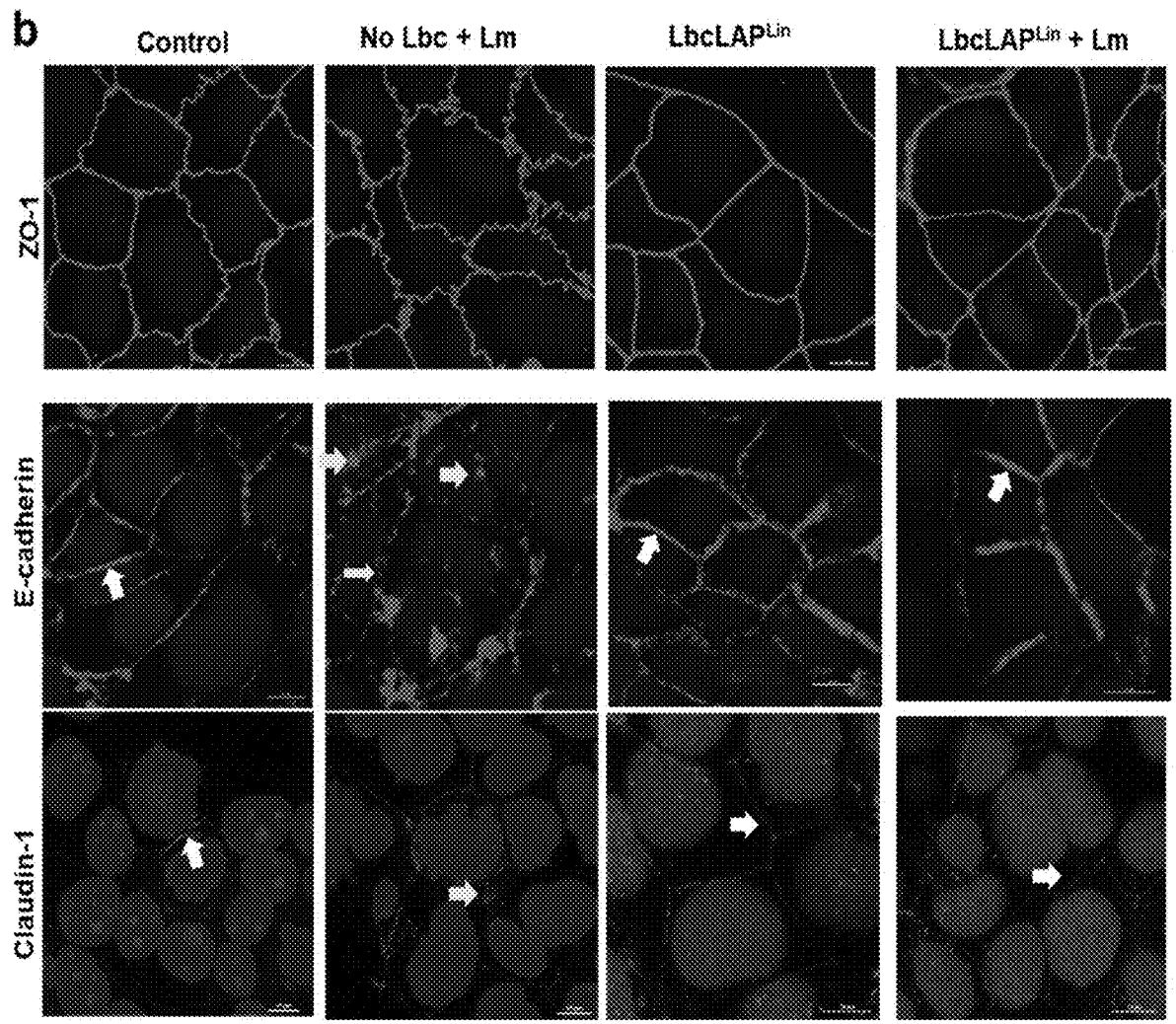
Figure 7C:
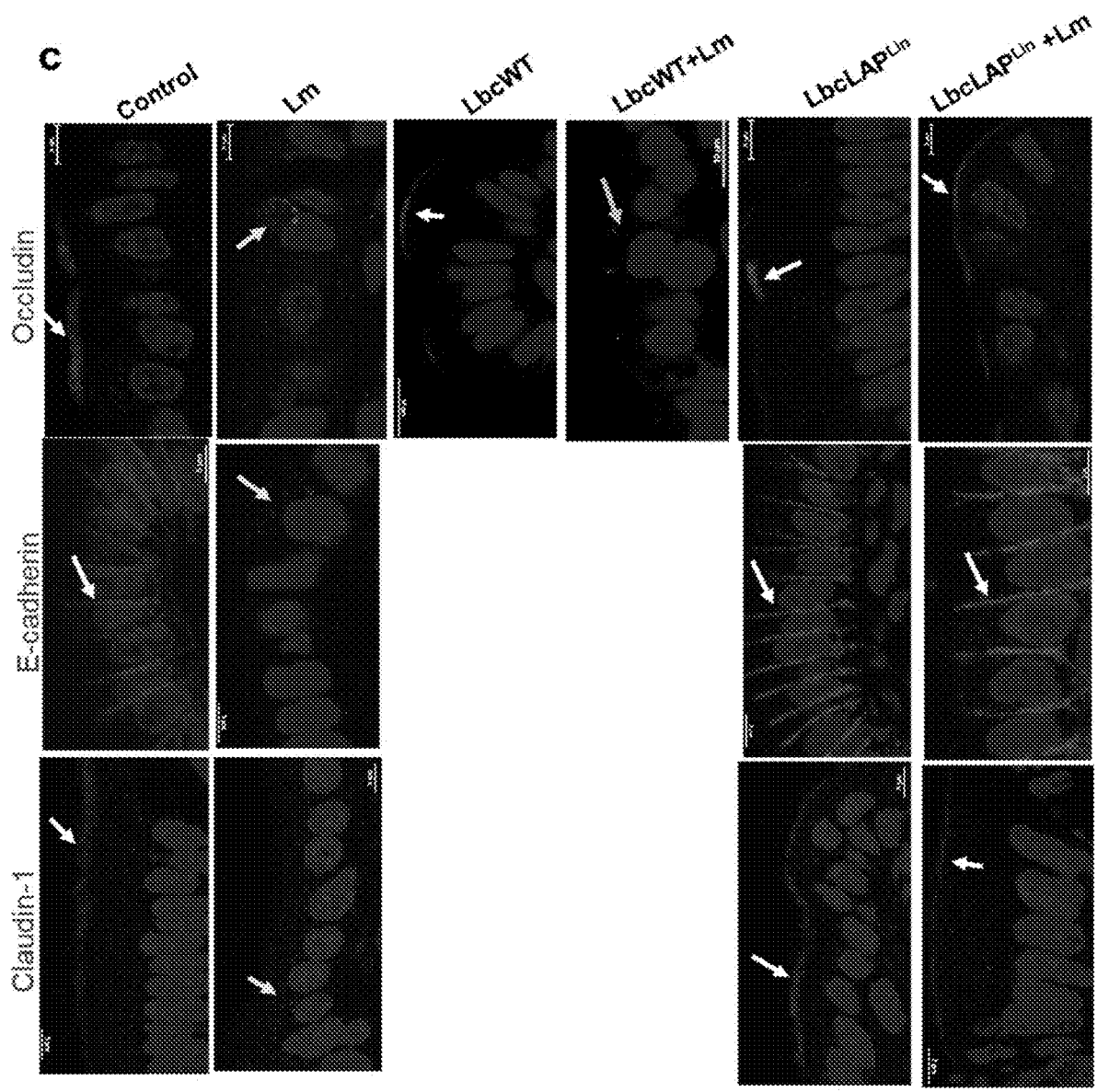

LAP-mediated epithelial barrier dysfunction is governed by mislocalization of epithelial junction proteins, claudin-1, occludin, and E-cadherin (Drolia et al., 2018). In Caco-2 cells, *L. monocytogenes* WT alone or Caco-2 pre-treated with probiotics significantly decreased membrane localization of claudin-1, occludin, and E-cadherin analyzed by Western blotting (FIG. 7A) and the corresponding transcripts in agreement with our previous study (Drolia et al., 2018). Pre-treatment with the BLP prevented *L. monocytogenes*-mediated claudin-1, occludin and E-cadherin mislocalization. Confocal immunofluorescence microscopy confirmed destabilization of the cell junction architecture as ZO-1 disruption by *L. monocytogenes* was pronounced with a discontinuous cell membrane boundary, which was not seen when the Caco-2 cells were pre-treated with the BLP (FIG. 7B). E-cadherin and claudin were sequestered in *L. monocytogenes*-treated Caco-2 cell cytoplasm but was not seen in the BLP pre-treated cells (FIG. 7B) Similar results were seen in mice ilea where BLP-fed mice maintained intact claudin-1, occludin and E-cadherin even after challenging with *L. monocytogenes* (FIG. 7C). Taken together, these data indicate that both BLP strains, but not the wild-type probiotics maintained the tight junction integrity and thus prevented *L. monocytogenes* movement across the epithelial cell barrier.

Ileal Tissue Histology and Innate Immune Response to Bioengineered Probiotic.

Figure 8A:
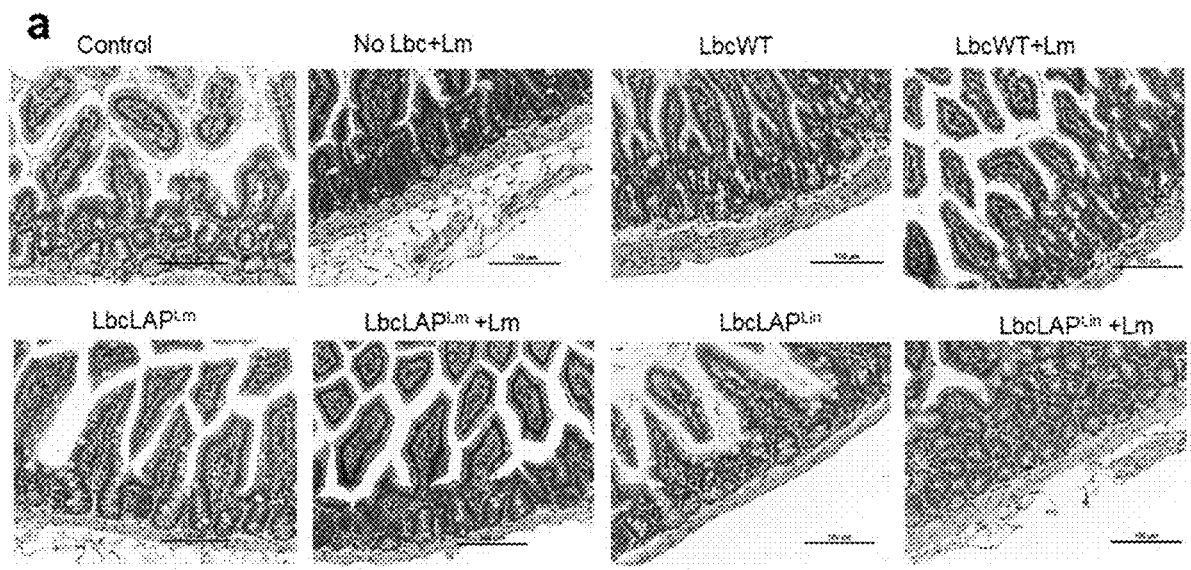
FIGS. 8A-8E show histopathological scoring of ileal tissues of bioengineered probiotic-fed mice. (8A) H&E stained sections, (8B) Histology score, (8C & 8D) Increased goblet cell counts in bioengineered probiotic-fed mice ileal tissues. (8E) Immunostaining of tissue sections for Hsp60 expression, (8F) analysis of transcripts of hspdl (hsp60) in ileal tissues in probiotic fed mice. Treatments were, control, No Lbc+Lm, LbcWT, LbcWT+Lm, LbcLAP$^{Lin}$, LbcLAP$^{Lm}$+Lm, LbcLAP$^{Lin}$, LbcLAP$^{Lin}$+Lm. (8E & 8F) In the presence of *L. monocytogenes*, epithelial cells expressed a high level of Hsp60 irrespective of probiotic treatment. Data were analyzed by one way ANOVA, and Tukey's grouping was used to determine statistical significance at ***, P<0.0001; *, P<0.05, ns, not significant).
Figure 8B:
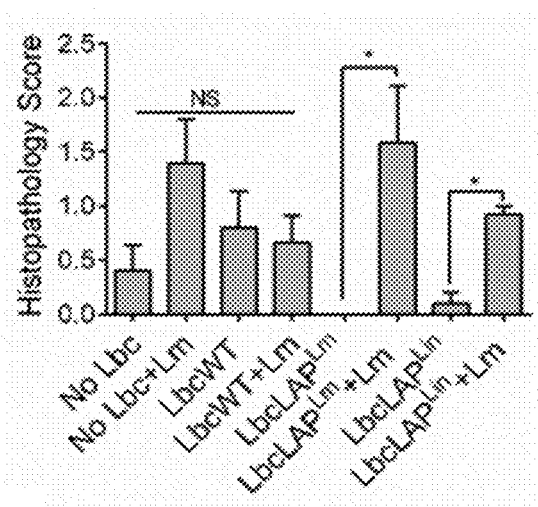
Figure 8C:
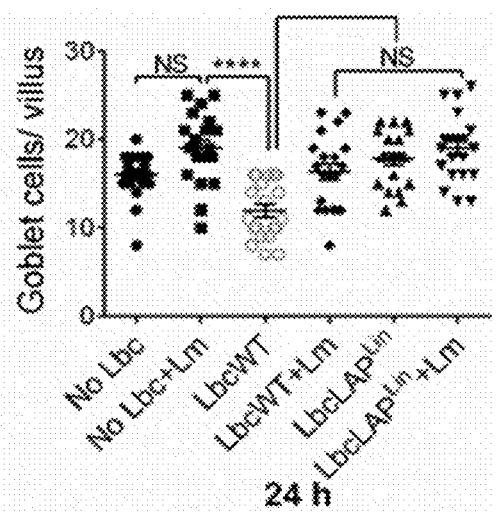
Figure 8D:
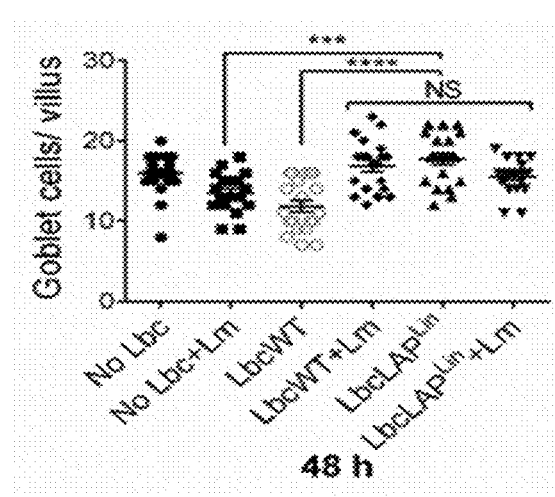

Ileal tissue sections from mice collected at 48 h pi were first examined for inflammation after hematoxylin and eosin staining. Overall, the inflammation due to *L. monocytogenes* infection in 48 h pi was subtle (FIGS. 8A-8B). Ileal tissues of untreated control mice had cylindrical villi with relatively few lymphocytes in the lamina propria. Goblet cells (10% of the villous epithelium) and Paneth cells were mostly confined to the intestinal crypts. The remaining cells of the villous epithelium were enterocytes. The mice that did not receive any probiotics, but were challenged with *L. monocytogenes* had mildly increased numbers of goblet cells at 24 h than the mice received only the LbcWT (FIGS. 8C-8D) in the villous epithelium with neutrophil infiltration at the base of the villous lamina propria. The BLP-fed mice challenged with *L. monocytogenes* showed the highest average histomorphological score, and higher goblet cell counts; however, the enterocytes remained intact with no sign of apparent necrosis (FIGS. 8A-8D).

Figure 8F:
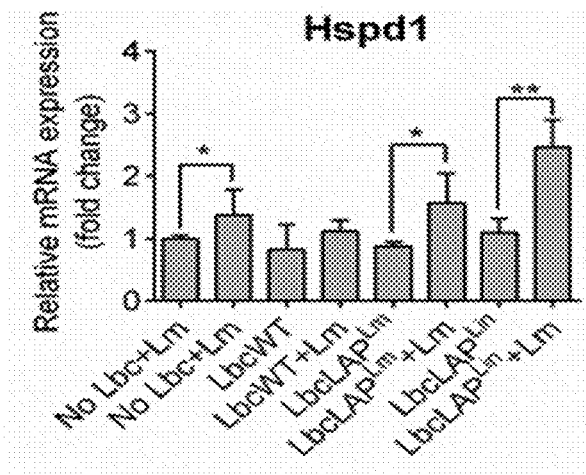
Figure 8E:
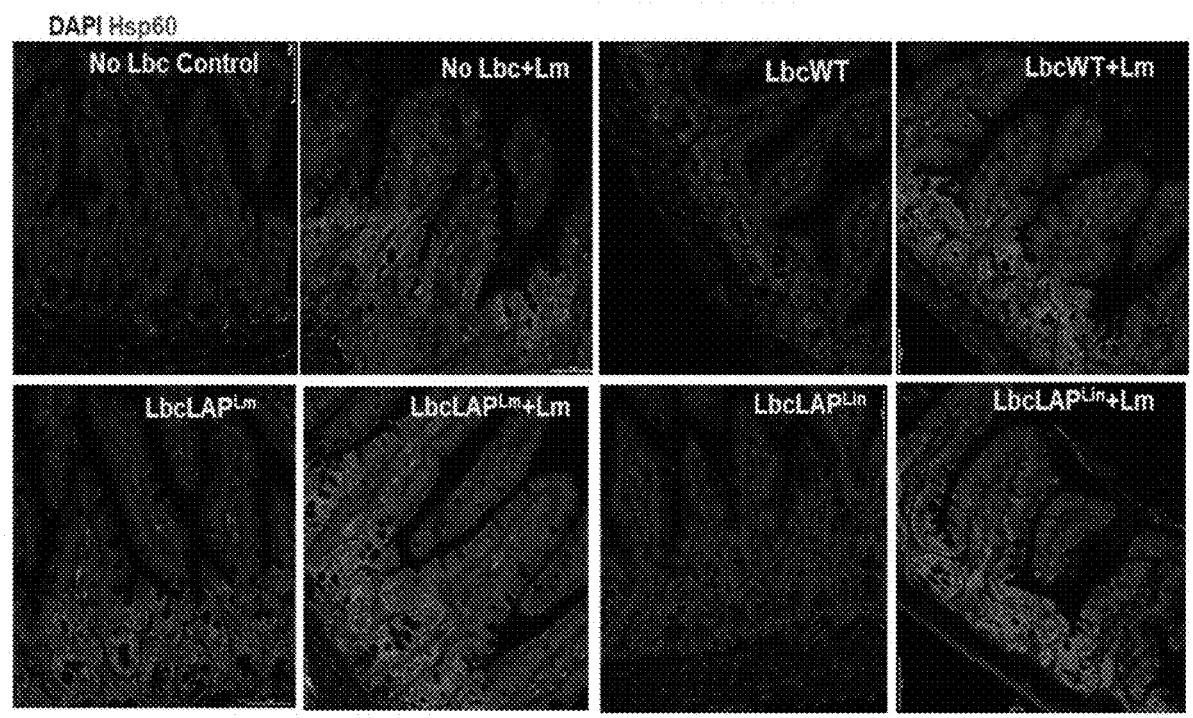

Mammalian Hsp60 activates innate immune response (Chen et al., 1999; Pockley, 2003). Earlier, we observed that *L. monocytogenes* infection induced membrane Hsp60 expression, which subsequently facilitated enhanced LAP-mediated *L. monocytogenes* translocation (Burkholder and Bhunia, 2010; Drolia et al., 2018) by breaching an innate immune system in the mouse. Therefore, we examined the Hsp60 expression in the mouse ileal sections. Hsp60 expression was pronounced and uniformly distributed on the villous epithelial cells of mice that did not receive any probiotics but challenged with *L. monocytogenes* for 48 h (FIG. 8E). Expression of Hsp60 was lower in all probiotic-fed mice but enhanced when challenged with *L. monocytogenes*. A similar trend was observed when the levels of hsppdl (hsp60) transcripts were analyzed in the ileal tissue samples (FIG. 8F). These data demonstrate that BLP was able to dampen the Hsp60 expression, however, after the *L. monocytogenes* challenge, Hsp60 expression increased in epithelial cells, which may help the host cells to defend against the infection through a mechanism which requires further investigation.

Immunomodulatory and Anti-Inflammatory Effects of Probiotic Feeding in Mice.

Figure 9A:
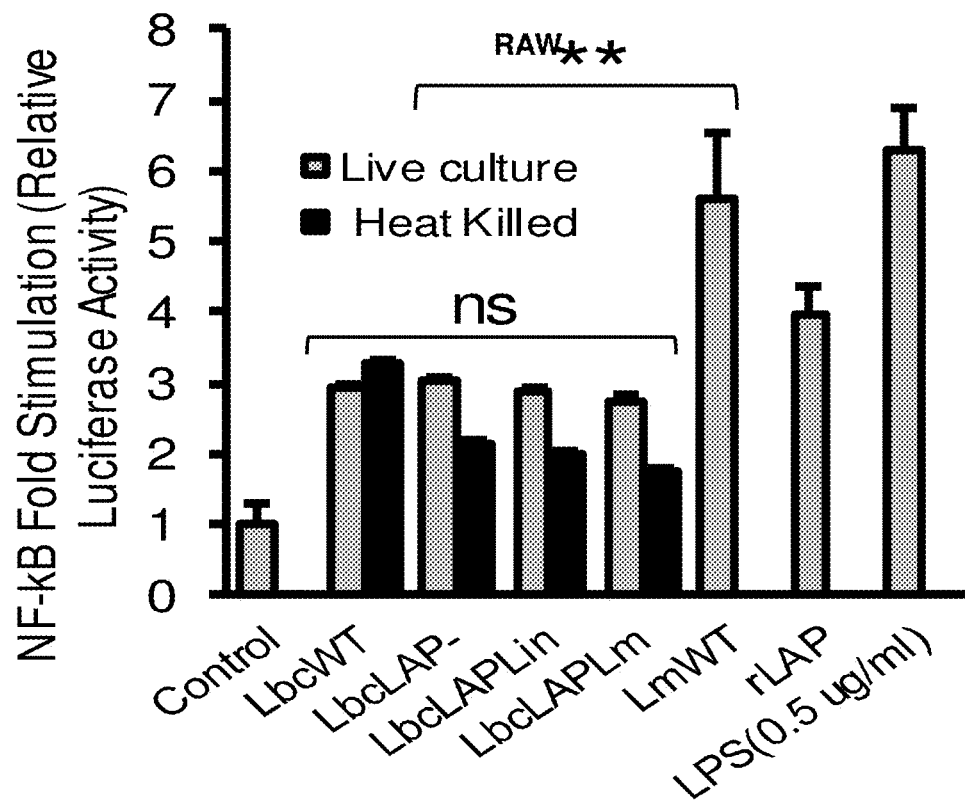
FIGS. 9A-9I show immunomodulatory and anti-inflammatory effects of probiotics in RAW macrophage cell line and in mice. (9A & 9B) Attenuation of NF-kB expression in the luciferase reporter RAW cell line (a) and mouse ileum (b). Confocal imaging shows attenuation of NF-kB activity by probiotics compared to Lm WT (b). (9C & 9D) TNF-α and IL-6 expression in mice ilea after probiotic exposure. (9E-9G) Flow cytometry analysis showing spleen CD4 cell levels were unaffected while CD8 and CD11c cell levels were increased after challenged with probiotics followed by Lm challenge. (9H) Spleen cytology score and (9I) light microscopic imaging showed an increased inflammatory response in characterized by infiltration of neutrophils, macrophages, and lymphocytes, and blinded cytology score to probiotic pre-exposure followed by *L. monocytogenes* infection. Treatments were, control, No Lbc+Lm, LbcWT, LbcWT+Lm, LbcLAP$^{Lm}$, LbcLAP$^{Lm}$+Lm, LbcLAP$^{Lin}$, LbcLAP$^{Lin}$+Lm. (n=3-10 mice/group). Two-way ANOVA and one-tailed T-tests of individual probiotic treatment pairs were used to demonstrates a significance at P<0.05.
Figure 9B:
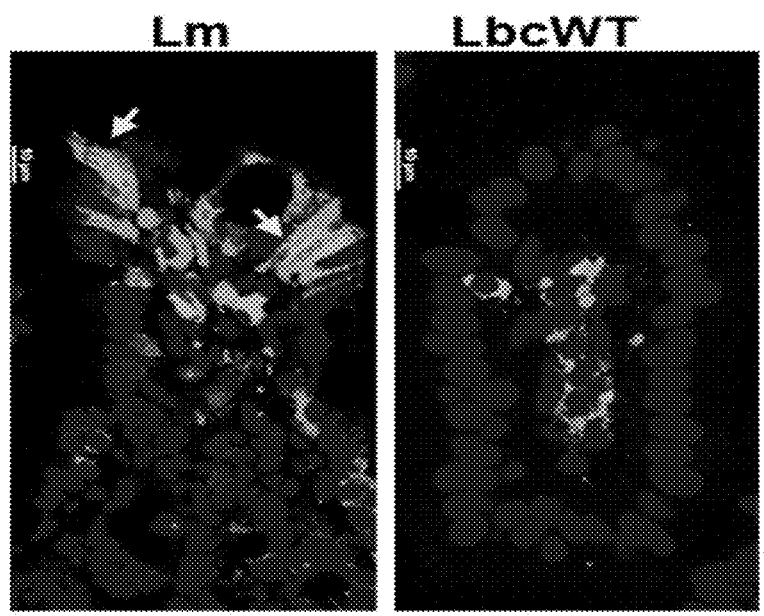
Figure 9C:
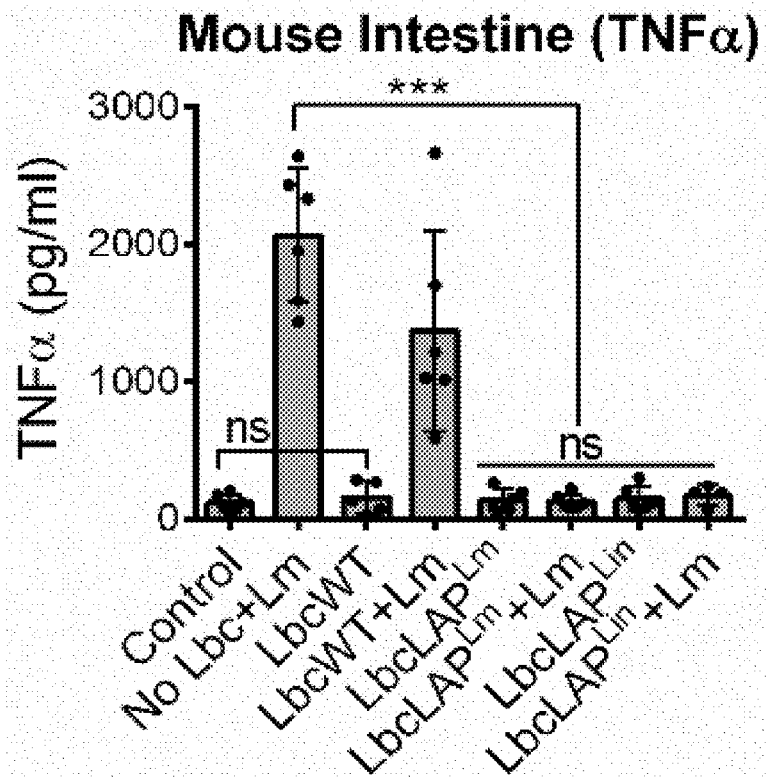
Figure 9D:
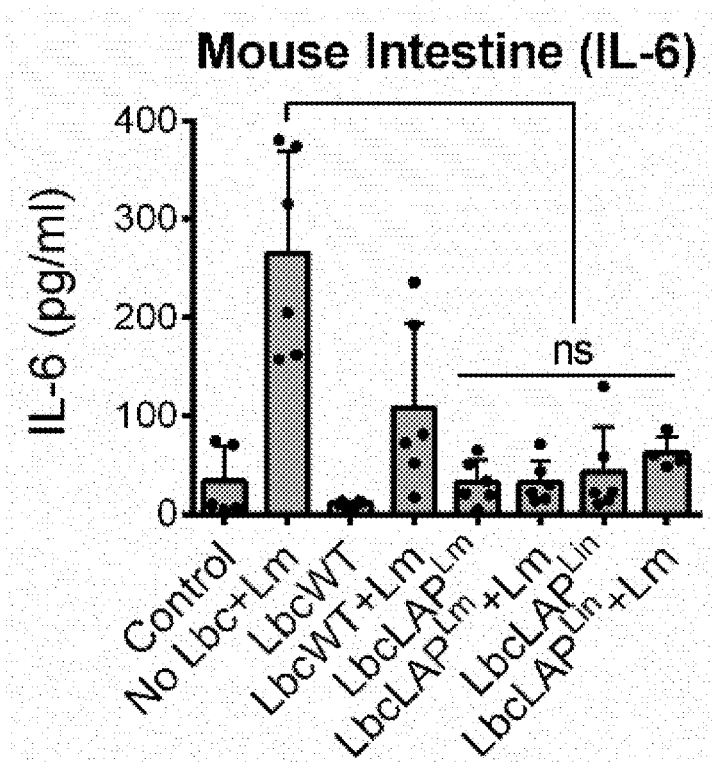

Probiotic bacteria modulate the immune response and maintain immune homeostasis via activation of NF-κB and production of epithelial TNF-α (Cross, 2002; Pagnini et al., 2010). Moreover, both TNF-α and IL-6 increase epithelial barrier permeability through activation of NF-κB (Ma et al., 2004). Earlier, we have shown that LAP of *L. monocytogenes* stimulates NF-κB, produces epithelial TNF-α and IL-6 and increases epithelial permeability by dysregulating epithelial junctional proteins (Drolia et al., 2018). Here, we observed that the BLP strains lowered approximately 2-fold NF-κB activity in a Luciferase reporter RAW (murine macrophage) cell line compared to that of *L. monocytogenes* WT or LPS-treated control cells (FIG. 9A). Confocal immunostaining of ileal tissue samples also showed increased translocation of P-p65 and p65 into the nucleus by *L. monocytogenes* WT but reduced levels in BLP-pretreated mice indicating that BLP stimulates NF-kB (FIG. 9B). Furthermore, TNF-α and IL-6 levels were increased substantially in the murine ileal tissue extracts (FIGS. 9C-9D) from *L. monocytogenes* infected mice without probiotic feeding, while the levels were equivalent to that of the uninfected controls when fed with the BLP strains.

To assess the state of systemic immune response in BLP-fed mice, levels of several cytokines in the pooled sera from the three animals within each treatment group were analyzed using a semi-quantitative immunoblot array. Strong IL-6 and MCP-1 response were observed in animals that were infected with *L. monocytogenes* without any pre-exposure to probiotics; however, both the wild-type probiotic and BLP exposure significantly dampened these cytokines in *L. monocytogenes*-infected mice. In contrast, levels of G-CSF was very high in sera after *L. monocytogenes* challenge, irrespective of the probiotics used. Serum TNF-α level was undetectable irrespective of the treatments, possibly the array could not detect trace amounts.

Figure 9E:
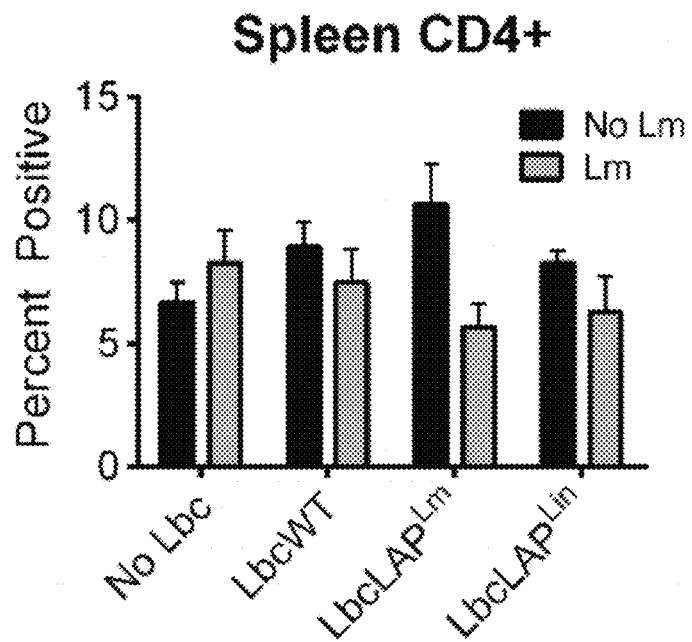
Figure 9F:
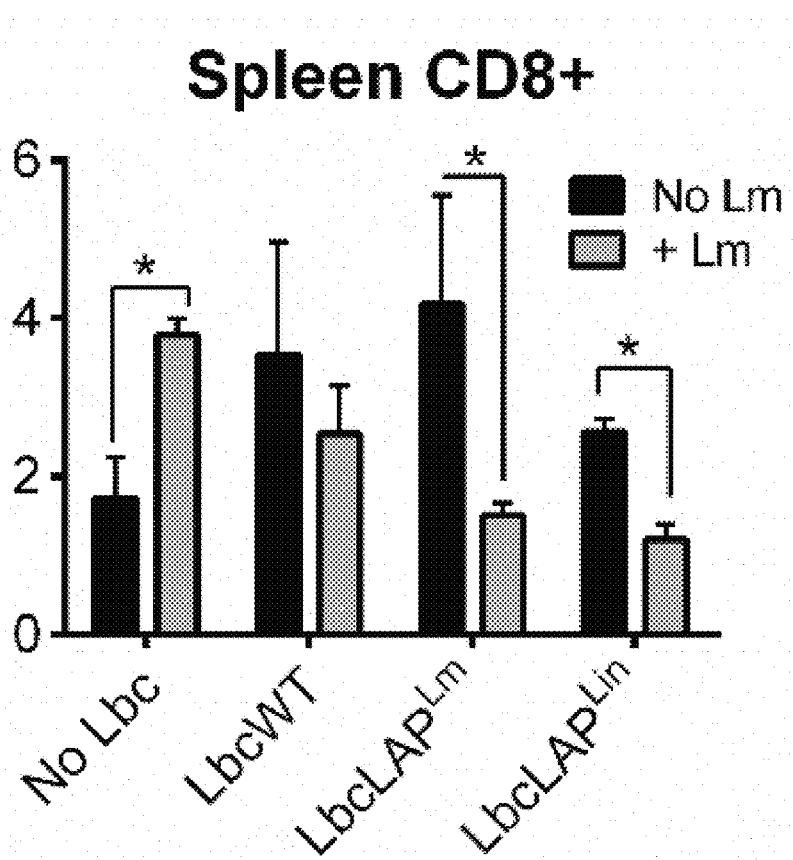
Figure 9G:
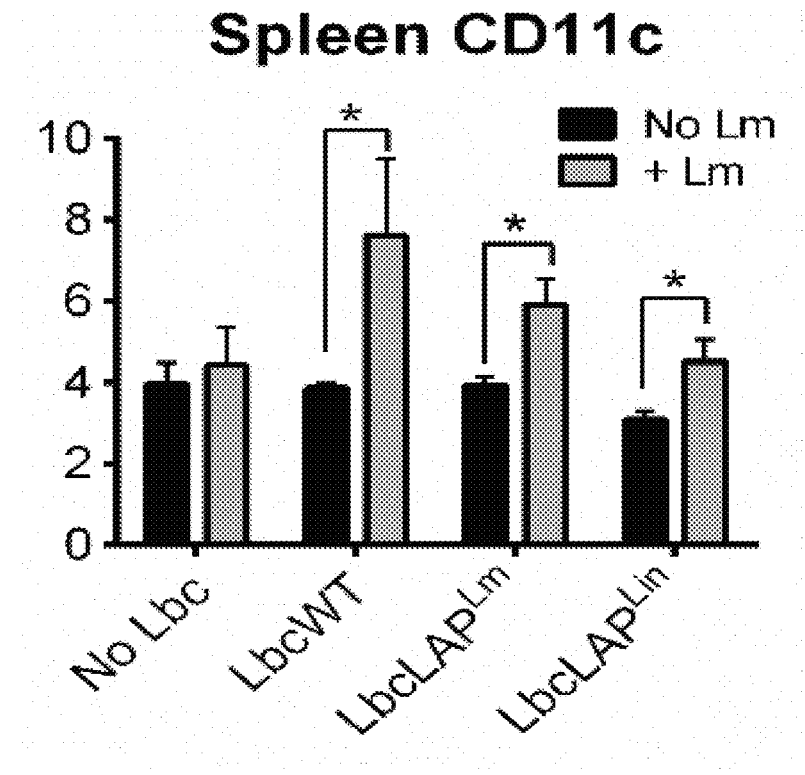

Probiotic bacteria also influenced cellular immune response to *L. monocytogenes* infection as seen in the spleen by flow cytometry and cytology. Among the splenic $CD4^+$ (FIG. 9E) and $CD8\alpha^+$ (FIG. 9F) T cell populations, only $CD8\alpha^+$ counts showed a strong response in mice challenged with *L. monocytogenes* in the absence of any probiotic, while the counts were lower in BLP-primed mice following *L. monocytogenes* challenge. *L. monocytogenes* infection also increased splenic $CD11c^+$ (dendritic cell) counts irrespective of the type of probiotics used (FIG. 9G).

Figure 9H:
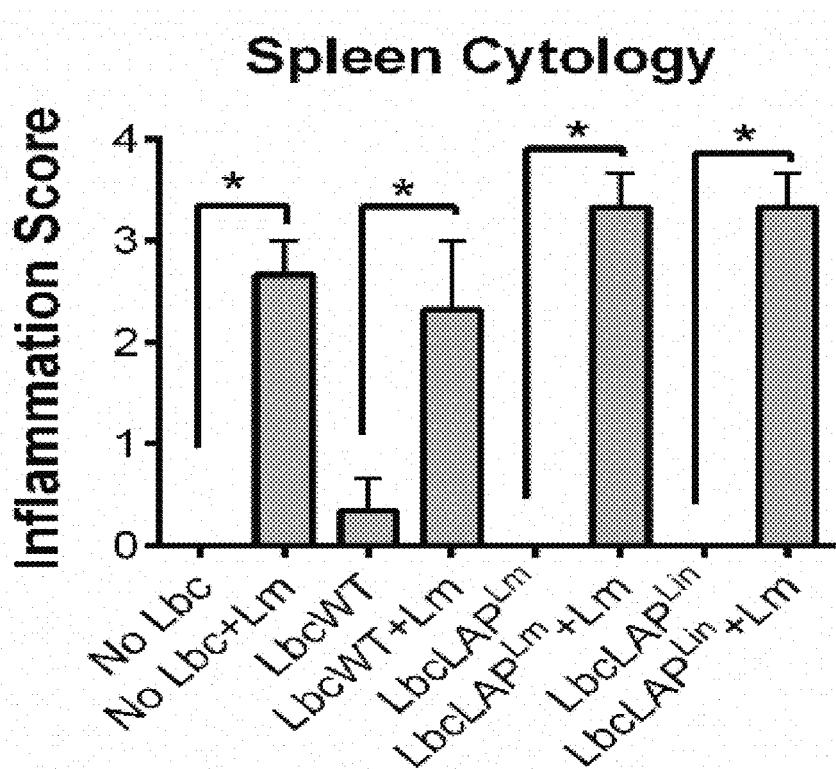
Figure 9I:
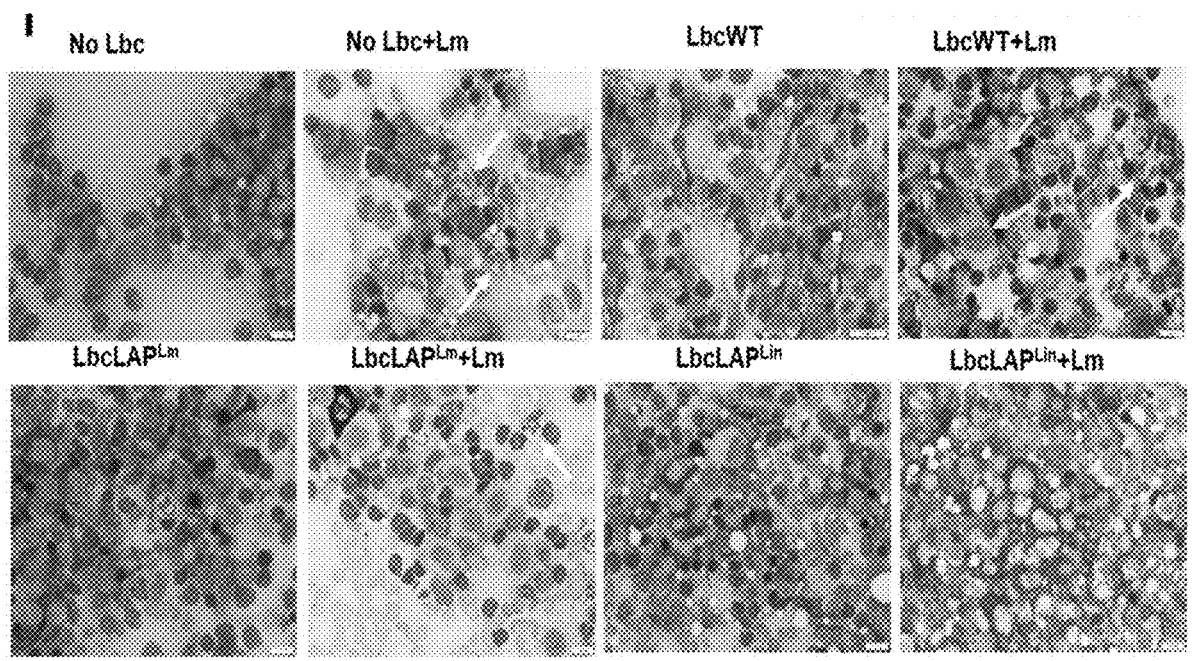
Figure 10A:
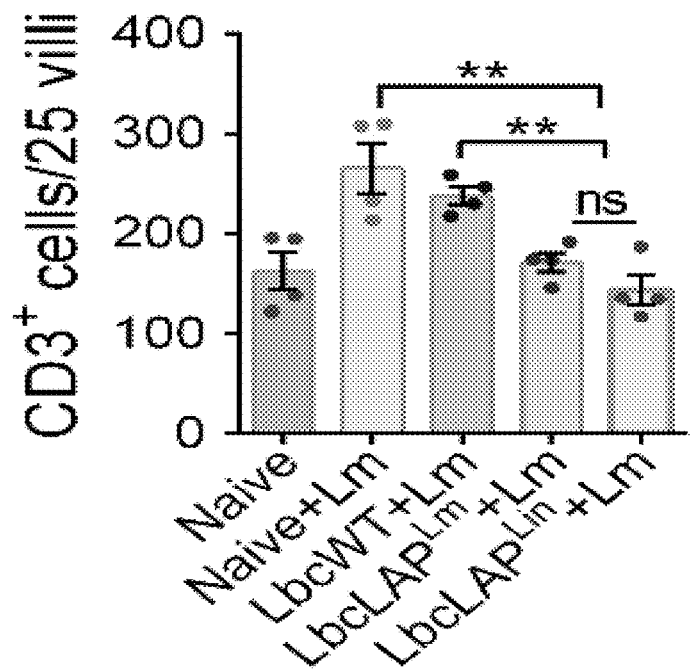
FIGS. 10A-10D. Immunomodulatory action of probiotics expressing the LAP protein: Ileum harvested from A/J mice supplied with or without probiotics for ten days followed by 48 h-post infection with *L. monocytogenes* was immunostained for CD3 (10A), CD8α (10B), Fox-P3 (10C), and cleaved caspase-3 (10D, CC-3; marker of apoptosis. Graphs show CD3$^+$, CD8α$^+$, CC-3$^+$ and CD4$^+$ Fox-P3+, cells from 25 villi/mouse. Each point represents an individual mouse. Mice fed with probiotics expressing the LAP protein (LbcLAP$^{Lm}$ or LbcLAP$^{Lin}$) prior to *L. monocytogenes* infection show significantly reduced CD3$^+$, CD8$^+$ (arrows), CC-3$^+$ cells but significantly increased CD4$^+$ Foxp3$^+$ cells.
Figure 10B:
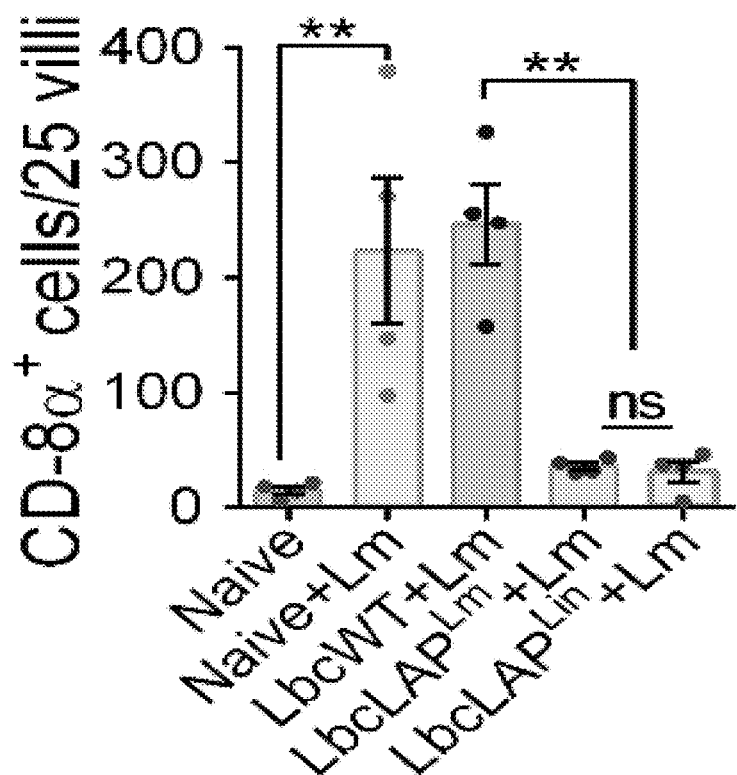
Figure 10C:
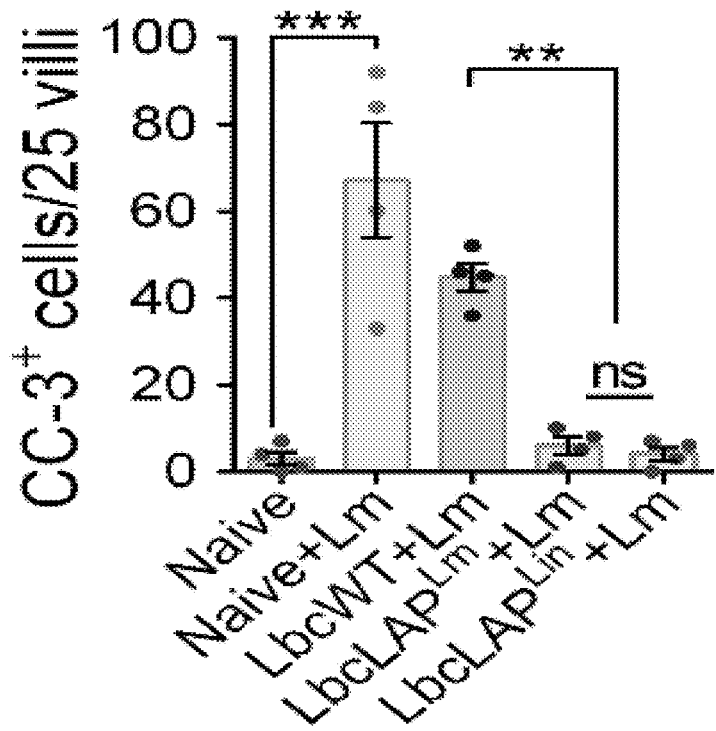
Figure 10D:
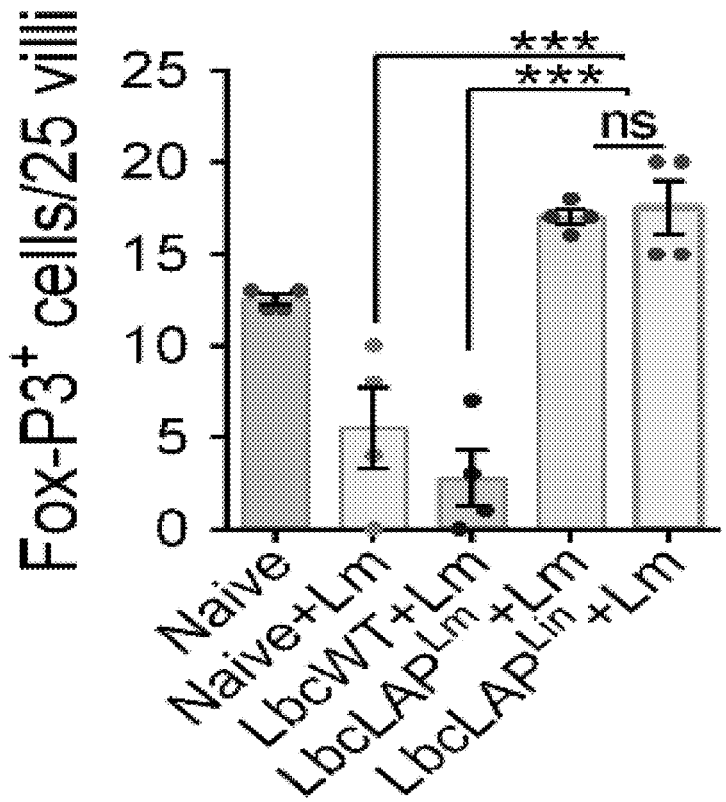

Cytological imprints from splenic cross-sections did not reveal any obvious lymphoid hyperplasia in control animals while *L. monocytogenes* infection resulted in significant neutrophil and macrophage infiltration (FIG. 9I). No cytological evidence of inflammation was apparent in any probiotic-fed animals. Interestingly, BLP-fed animals followed by *L. monocytogenes* challenge showed moderate-to-marked inflammation with increased infiltration of macrophages and neutrophils (FIG. 9I). Blinded cytology scoring also confirmed such observation (FIG. 9H). The immunomodulatory and anti-inflammatory effects of probiotics and reduced *Listeria* counts in spleen (FIG. 4F) strongly suggest that BLP positively influenced cellular immune response for efficient clearance of *L. monocytogenes* from extra-intestinal sites.

Immunomodulatory effect of probiotic was also assessed in ileal tissues by immunostaining of ileal tissue sections with T-cell markers, anti-CD3$^+$; anti-CD8$^+$ and CD4$^+$ FoxP3$^+$ antibodies which revealed significant differences in total T-cell counts between the control and bioengineered probiotic-fed mice as shown in FIGS. 10A-10D. Bioengineered probiotics (BLP) enhanced the regulatory T cell (CD4$^+$ FoxP3$^+$) response while cytotoxic (CD8$^+$) cell counts were low. This suggests that bioengineered probiotic was able to prime the immune system, which possibly helped eliminate invaded *L. monocytogenes* cells and maintain tight junction integrity to prevent bacterial passage or increased clearance of pathogens that were able to cross the epithelial barrier, especially from the BLP-fed mice where most animals showed reduced systemic infection (FIGS. 4A-4K).

Figure 11:
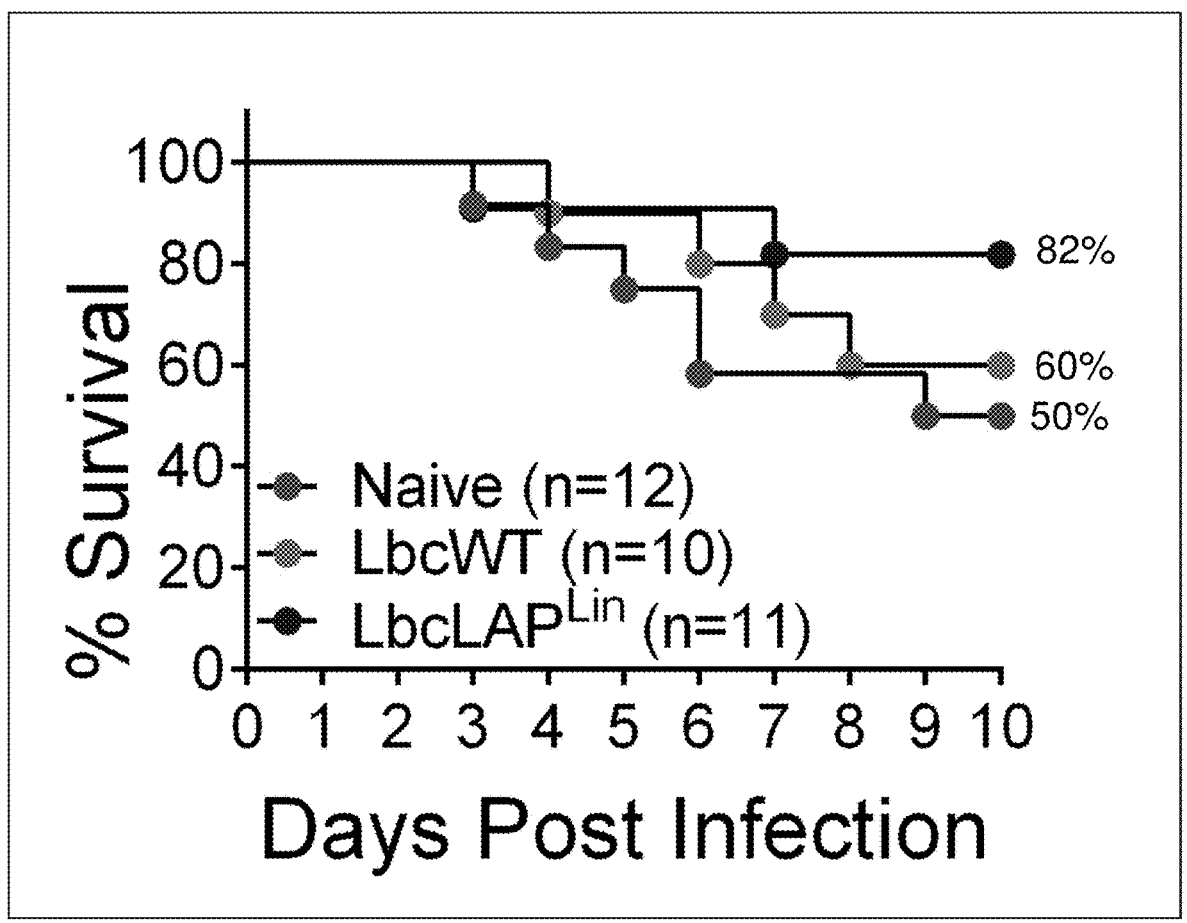
FIG. 11 shows survival of mice (A/J strain) supplied with or without probiotics for ten days in drinking water followed by oral infection with *L. monocytogens* (n=at least 10 per group). Mice fed with *Lactobacillus casei* (probiotics)

FIG. 11 shows survival of mice (A/J strain) supplied with or without probiotics for ten days in drinking water followed by oral infection with *L. monocytogens* (n=at least 10 per group). Mice fed with *Lactobacillus casei* (probiotics) expressing the LAP protein (LbcLAPLin) showed significantly (**P<0.01, Kaplan-Meier log-rank test) higher survival compared to that of LbcWT.

We also measured the levels of secretory IgA (sIgA) in the ileal mucus samples, and the total sIgA levels for probiotic-fed mice were considerably higher than the control animals; however, there were no differences in LbcWT and the BLP-fed mice indicating probiotics natural ability to induce sIgA production (Bakker-Zierikzee et al., 2006). We also could not detect any LAP-specific antibody in the pooled mice sera from either LbcWT or BLP-fed mice. This provides evidence against submucosal translocation of LAP-expressing probiotics, which is in agreement with Caco-2 transwell data (FIG. 2B). However, the sera from probiotic-fed mice that were challenged with *L. monocytogenes* for 48 h exhibited a very faint antibody reaction with LAP, for which there is no specific explanation. Nevertheless, these data demonstrate that probiotics-mediated humoral immune response, especially the sIgA may also affect *L. monocytogenes* interaction with intestinal epithelial cells during the early phase of infection (Mantis et al., 2011).

Bioengineered probiotic feeding also increased survival of mice after *L. monocytogenes* challenge. Mice were fed with probiotic bacteria for 10 days and then challenged with lethal dosage of *L. monocytogenes* ($2\times10^9$ CFU/mouse). Mice survival was examined over 10 days. Over 82% mice from bioengineered probiotic (LbcLAPLin)-fed mice group survived while 60% and 50% mice survived that received LbcWT and no probiotic control (naïve), respectively (FIG. 11). This study clearly indicates that LAP-expressing bioengineered probiotic bacteria can prevent fatal infection caused by *L. monocytogenes*.

*Listeria monocytogenes* is an invasive opportunistic intracellular human pathogen. It is ubiquitous and is transmitted primarily through food resulting in numerous fatal and costly outbreaks that are associated with consumption of contaminated cheese, ice cream, fish, ready-to-eat meats, and produce (cantaloupe, apples, sprouts, spinach). Besides pregnancy, immune suppressed conditions in the elderly, and malignancy, organ transplant and HIV-AIDs patients are also highly vulnerable (Schuchat et al., 1991). The case fatality rate of listeriosis is 19%. Currently, there is no preventive vaccine against listeriosis except for general precautionary guidelines outlined by the CDC that include thorough cooking of meat, safe food handling practices and avoidance of the FDA designated high-risk foods, such as frankfurters, soft cheeses made with unpasteurized milk, pate, and smoked fish. Therefore, prophylactic intervention strategies for the high-risk population from listeriosis would have a greater public health impact. One of the promising alternatives to the use of antibiotics in prophylaxis or therapy is the utilization of probiotic microbes (Amalaradjou and Bhunia, 2012; Sanders et al., 2014). Probiotic microbes also produce metabolites and macromolecules promoting gut health by modifying cytokine production and enhancing gut barrier function (Bron et al., 2017; Cho et al., 2014; Salminen et al., 2010). Probiotic microbes can prevent/alleviate chronic inflammatory bowel disease, colorectal cancer, metabolic disorders and obesity, and osteoporosis (Amalaradjou and Bhunia, 2012; Azcarate-Peril et al., 2011; Ly et al., 2011). Probiotics are also used in pre-term neonates to allow early colonization with beneficial microbes (Deshpande et al., 2011), and increased sIgA secretion in the gut (Bakker-Zierikzee et al., 2006). Among the different probiotic bacteria used, *Lactobacillus* species is most common because of their ability to survive, colonize and modulate the immune system in the gut, and are generally safe (Amalaradjou and Bhunia, 2012). Earlier, Con et al. (Con et al., 2007) showed that bacteriocin producing Lactobacilli could control listeriosis in a mouse model. However, probiotics approach has been ineffective or has had limited success against listeriosis (Culligan et al., 2009; Koo et al., 2012). To overcome such limitations, we bioengineered a probiotic *Lactobacillus casei* strain to prevent *Listeria* interaction with the epithelial cells in the intestinal tract and subsequent extra-intestinal dissemination.

We have shown previously that LAP plays an important role during early-phase of infection (within 24-48 h), promoting translocation of *L. monocytogenes* across the epithelium in mice (Burkholder et al., 2009; Drolia et al., 2018). The LAP lacks a leader sequence thus the bacterial secretory system, SecA2 helps LAP to secrete to the extracellular milieu and for surface display (Burkholder et al., 2009; Mishra et al., 2011). The LAP from *L. monocytogenes* bears high sequence similarity to the LAP from *L. innocua* (non-pathogen) and the *L. innocua* LAP is unable to re-associate on its own surface possibly due to the lack of a surface anchoring molecule (Jagadeesan et al., 2011; Jagadeesan et al., 2010). This defect probably prevents *L. innocua* from translocating through the epithelial paracellular route (Burkholder and Bhunia, 2010). Interestingly, the *L. innocua* LAP fully restored epithelial translocation ability in a lap-deficient *L. monocytogenes* strain in a cell culture model (this study). This raised an intriguing question; can the LAP from *L. innocua* expressed on probiotic *Lactobacillus* prevent listeriosis in a mouse model? A/J mice are highly sensitive to listeriosis due to C5 complement deficiency (Czuprynski et al., 2003; Jagannath et al., 2000); therefore, these animals should be ideal for studying the prophylactic effect of BLP against listeriosis.

Incredibly, both bioengineered *Lactobacillus casei* expressing LAP" or LAP$^{Lin}$ were able to prevent *L. monocytogenes* dissemination substantially (up to 5 log or 99.999% reduction) to extra-intestinal tissues and organs and the mice appeared healthy when sacrificed at 48 h pi. Both LbcWT and BLP were maintained in the gut during the 10 days feeding trials and they were not detected in any extra-intestinal tissues upon sacrifice implying that either they did not cross the intestinal barrier or the translocated BLP were cleared immediately by the local immune system. Blood sera also did not reveal any noticeable LAP-specific antibody response suggesting that the LAP antigen may not have disseminated systemically.

Two plausible mechanisms for BLP-mediated protection are postulated: (i) Prevention of *L. monocytogenes* interaction with the intestinal epithelial cells by BLP via preoccupation of the intestinal niche, and subsequent binding to *L. monocytogenes*, and (ii) activation of the immune system for increased clearance of the translocated pathogens. Our results also indicate that the BLP prevented *L. monocytogenes* dissemination by maintaining epithelial tight junction integrity as the preservation of the cytoskeleton and tight junction barrier integrity is critical for modulating paracellular and transcellular bacterial diffusion (Pagnini et al., 2010; Zhou et al., 2010). Mislocalization of epithelial junctional proteins, occludin, claudin-1 and E-cadherin in the ileal tissues of the mice was evident in *L. monocytogenes* infected mice and the LbcWT-fed groups, while the cell junction architecture remained intact in animals fed with BLP followed by *L. monocytogenes* infection.

Probiotic bacteria exert immunomodulatory effect (Ng et al., 2009) and promote gut health through stimulation of epithelial innate immunity by stimulating local production of TNF and activation of NF-kB (Pagnini et al., 2010). In agreement with a previous report (Rothe et al., 1993), here we also observed *L. monocytogenes* mediated high levels of TNF-α and IL-6 in the ileal tissue homogenates and IL-6 level in the sera. Indeed, activation of NF-kB results in elevated levels of TNF-α and IL-6, which facilitate gut epithelial barrier destabilization (Drolia et al., 2018; Ma et al., 2004). In our previous report, LAP induced epithelial IL-6 and TNF-α production during *L. monocytogenes* infection through activation of NF-κB (Drolia et al., 2018), in this study, LAP-expressing BLP was able to dampen *L. monocytogenes*-mediated proinflammatory cytokine production despite moderate activation of NF-kB. This suggests, perhaps BLP helped maintain epithelial immune homeostasis thus was able to counteract *L. monocytogenes* mediated inflammatory response. During innate immunity, epithelial cells and monocytes secrete IL-6 when stimulated by pathogen-associated molecular patterns (PAMPS) on specific pathogens that are recognized by pattern recognition receptors (PRR) including Toll-like receptors (TLRs) similar to LAP-Hsp60 interaction (Drolia et al., 2018). Previous in vitro studies using RAW264.7 macrophages exposed to cell wall extracts of *Bifidobacterium adolescentis*, *B. longum*, and *Lactobacillus salivarius* Ren enhanced phagocytic activity via increased production of IL-6 and TNF-α (Zhu et al., 2011). Oral gavage of mice with *L. acidophilus* and *B. bifidum* showed increased reactive oxygen intermediates production and enhanced phagocytic activity in macrophages (Deepti and Vinod, 2014). A long-term consumption of probiotic has shown to enhance innate immunity and production of IL-1, IL-1β, IL-6, IL-10, IL-12, IL-18, INF-γ, and TNF-α by monocytes and DC (Cross, 2002; Niers et al., 2005).

Cell-mediated immunity especially the $CD8^+$ T-cell response is critical for controlling systemic *L. monocytogenes* infection (Huleatt et al., 2001). Here we also observed increased cell counts with $CD8\alpha^+$ marker in spleen in the *L. monocytogenes* infected control group 48 h pi, while the opposite trend in BLP-fed animals. $CD8\alpha^+$ cells represent both cytotoxic T-cells and a subset of dendritic cells, and both are requisite for efficient splenic infiltration during intravenous administration of *L. monocytogenes* in mice (Edelson et al., 2011). The concomitant marked increase in neutrophils, macrophages and dendritic cells ($CD11c^+$ and spleen cytology data) in the spleen with *L. monocytogenes* infection in the BP-fed groups above the control infection group suggests that perhaps the BP strains serve to prime the innate immune system. As such, increased phagocyte infiltration may lead ultimately to improved pathogen clearance without the need for $CD8^+$ T-cells. Prophylactic oral administration of *L. casei* CRL431 has positively influenced neutrophil response to a nasally inoculated *Streptococcus pneumoniae*, demonstrating a potentially important link in mucosal immunity between different organ systems (Villena et al., 2005). The total splenic $CD4^+$ T cell population did not change in our study, but other Tx subtypes that may contribute to the overall differential immune response were not measured. Probiotic microbe-induced sIgA response in ileal mucus in mice pre-exposed to both LbcWT and the BLP, akin to previous studies (Bakker-Zierikzee et al., 2006; Sakai et al., 2014) suggesting that the probiotic bacteria stimulate mucosal immune response (Mantis et al., 2011) against *L. monocytogenes*.

In summary, the wild-type probiotic strains tested are generally ineffective against *L. monocytogenes* infection (Koo et al., 2012); therefore, the bioengineered probiotic strains were made to prevent listeriosis in a mouse model. Our study has demonstrated that the LAP-expressing bioengineered *Lactobacillus casei*, including the LAP from a nonpathogenic *Listeria*, protected mice from *L. monocytogenes* infection through colonization resistance, maintenance of gut permeability and tight junction stability, and immunomodulation. Such bioengineered strain can potentially prevent listeriosis in high-risk populations and at the same time promote health benefits inherent to probiotic lactobacilli.

Materials and Methods

Bacterial Strains, Plasmids, and Growth Conditions.

All *Listeria* species were grown in tryptic soy broth containing 0.5% yeast extract (TSBYE; Becton Dickinson, Sparks, Md.) or Luria-Bertani broth (LB, 0.5% NaCl, 1% tryptone peptone, and 0.5% yeast extract) at 37° C. for 16 to 18 h. Probiotic bacteria were cultured in deMan Rogosa Sharpe broth (MRS, Becton Dickinson) at 37° C. for 18-20 h. *Lactobacillus casei* ATCC 344 wild-type (LbcWT) (a gift from Mike Miller, University of Illinois, Urbana) was used as a host to express LAP from *L. innocua* and *L. monocytogenes*. To recover this strain from fecal and intestinal samples during the animal study, a vancomycin-resistant strain of *L. casei* was selected by sequentially culturing the bacterium in increasing concentrations of vancomycin (300 µg/ml). Recombinant *L. paracasei* was grown under anaerobic conditions at 37° C. with erythromycin (2 µg/mL). The lap-deficient mutant *L. monocytogenes* strain KB208 was grown in TSBYE with erythromycin (10 µg/mL) at 42° C. KB208 expressing *L. innocua* LAP was grown in TSBYE with erythromycin (5 µg/mL) and chloramphenicol (7 µg/mL) at 42° C.

Generation of Bioengineered Lactobacilli Expressing LAP from *L. innocua* and *L. monocytogenes*.

The entire lap gene (2.6 kb) from *L. innocua* was amplified by PCR and inserted into pLP401T (Pouwels et al., 2001) and electrotransformed into *L. casei* ATCC 334 designated LbcLAP$^{Lin}$ (*L. casei* AKB907) as described before (Koo et al., 2012). Likewise, lap gene from *L. monocytogenes* was expressed in *L. casei* designated LbcLAP$^{Lm}$ (AKB906). The bioengineered strains were maintained in MRS broth containing erythromycin (2 µg/ml) under anaerobic conditions at 37° C. The *L. innocua* lap gene was cloned into pMGS101, electrotransformed into KB208, and designated LmKB208LAP$^{Lin}$. To induce LAP expression, the bioengineered *L. casei* strains, were grown in modified MRS (1% w/v protease peptone, 0.5% w/v yeast extract, 0.2% w/v meat extract, 0.1% v/v TWEEN® 80, 37 mM $C_2H_3NaO_2$, 0.8 mM MgSO4, 0.24 mM MnSO4, 8.8 mM $C_6H_{14}N_2O_7$ in 0.1 M potassium phosphate buffer, pH 7.0) supplemented with mannitol (1% w/v). LAP expression was verified by Western blotting, ELISA and immunofluorescence staining using anti-LAP mAb (Koo et al., 2012).

Growth Characteristics of Recombinant Probiotics in Artificial Gastrointestinal Fluids.

The survival of probiotics exposed sequentially to the simulated gastrointestinal fluid (SGF) and simulated intestinal fluid (SIF-I and SIF-II), to simulate gastric phase, enteric phase 1 and enteric phase 2, respectively), over 6 h (2 h for each step) period was monitored (Buriti et al., 2010). SGF contained pepsin (3 g/L) and lipase (0.9 mg/L) (Sigma-Aldrich), pH 1.2-1.5 (adjusted using 1N HCl). Both SIF-I and SIF—II contained bile (bovine bile; 10 g/L, Sigma-Aldrich) and porcine pancreatin (1 g/L; Sigma-Aldrich), but SIF-I pH was 4.3-5.2 and SIF-II pH 6.7-7.5 (adjusted using alkaline solution; 150 ml of 1 N NaOH, 14 g of $PO_4H_2Na.2H_2O$ and deionized water up to 1 L). Overnight cultures of wild-type or BP were washed and resuspended in SGF (100 ml) and incubated at 37° C., with agitation (150 rpm for 2 h) (gastric phase), and bacterial counts were monitored every 30 min for 2 h. The cells from SGF were pelleted down and transferred sequentially into SIF-I, and SIF-II, incubated each at 37° C. for 2 h to simulate the initial and final phases of intestinal digestion. Probiotics counts were enumerated on MRS plates and the assay was repeated three times with duplicate samples. Viability was also verified by performing live and dead staining using cFDA-SE (carboxyfluorescein diacetate succinimidyl ester, 50 µM) and PI (propidium iodide, 30 µM) as described (Lee et al., 2004). Levels of LAP expression in probiotic cultures during exposure to SGF and SIF were also monitored by immunofluorescence staining and Western blotting using anti-LAP mAb. BP survival in water is also monitored to ensure probiotics viability during animal feeding in a 24-h cycle.

Inhibition of L. monocytogenes Adhesion, Invasion and Paracellular Translocation by BP.

The ability of LbcWT and BP (LbcLAP$^{Lin}$ and LbcLAP$^{Lm}$) to inhibit L. monocytogenes adhesion, invasion, and translocation through Caco-2 cell monolayers was investigated as before (Koo et al., 2012). BLP strains were added to each well (MOE 10) and incubated for 24 h. Unbound bacteria were removed by washing with Dulbecco's modified Eagles' medium containing 10% fetal calf serum (D10F), and L. monocytogenes was added (MOI 10) and incubated for 1 h to determine inhibition of adhesion and invasion. The cell monolayers were then washed three times and adherent bacteria were released by TRITON™ X-100 treatment and plated. To determine intracellular bacteria, the cell monolayers were treated with gentamycin (50 µg/mL) for 1 h before TRITON™ X-100 treatment. As a vector control, the recombinant LbcVecLAP$^-$ strain was used.

Bacterial translocation through epithelial barrier was assayed as before (Burkholder and Bhunia, 2010). Briefly, Caco-2 cells were grown on transwell filter inserts (4-µm pore filter; Corning, Lowell, Mass.) for 10-12 days to reach confluence. Bacteria were added to the apical well of the insert and incubated for 2 h. Liquid from the basal well was removed, serially diluted, and distributed onto TSA-YE agar plates for enumeration. TEER of Caco-2 cells before and after treatment was measured using a Millicell ERS system (Millipore, Billerica, Mass.). For epithelial permeability assay, 3-5 kDa FITC-Dextran (FD4; Sigma) was added to the well (apical side) and translocation of FD4 to the basal side was monitored by a spectrophotometer (Spectramax).

The Interaction Between Lactobacilli and L. monocytogenes Cells.

L. monocytogenes F4244, L. innocua F4248, LbcWT, LbcLAP$^{Lm}$, and LbcLAP$^{Lin}$ were cultured for 16-18 h at 37° C. in TSBYE, MRS, or MRS supplemented with 2 µg/ml erythromycin broth, respectively (see section 3.2.1). All cultures were pelleted by centrifugation at 8000×g for 3 min and washed with sterile PBS. All cellular concentrations were serially diluted to obtain a cell concentration of $10^6$ cfu/ml. L. monocytogenes or L. innocua were allowed to interact with the individual probiotic strains (LbcWT, LbcLAP$^{Lm}$, or LbcLAP$^{Lin}$) at a 1:1 concentration in sterile PBS for 1 h at room temperature with constant agitation on Lab Doctor Revolver (MidSci, Valley Park, Mo.). Anti-Listerial magnetic Dynabeads (Cat. No. 71006, Thermofischer Scientific) were used to capture and separate L. monocytogenes and L. innocua from unbound probiotics. Briefly, 20 µl/ml of bead slurry was added to the bacterial mixtures and allowed to interact for 10 min at room temperature with constant agitation. Beads were magnetically separated and washed with sterile PBS-T (0.1%) 3 times (10 min each wash) with constant agitation. Beads were serially diluted and plated on MOX (Neogen) and MRS agar (BD) for enumeration of Listeria and probiotics, respectively.

Mouse Bioassay.

Female mice (A/J; 8-10 weeks of age; n=88) were purchased from Jackson Laboratories (Bar Harbor, Me.). The animal bioassay procedure was approved by the Purdue University Animal Care and Use Committee (1201000595). Upon arrival, mice (2/cage) were housed in a cage that had a solid stainless divider to keep them separated. Shepherd's™ ALPHA-dri® (alpha cellulose) was used for bedding. Animals were provided ad lib feed (Rodent Diet 5001, LabDiet, Brentwood, Mo.) and sterile deionized water, and acclimatized for 5 days before the experiment. A cycle of 12 h artificial light and 12 h darkness was maintained. Relative humidity was 50-60% and the temperature was 20-25° C. Mice were randomly assigned to eight different groups. Fresh preparation of probiotics was supplied daily with sterile deionized water at ~$9×10^9$ CFU/ml for 10 days. Control animals received only water. Probiotic colonization in the gut was monitored daily by analyzing fecal counts of probiotics on agar plates. For challenge experiment, mice received oral gavage of L. monocytogenes F4244 (WT) at a concentration of 5-8.8×$10^8$ CFU/mouse using a feeding tube (Popper) and control mice received PBS (Burkholder et al., 2009). Animals were observed for clinical signs, such as ruffled hair, movement and recumbency, and their feeding and drinking habits.

Mice were euthanized by $CO_2$ asphyxiation at 24 and 48 h pi, and intestine (duodenum, jejunum ileum, cecum, and colon), MLN, spleen, liver, kidney, and blood from the heart were aseptically collected. Feces were collected from each mouse from the time of infection to sacrifice. In some cases, intestinal sections were treated with gentamycin (100 µg/ml) for 2 h to kill extracellular bacteria. Organs/tissues were homogenized using a tissue homogenizer (Cole Parmer, Vernon Hills, Ill.) in 0.5 ml (blood), 4 ml (spleen, kidney, lungs) or 9 ml (feces, intestine, liver) of PBS. MRS agar (Neogen, Lansing, Mich.) containing vancomycin (300 µg/ml) was used for enumeration of LbcWT, and MRS agar containing erythromycin (2 µg/ml) was used for bioengineered strains. Modified Oxford medium (MOX; Oxoid, Basingstoke, Hampshire, UK) was used for enumeration of Listeria. A portion of the ileum (~2 cm) was saved for histopathology, immunohistochemistry, qRT-PCR and other experiments. The gut mucosa was collected from an 8-cm section of ileum for sIgA analysis (Haneberg et al., 1994).

Gut permeability assay. Four to five hour before sacrifice, animals were orally gavaged with 100 µl of FD4 (3 mg/ml; Sigma). Urine voluntarily excreted during euthanasia, was collected from the bag, and blood was collected by cardiac puncture. Sera and urine were appropriately diluted and assayed for FD4 by measuring in a spectrophotometer as described (Condette et al., 2014).

Cytokine Analysis.

Caco-2 monolayers (12 days of incubation) were formed in 12 well plates. Probiotics were introduced to the monolayer at an MOE of 10 and incubated for 24 h. The monolayers were challenged with *L. monocytogenes* (MOE 10) or LPS free purified rLAP (1 mg/ml) for 4 h (Drolia et al., 2018). Culture supernatants were collected and tested for IL-6 and TNF-α content using ELISA kits (Raybiotech ELH-IL6 and ELH-TNF-α). For mouse tissue, IL-6 and TNF-α, mouse-specific ELISA kits (Ray Biotech ELM-TNF-α and ELM-IL6-CL) were used. Briefly, ileal tissue homogenates (100 µl) were incubated overnight (16 h). Primary antibodies specific to IL-6 or TNF-α and streptavidin conjugated secondary antibodies were incubated for 1 h and 45 min, respectively, at room temperature. The color was developed as instructed by the manufacturer.

Histopathology and Immunohistochemistry.

Mouse tissues were fixed in 4% paraformaldehyde and embedded in paraffin. Sections (5 µm thick) were stained with hematoxylin and eosin. Microscopic examination was performed by a board-certified veterinary pathologist and the interpretation was based on standard histopathological morphology. The pathologist was blinded to the treatment groups. The extent of mouse ileal lesions was determined by using a semi-quantitative method that included the amount of inflammatory infiltrate and percentage of goblet cells comprising the villous epithelium. A histomorphological scale for assessing inflammation in the lamina propria of the mucosa is provided as follows: 3, marked amounts (sheets of granulocytes expanding the width of the villous tip); 2, moderate amounts (sheets of granulocytes at the base of the villous); 1, mild amounts (multifocal scattering); and 0, none observed. To estimate percentage of goblet cells, following scale was used: 3, 50% or greater; 2, 25-50%; 1, 11-25%; and 0, <10%. The higher the score, the more likely there is an infection in the intestinal tissues. For $CD3^+$ cell staining, paraffin-embedded intestinal thin sections pre-treated with heat-induced epitope retrieval solution and then blocked with Dako protein block according to manufacturer's instructions. Rabbit anti-human CD3 (1:500) used as the primary antibody followed by labeling with Dako labeled polymer. The stained slides were then scanned and analyzed using Aperio ScanScope and Aperio ImageScope software (v11.2.0.780) (Aperio Technologies, Vista, Calif.) established algorithms as described previously (Jones et al., 1993). For all CD3 immunostained slides, a semi-quantitative histochemical score (H score) was calculated by the formula: (3×% of strongly stained)+(2×% of moderately stained)+(% of weakly stained), giving a range of 0 to 300. This H score was adapted from the Aperio software (Webster and Dunstan, 2014).

Analysis of Tight Junction Protein Expression.

Membrane proteins from Caco-2 monolayers pre-exposed to the probiotic followed by *L. monocytogenes* infection were extracted and analyzed for tight junction protein expression. Western blot intensity measurements for membrane proteins using antibodies (Invitrogen) were determined as the ratio of the intensity of the tight junction protein (ZO-1, claudin-1, and occludin) and adherens junction protein (E-cadherin, β-catenin) bands to the integrated intensity of the β-actin band in the same sample. Additionally, membrane localization of the tight junction proteins was also analyzed by confocal immunofluorescence staining (Yu et al., 2012). Briefly, confluent Caco-2 monolayers were rinsed in PBS, fixed and permeabilized in 5% formaldehyde for 15 min. The Caco-2 monolayers were blocked using 5% normal goat serum in PBS for 1 h at room temperature and then incubated with the primary antibody to ZO-1, Claudin-1, and Occludin or E-cadherin-1 β-catenin (Invitrogen) at 37° C. overnight. The monolayers were then washed with PBS to remove unbound antibody and then incubated with the FITC-conjugated secondary antibody (Anti-mouse/Anti-rabbit IgG) for 1 h at room temperature. DAPI was used for nuclear staining. The monolayers were then washed and imaged using the Leica fluorescence microscope (Leica, model DMLB, Wetzlar, Germany) equipped with SPOT software (version 4.6.4.2, Diagnostic Instruments, Sterling Heights, Mich.).

RNA Preparation and Quantitative Reverse Transcription PCR.

Ileum sections (10-15 mm) of each mouse were collected and immediately transferred to 2.0 ml sterile, DNA/RNase-free cryovials containing RNAlater® (Ambion® by Life Technologies Corp., Carlsbad, Calif.), and stored at −80° C. until RNA extraction. Individual tissue samples were homogenized with TRIzol® reagent (Life Technologies Corp.) using a Tissue-Tearor (BioSpec Products, Inc., Bartlesville, Okla.), and total RNA was isolated with Direct-zol™ RNA MiniPrep Plus kit (Zymo Research Corp., Irvine, Calif.) according to the manufacturer's instructions. Total RNA aliquots were stored at −80° C. until cDNA synthesis. Concentration and quality of the RNA samples were assessed using Agilent 2100 Bioanalyzer (Agilent Technologies, Inc. Headquarters, CA). Quantitative RT-PCR was performed in two-step RT-PCR. Independent cDNA synthesis was performed for all samples (n=3 per group) starting from 100 ng of total RNA using SuperScript® VILO™ Master Mix (Invitrogen, Carlsbad, Calif.) according to the manufacturer's recommendations. Quantitative PCR was carried out in a StepOnePlus™ Real-Time PCR System (Applied Biosystems®, Foster City, Calif.) using Fast SYBR® Green Master Mix (Applied Biosystems®) according to the manufacturer's instructions. Primers for each target gene were selected from previous publications, in addition to GAPDH, chosen as an endogenous control. Three technical replicates for each target gene per sample were included in the qPCR assay. Means of triplicates were taken, and the relative amount of target mRNA was normalized to GAPDH ran in every assay. Relative quantification was evaluated using the Comparative Ct method (AACt), and fold difference ($2^{\Delta\Delta Ct}$) was calculated between control (Control) and treatment groups (Schmittgen and Livak, 2008).

Spleen Cytology and Flow Cytometry.

Mouse splenocytes (n=3 per group) were harvested by mechanical disruption through a 40-micron mesh filter (Fisher Scientific Co., Pittsburgh, Pa.) into supplemented RPMI-1640 (modified Gibco, Life Technologies). Red blood cells were lysed using ACK Lysis buffer (Lonza, Allendale, N.J.). Cells were suspended in PBS with 1% BSA prior to immunostaining. All cells were blocked with anti-mouse CD16/32 (Affymetrix, Santa Clara, Calif.). Direct extracellular staining was performed. Intracellular staining for FoxP3 was performed using the Mouse Regulatory T-cell Staining Kit #2 (Affymetrix) according to the manufacturer's protocol. Fluorescence measurements were performed on an Accuri C6 flow cytometer (BD, Franklin Lakes, N.J.) and analyzed with the manufacture's software. All statistical analyses were performed using GraphPad (GraphPad Software Inc, La Jolla, Calif.). Unstained and isotype control cells were used for preliminary gating included for all subsequent analysis. $CD4^+$ and $CD8\alpha^+$ data were collected by quadrant plot (n=3). $CD11c^+$ data were obtained from detector histogram and averaged between tube 3 and tube 4 for each animal (n=3). [Mean population values were compared using two-way ANOVA to compare treatment groups with and without *L. monocytogenes* infection. Follow-up T-test analysis was performed to compare individual treatment pairs, one-tailed tests were performed only if the two-tailed test showed a significant difference.]

Antibody Response Analysis.

The gut mucosa was collected from an 8 cm section of ileum for analysis of sIgA. Briefly, 96-well polystyrene plates (HBX, Immulon, ThermoFisher) were coated with 100 µl of mucus (diluted 1:100 in carbonate coating buffer) and stored at 4° C. overnight. The wells were washed three times in PBST and then sequentially incubated with 1:100 anti-mouse IgA conjugated to HRP and QuantaBlu substrates (Fisher). The fluorescence intensity was measured (Ex: 340 nm; Em: 420 nm) using a Spectramax fluorescent plate reader (Gemini, Sunnyvale, Calif.). Similarly, *Listeria*-specific IgA levels were also estimated in the mucus samples using ELISA plates sensitized with an overnight culture of *L. monocytogenes* (Lm) F4244 ($10^7$ CFU/well), followed by exposure to mucus samples from each of the animal group. The presence of Lm-specific IgA was then estimated using 1:100 anti-mouse IgA to HRP and QuantaBlu substrate as mentioned above. For analysis of serum IgG levels, 96-well plates were sensitized with serum samples (diluted 1:100 in carbonate coating buffer) at 4° C. overnight, and the IgG levels were detected using anti-mouse IgG (1:2000) and QuantaBlu. In addition, *L. monocytogenes*-specific IgG response was measured following sensitization with the F4244 ($10^7$ CFU/well), followed by exposure to serum and anti-mouse IgG.

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

It is intended that the scope of the present methods and apparatuses be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

REFERENCES CITED

Ahrne, S., and Hagslatt, M.-L. J. (2011). Effect of Lactobacilli on paracellular permeability in the gut. Nutrients 3, 104-117.

Amalaradjou, M. A. R., and Bhunia, A. K. (2012). Modern approaches in probiotics research to control foodborne pathogens. Adv. Food Nutr. Res. 67, 185-239.

Amalaradjou, M. A. R., and Bhunia, A. K. (2013). Bioengineered probiotics, a strategic approach to control enteric infections. Bioengineered 4, 291-299.

Azcarate-Peril, M. A., Sikes, M., and Bruno-Barcena, J. M. (2011). The intestinal microbiota, gastrointestinal environment and colorectal cancer: a putative role for probiotics in prevention of colorectal cancer? Am J Physiol—Gastrointest Liver Physiol 301, G401-G424.

Bailey, T. W., do Nascimento, N. C., and Bhunia, A. K. (2017). Genome sequence of *Listeria monocytogenes* strain F4244, a 4b serotype. Genome Announcements 5, e01324-01317.

Bakker-Zierikzee, A. M., van Tol, E. A. F., Kroes, H., Alles, M. S., Kok, F. J., and Bindels, J. G. (2006). Faecal SIgA secretion in infants fed on pre- or probiotic infant formula. Ped. Allergy Immunol. 17, 134-140.

Bou Ghanem, E. N., Jones, G. S., Myers-Morales, T., Patil, P. D., Hidayatullah, A. N., and D'Orazio, S. E. (2012). InlA promotes dissemination of *Listeria monocytogenes* to the mesenteric lymph nodes during food borne infection of mice. PLoS Pathog 8, e1003015.

Bron, P. A., Kleerebezem, M., Brummer, R.-J., Cani, P. D., Mercenier, A., MacDonald, T. T., Garcia-Ródenas, C. L., and Wells, J. M. (2017). Can probiotics modulate human disease by impacting intestinal barrier function? Brit. J. Nutr. 117, 93-107.

Brun, P., Castagliuolo, I., Leo, V. D., Buda, A., Pinzani, M., Path, G., and Martines, D. (2007). Increased intestinal permeability in obese mice: new evidence in the pathogenesis of nonalcoholic steatohepatitis. Am J. Physiol. Gastrointest. Liver Physiol. 292, G518-G525.

Buriti, F. C. A., Castro, I. A., and Saad, S. M. I. (2010). Viability of *Lactobacillus acidophilus* in synbiotic guava mousses and its survival under in vitro simulated gastrointestinal conditions. Int. J. Food Microbiol. 137, 121-129.

Burkholder, K. M., and Bhunia, A. K. (2010). *Listeria monocytogenes* uses *Listeria* adhesion protein (LAP) to promote bacterial transepithelial translocation, and induces expression of LAP receptor Hsp60. Infect. Immun. 78, 5062-5073.

Burkholder, K. M., Kim, K.-P., Mishra, K., Medina, S., Hahm, B.-K., Kim, H., and Bhunia, A. K. (2009). Expression of LAP, a SecA2-dependent secretory protein, is induced under anaerobic environment. Microbes Infect. 11, 859-867.

Chen, W., Syldath, U., Bellmann, K., Burkart, V., and Kolb, H. (1999). Human 60-kDa Heat-Shock Protein: A Danger Signal to the Innate Immune System. J. Immunol. 162, 3212-3219.

Cho, I.-H., Radadia, A. D., Farrokhzad, K., Ximenes, E., Bae, E., Singh, A. K., Oliver, H., Ladisch, M., Bhunia, A., Applegate, B., et al. (2014). Nano/Micro and Spectroscopic Approaches to Food Pathogen Detection. Annu. Rev. Anal. Chem. 7, 65-88.

Condette, C. J., Khorsi-Cauet, H., Morliere, P., Zabijak, L., Reygner, J., Bach, V., and Gay-Queheillard, J. (2014). Increased gut permeability and bacterial translocation after chronic chlorpyrifos exposure in rats. PLoS One 9, e102217.

Corr, S., Li, Y., Riedel, C. U., O'Toole, P. W., Hill, C., and Gahan, C. G. M. (2007). Bacteriocin production as a mechanism for the antiinfective activity of *Lactobacillus salivarius* UCC118. Proc. Nat. Acad. Sci. (USA) 104, 7617-7621.

Cross, M. L. (2002). Microbes versus microbes: immune signals generated by probiotic lactobacilli and their role in protection against microbial pathogens. FEMS Immunol. Med. Microbiol. 34, 245-253.

Culligan, E. P., Hill, C., and Sleator, R. D. (2009). Probiotics and gastrointestinal disease: successes, problems and future prospects. Gut Pathog 1, 19.

Czuprynski, C. J., Faith, N. G., and Steinberg, H. (2003). A/J mice are susceptible and C57BL/6 mice are resistant to *Listeria monocytogenes* infection by intragastric inoculation. Infect. Immun. 71, 682-689.

Deepti, K., and Vinod, K. K. (2014). Dahi containing *Lactobacillus acidophilus* and *Bifidobacterium bifidum* improves phagocytic potential of macrophages in aged mice. J. Food Sci. Technol. 51, 1147-1153.

Deshpande, G., Rao, S., Keil, A., and Patole, S. (2011). Evidence-based guidelines for use of probiotics in preterm neonates. BMC Med 9, 92.

Disson, O., Grayo, S., Huillet, E., Nikitas, G., Langa-Vives, F., Dussurget, O., Ragon, M., Le Monnier, A., Babinet, C., Cossart, P., et al. (2008). Conjugated action of two species-specific invasion proteins for fetoplacental listeriosis. Nature 455, 1114-1118.

Drolia, R., Tenguria, S., Durkes, A. C., Turner, J. R., and Bhunia, A. K. (2018). *Listeria* adhesion protein induces intestinal epithelial barrier dysfunction for bacterial translocation. Cell Host & Microbe 23, 470-484.

Edelson, B. T., Bradstreet, T. R., Hildner, K., Carrero, J. A., Frederick, K. E., Wumesh, K. C., Belizaire, R., Aoshi, T., Schreiber, R. D., Miller, M. J., et al. (2011). CD8 alpha(+) dendritic cells are an obligate cellular entry point for productive infection by *Listeria monocytogenes*. Immunity 35, 236-248.

Finlay, B. B., and Falkow, S. (1997). Common themes in microbial pathogenicity revisited. *Microbiol. Mol. Biol. Rev.* 61, 136-169.

Focareta, A., Paton, J. C., Morona, R., Cook, J., and Paton, A. W. (2006). A recombinant probiotic for treatment and prevention of cholera. Gastroenterology 130, 1688.

Haneberg, B., Kendall, D., Amerongen, H. M., Apter, F. M., Kraehenbuhl, J. P., and Neutra, M. R. (1994). Induction of specific immunoglobulin A in the small intestine, colon-rectum, and vagina measured by a new method for collection of secretions from local mucosal surfaces. Infect. Immun. 62, 15-23.

Henderson, B., Fares, M. A., and Lund, P. A. (2013). Chaperonin 60: a paradoxical, evolutionarily conserved protein family with multiple moonlighting functions. Biol. Rev. 88, 955-987.

Hill, C., Guarner, F., Reid, G., Gibson, G. R., Merenstein, D. J., Pot, B., Morelli, L., Canani, R. B., Flint, H. J., Salminen, S., et al. (2014). Expert consensus document: The International Scientific Association for Probiotics and Prebiotics consensus statement on the scope and appropriate use of the term probiotic. Nat. Rev. Gastroenterol. Hepatol. 11, 506-514.

Huleatt, J. W., Pilip, I., Kerksiek, K., and Pamer, E. G. (2001). Intestinal and splenic T cell responses to enteric *Listeria monocytogenes* infection: Distinct repertoires of responding CD8 T lymphocytes. J. Immunol. 166, 4065-4073.

Jagadeesan, B., Fleishman Littlejohn, A. E., Amalaradjou, M. A. R., Singh, A. K., Mishra, K. K., La, D., Kihara, D., and Bhunia, A. K. (2011). N-Terminal $Gly_{224}$-$Gly_{411}$ domain in *Listeria* adhesion protein interacts with host receptor Hsp60. PLoS One 6, e20694.

Jagadeesan, B., Koo, O. K., Kim, K. P., Burkholder, K. M., Mishra, K. K., Aroonnual, A., and Bhunia, A. K. (2010). LAP, an alcohol acetaldehyde dehydrogenase enzyme in *Listeria* promotes bacterial adhesion to enterocyte-like Caco-2 cells only in pathogenic species. Microbiology 156, 2782-2795.

Jagannath, C., Hoffmann, H., Sepulveda, E., Actor, J., Wetsel, R., and Hunter, R. (2000). Hypersusceptibility of A/J mice to tuberculosis is in part due to a deficiency of the fifth complement component (C5). 52, 369-379.

Jones, M., Cordell, J. L., Beyers, A. D., Tse, A. G. D., and Mason, D. Y. (1993). Detection of T-cell and B-cell in many animal species using cross-reactive antipeptide antibodies. J. Immunol. 150, 5429-5435.

Kim, H., and Bhunia, A. K. (2013). Secreted *Listeria* adhesion protein (Lap) influences Lap-mediated *Listeria monocytogenes* paracellular translocation through epithelial barrier. Gut Pathog. 5, 16.

Koo, O. K., Amalaradjou, M. A. R., and Bhunia, A. K. (2012). Recombinant probiotic expressing *Listeria* adhesion protein attenuates *Listeria monocytogenes* virulence in vitro. PLoS One 7, e29277.

Lecuit, M., Dramsi, S., Gottardi, C., Fedor-Chaiken, M., Gumbiner, B., and Cossart, P. (1999). A single amino acid in E-cadherin responsible for host specificity towards the human pathogen *Listeria monocytogenes*. EMBO J. 18, 3956-3963.

Lecuit, M., Vandormael-Pournin, S., Lefort, J., Huerre, M., Gounon, P., Dupuy, C., Babinet, C., and Cossart, P. (2001). A transgenic model for listeriosis: role of internalin in crossing the intestinal barrier. Science 292, 1722-1725.

Lee, M. T., Chen, F. Y., and Huang, H. W. (2004). Energetics of pore formation induced by membrane active peptides. Biochemistry 43, 3590-3599.

Ly, N. P., Litonjua, A., Gold, D. R., and Celedon, J. C. (2011). Gut microbiota, probiotics, and vitamin D: Inter-related exposures influencing allergy, asthma, and obesity? J. Allergy Clin. Immunol. 127, 1087-1094.

Ma, T. Y., Iwamoto, G. K., Hoa, N. T., Akotia, V., Pedram, A., Boivin, M. A., and Said, H. M. (2004). TNF-α induced increase in intestinal epithelial tight junction permeability requires NF-kB activation. Am. J. Physiol. Gastrointes. Liver Physiol. 286, G367-G376.

Maassen, C. B., Laman, J. D., den Bak-Glashouwer, M. J., Tielen, F. J., van Holten-Neelen, J. C., Hoogteijling, L., Antonissen, C., Leer, R. J., Pouwels, P. H., Boersma, W. J., et al. (1999). Instruments for oral disease-intervention strategies: recombinant *Lactobacillus casei* expressing tetanus toxin fragment C for vaccination or myelin proteins for oral tolerance induction in multiple sclerosis. Vaccine 17, 2117-2128.

Mantis, N. J., Rol, N., and Corthesy, B. (2011). Secretory IgA's complex roles in immunity and mucosal homeostasis in the gut. Mucosal Immunol. 4, 603-611.

Marco, A. J., Altimira, J., Prats, N., Lopez, S., Dominguez, L., Domingo, M., and Briones, V. (1997). Penetration of *Listeria monocytogenes* in mice infected by the oral route. Microb. Pathog. 23, 255-263.

Michon, C., Langella, P., Eijsink, V. G. H., Mathiesen, G., and Chatel, J. M. (2016). Display of recombinant proteins at the surface of lactic acid bacteria: strategies and applications. Microb. Cell Factories 15, 70.

Mishra, K. K., Mendonca, M., Aroonnual, A., Burkholder, K. M., and Bhunia, A. K. (2011). Genetic organization and molecular characterization of secA2 locus in *Listeria* species. Gene 489, 76-85.

Mohamadzadeh, M., Durmaz, E., Zadeh, M., Pakanati, K. C., Gramarossa, M., Cohran, V., and Klaenhammer, T. R. (2010). Targeted expression of anthrax protective antigen by *Lactobacillus* gasseri as an anthrax vaccine. Future Microbiol. 5, 1289-1296.

Ng, S. C., Hart, A. L., Kamm, M. A., Stagg, A. J., and Knight, S. C. (2009). Mechanisms of action of probiotics: Recent advances. Inflamm. Bowel Dis. 15, 300-310.

Niers, L. E. M., Timmerman, H. M., Rijkers, G. T., van Bleek, G. M., van Uden, N. O. P., Knol, E. F., Kapsenberg, M. L., Kimpen, J. L. L., and Hoekstra, M. O. (2005). Identification of strong interleukin-10 inducing lactic acid bacteria which down-regulate T helper type 2 cytokines. Clin. Exp. Allergy 35, 1481-1489.

Nikitas, G., Deschamps, C., Disson, O., Niault, T., Cossart, P., and Lecuit, M. (2011). Transcytosis of *Listeria monocytogenes* across the intestinal barrier upon specific targeting of goblet cell accessible E-cadherin. J. Exp. Med. 208, 2263-2277.

Pagnini, C., Saeed, R., Bamias, G., Arseneau, K. O., Pizarro, T. T., and Cominelli, F. (2010). Probiotics promote gut health through stimulation of epithelial innate immunity. Proc. Natl. Acad. Sci. U.S.A. 107, 454-459.

Pentecost, M., Otto, G., Theriot, J. A., and Amieva, M. R. (2006). *Listeria monocytogenes* invades the epithelial junctions at sites of cell extrusion. PLoS Pathog 2, e3.

Pockley, A. G. (2003). Heat shock proteins as regulators of the immune response. The Lancet 362, 469-476.

Pouwels, P. H., Vriesema, A., Martinez, B., Tielen, F. J., Seegers, J. F., Leer, R. J., Jore, J., and Smit, E. (2001). Lactobacilli as vehicles for targeting antigens to mucosal tissues by surface exposition of foreign antigens. Methods Enzymol 336, 369-389.

Pron, B., Boumaila, C., Jaubert, F., Sarnacki, S., Monnet, J., Berche, P., and Gaillard, J. (1998). Comprehensive study of the intestinal stage of listeriosis in a rat ligated ileal loop system. Infect. Immun. 66, 747-755.

Rothe, J., Lesslauer, W., Lotscher, H., Lang, Y., Koebel, P., Kontgen, F., Althage, A., Zinkernagel, R., Steinmetz, M., and Bluethmann, H. (1993). Mice lacking the tumour necrosis factor receptor 1 are resistant to TNF-mediated toxicity but highly susceptible to infection by *Listeria monocytogenes*. Nature 364, 798-802.

Sakai, F., Hosoya, T., Ono-Ohmachi, A., Ukibe, K., Ogawa, A., Moriya, T., Kadooka, Y., Shiozaki, T., Nakagawa, H., Nakayama, Y., et al. (2014). *Lactobacillus* gasseri SBT2055 Induces TGF-beta Expression in Dendritic Cells and Activates TLR2 Signal to Produce IgA in the Small Intestine. PLoS One 9, e105370.

Salminen, S., Nybom, S., Meriluoto, J., Collado, M. C., Vesterlund, S., and El-Nezami, H. (2010). Interaction of probiotics and pathogens—benefits to human health? Curr. Opin. Biotechnol. 21, 157-167.

Sanders, M. E., Lenoir-Wijnkoop, I., Salminen, S., Merenstein, D. J., Gibson, G. R., Petschow, B. W., Nieuwdorp, M., Tancredi, D. J., Cifelli, C. J., Jacques, P., et al. (2014). Probiotics and prebiotics: prospects for public health and nutritional recommendations. Annals New York Acad. Sci. 1309, 19-29.

Schmittgen, T. D., and Livak, K. J. (2008). Analyzing real-time PCR data by the comparative C-T method. Nat. Protoc. 3, 1101-1108.

Schuchat, A., Swaminathan, B., and Broome, C. V. (1991). Epidemiology of human listeriosis. Clin. Microbiol. Rev. 4, 169-183.

Sleator, R. D., Watson, D., Hill, C., and Gahan, C. G. M. (2009). The interaction between *Listeria monocytogenes* and the host gastrointestinal tract. Microbiology 155, 2463-2475.

Vance, R. E., Isberg, R. R., and Portnoy, D. A. (2009). Patterns of pathogenesis: discrimination of pathogenic and nonpathogenic microbes by the innate immune system. Cell Host Microbe 6, 10-21.

Villena, J., Racedo, S., Aguero, G., Bru, E., Medina, M., and Alvarez, S. (2005). *Lactobacillus casei* improves resistance to pneumococcal respiratory infection in malnourished mice. J. Nutr. 135, 1462-1469.

Wampler, J. L., Kim, K. P., Jaradat, Z., and Bhunia, A. K. (2004). Heat shock protein 60 acts as a receptor for the *Listeria* adhesion protein in Caco-2 cells. Infect. Immun. 72, 931-936.

Webster, J. D., and Dunstan, R. W. (2014). Whole-Slide Imaging and Automated Image Analysis: Considerations and Opportunities in the Practice of Pathology. Vet. Pathol. 51, 211-223.

Wollert, T., Pasche, B., Rochon, M., Deppenmeier, S., van den Heuvel, J., Gruber, A. D., Heinz, D. W., Lengeling, A., and Schubert, W. D. (2007). Extending the host range of *Listeria monocytogenes* by rational protein design. Cell 129, 891-902.

Xayarath, B., and Freitag, N. E. (2012). Optimizing the balance between host and environmental survival skills: lessons learned from *Listeria monocytogenes*. Future Microbiol. 7, 839-852.

Yu, Q., Wang, Z., and Yang, Q. (2012). *Lactobacillus amylophilus* D14 protects tight junction from enteropathogenic bacteria damage in Caco-2 cells. 95, 5580-5587.

Zareie, M., Johnson-Henry, K., Jury, J., Yang, P. C., Ngan, B. Y., McKay, D. M., Soderholm, J. D., Perdue, M. H., and Sherman, P. M. (2006). Probiotics prevent bacterial translocation and improve intestinal barrier function in rats following chronic psychological stress. Gut 55, 1553-1560.

Zhou, Y., Qin, H., Zhang, M., Shen, T., Chen, H., Ma, Y., Chu, Z., Zhang, P., and Liu, Z. (2010). *Lactobacillus plantarum* inhibits intestinal epithelial barrier dysfunction induced by unconjugated bilirubin. Brit. J. Nutr. 104, 390-401.

What is claimed is:

1. A method for improving immunity and exerting immunomodulatory and anti-inflammatory effects in an animal comprising adding an effective amount of a Next Generation Bioengineered Probiotic (NGBP) to a feed of said animal, wherein said NGBP is a bioengineered *Lactobacillus casei* probiotic expressing a polypeptide having the amino add sequence of SEQ ID NO: 1 or SEQ ID NO: 2.

2. The method of claim 1, wherein said animal is selected from the group consisting of a pig, sheep, goat, chicken, turkey, cat, dog and cattle.

3. The method of claim 1, wherein the NGBP is lyophilized.

4. A method to eliminate or reduce antibiotic use in an animal feed for improving animal health and/or meat production comprising the step of adding an effective amount of a Next Generation Bioengineered Probiotic (NGBP) to a feed of said animal, wherein said NGBP is a bioengineered *Lactobacillus* casei probiotic expressing a polypeptide having the amino acid sequence of SEQ ID NO: 1 or SEQ ID NO: 2.

5. The method of claim 4, wherein said animal is selected from the group consisting of a pig, sheep, goat, chicken, turkey, cat, dog and cattle.

6. The method of claim 4, wherein the NGBP is lyophilized.

* * * * *